(12) United States Patent
Lee et al.

(10) Patent No.: US 8,768,630 B2
(45) Date of Patent: Jul. 1, 2014

(54) MIRNA TARGET PREDICTION

(75) Inventors: Inhan Lee, Ann Arbor, MI (US); Subramanian S. Ajay, Rockville, MD (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/032,377

(22) Filed: Feb. 22, 2011

(65) Prior Publication Data

US 2012/0015351 A1    Jan. 19, 2012

Related U.S. Application Data

(60) Provisional application No. 61/306,353, filed on Feb. 19, 2010.

(51) Int. Cl.
*G06F 19/00* (2011.01)
*C12N 15/85* (2006.01)
*C12N 15/82* (2006.01)
*C12N 15/74* (2006.01)
*C12N 15/11* (2006.01)
*G06F 19/18* (2011.01)
*G06F 19/24* (2011.01)

(52) U.S. Cl.
CPC ............... *G06F 19/18* (2013.01); *G06F 19/24* (2013.01)
USPC ............ 702/20; 435/455; 435/468; 435/471; 536/24.5

(58) Field of Classification Search
CPC .... C12N 2310/141; G06F 19/16; G06F 19/18
See application file for complete search history.

(56) References Cited

U.S. PATENT DOCUMENTS

2009/0012720 A1*  1/2009  Huynh et al. .................... 702/20

OTHER PUBLICATIONS

Lee et al. New class of microRNA targets containing simultaneous 5'-UTR and 3'-UTR interaction sites Genome Research, vol. 19, pp. 1175-1183 (2009).*

Krueger, J. et al, "RNAhybrid: microRNA target prediction easy, fast and flexible," Nucleic Acids Research, 2006, v. 34, Web Server issue, pp. W451-W454.

Griffiths-Jones, S. et al., "miRBase: tools for microRNA genomics," Nucleic Acids Research, 2008, v. 36, Database issue, pp. D154-D158.

Griffiths-Jones, S., "The microRNA Registry," Nucleic Acids Research 2004, v. 32, Database issue, pp. D109- D111.

Robins, H. et al., "Incoporating structure to predict microRNA targets," PNAS, Mar. 15, 2005, v. 102, No. 11, pp. 4006-4009.

Kiriakidou, M. et al., "A combined computational-experimental approach predicts human microRNA targets," Genes & Development, 18:1165-1178, copyright 2004 by Cold Spring Harbor Laboratory Press.

Lewis, B.P. et al., "Conserved Seed Pairing, Often Flanked by Adenosines, Indicates that Thousands of Human Genes are microRNA Targets," Cell, v. 120, Jan. 14, 2005, pp. 15-20.

Rehmsmeier, M. et al., "Fast and effective prediction of microRNA/target databases," RNA (2004), 10:1507-1517, copyright 2004.

Enright, A.J. et al., "MicroRNA targets in Drosophila," Genome Biology 2003, v. 5, Issue 1, Article R1, 14 pp.

Brown, J.R. et al., "A computational view of microRNAs and their targets," DDT, v. 10, No. 8, Apr. 2005, pp. 595-601.

Krek, A. et al., "Combinatorial microRNA target predictions," Nature Genetics, v. 37, No. 5, May 2005, pp. 495-500.

Bentwich, I. et al., "Identification of hundreds of conserved and nonconserved human microRNAs," Nature Genetics, v. 37, No. 7, Jul. 2005, pp. 766-770.

Lu, J. et al., "MicroRNA expression profiles classify human cancers," Nature, v. 435, Jun. 9, 2005, pp. 834-838.

Song, Ji-Joon et al., "Crystal Structure of Argonaute and its Implications for RISC Slicer Activity," Science, v. 305, Sep. 3, 2004, pp. 1434-1437.

Lewis, B.P. et al., "Prediction of Mammalian MicroRNA Targets," Cell, v. 115, Dec. 26, 2003, pp. 787-798.

Ma, Jin-Biao et al., "Structural Basis for 5'-end-specific recognition of guide RNA by the A. fulgidus Piwi protein," NATURE, v. 434, Mar. 31, 2005, pp. 666-670.

Lee, R.C. et al., "The C. elegans Heterochronic Gene lin-4 Encodes Small RNSAs with Antisense Complementary to lin-14," Cell, v. 75, Dec. 3, 1993, pp. 843-854.

Baek, D. et al., "The impact of microRNAs on protein output," Nature, v. 455, Sep. 4, 2008, pp. 64-73.

Xie, X. et al., "Systematic discovery of regulatory motifs in human promoters and 3' UTRs by comparison of several mammals," Nature, v. 434, Mar. 17, 2005, pp. 338-345.

* cited by examiner

*Primary Examiner* — John S Brusca
(74) *Attorney, Agent, or Firm* — Brooks Kushman P.C.

(57) ABSTRACT

The present invention relates to generation (e.g., synthesis) of proteins. In particular, the present invention provides methods to predict miRNA targets using sequence similarity and thermodynamic stability of miRNA-bridges across both 3' and 5' UTR. Such methods find use in research, diagnostic and therapeutic settings (e.g., to discover targets, drugs, diagnostic products, etc.).

11 Claims, 12 Drawing Sheets

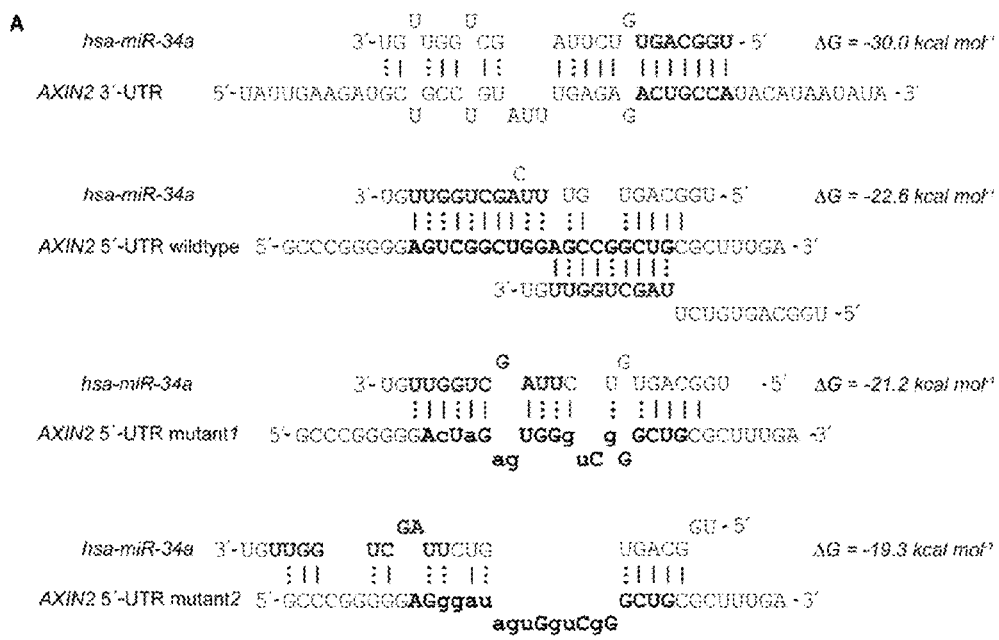
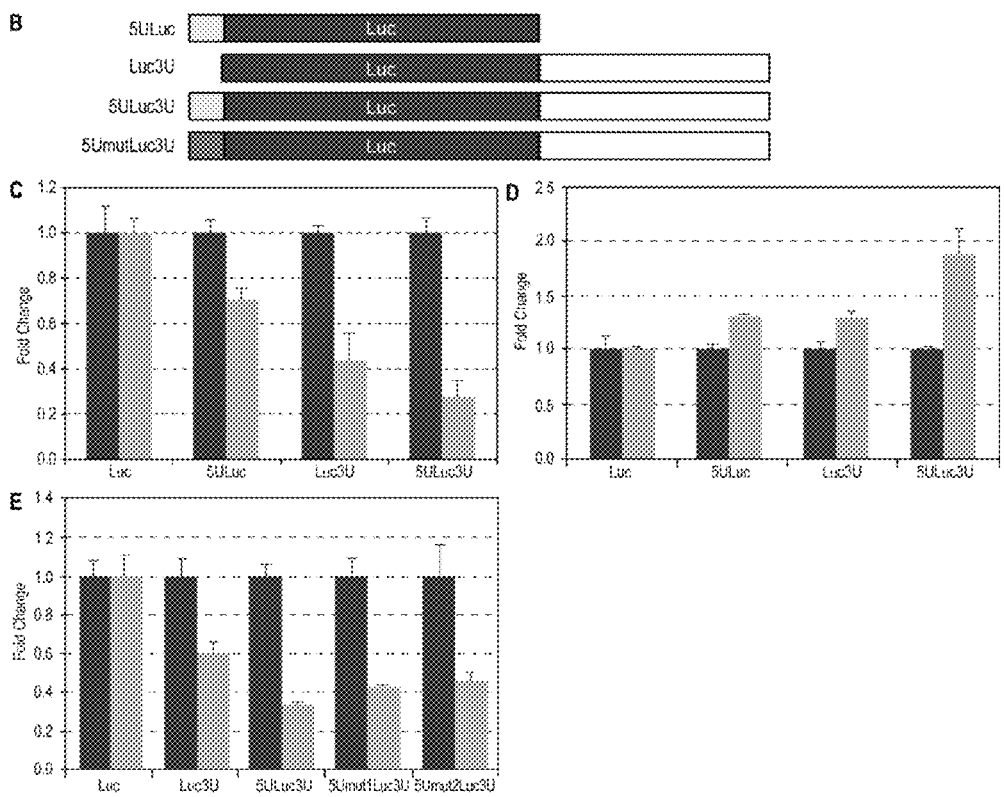
Fig. 7

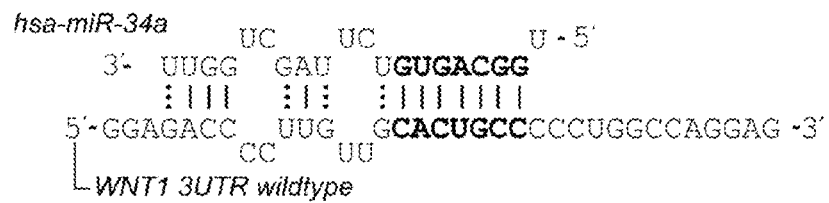
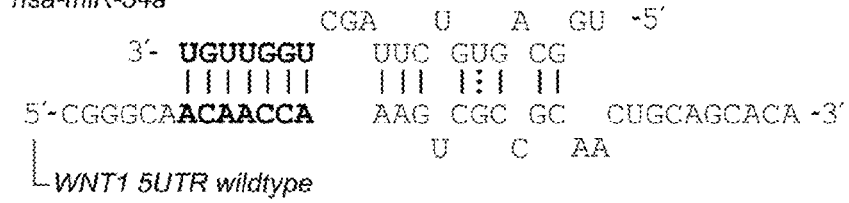
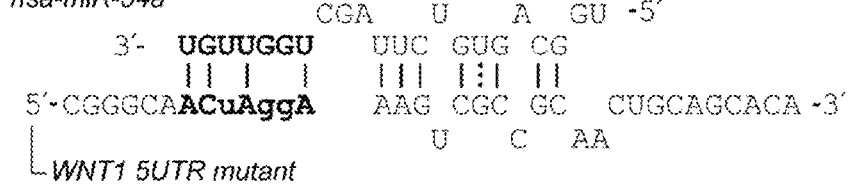
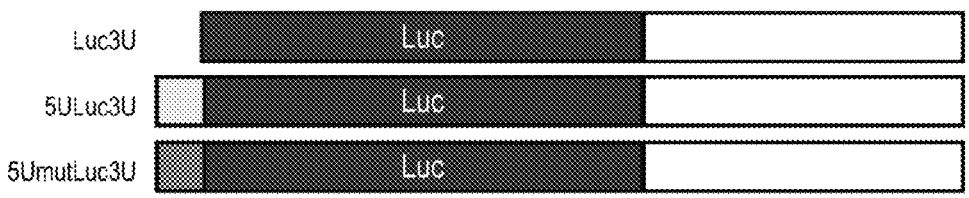
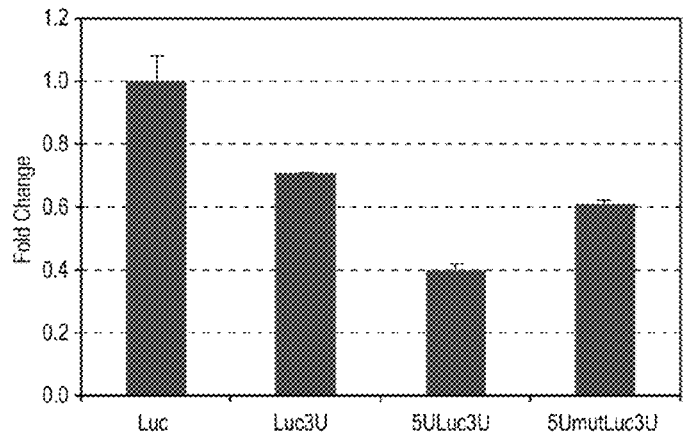
Fig. 8

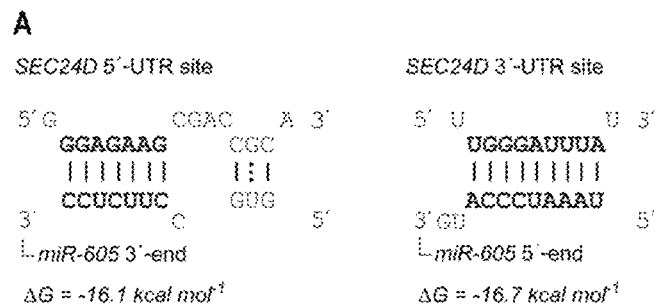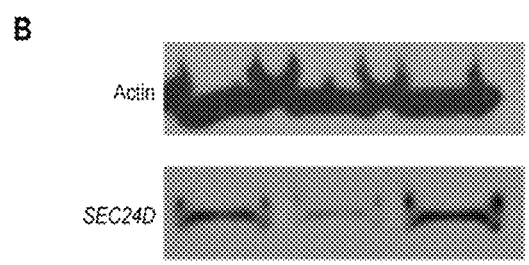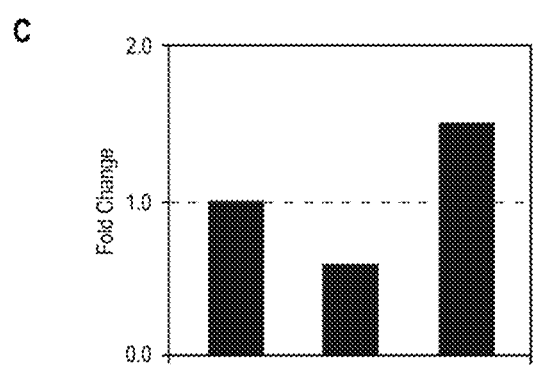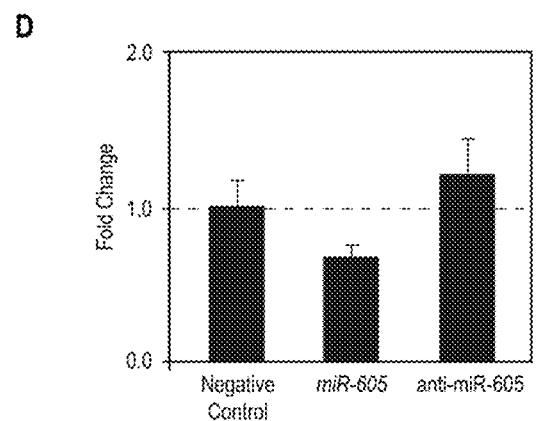
Fig. 10

SEQUENCE LISTING

<160> NUMBER OF SEQ ID NOS: 465

<210> SEQ ID NO 1
<211> LENGTH: 22
<212> TYPE: DNA
<213> ORGANISM: Homo sapiens

<400> SEQUENCE: 1
tgaggtagta ggttgtatag tt                                            22

<210> SEQ ID NO 2
<211> LENGTH: 22
<212> TYPE: DNA
<213> ORGANISM: Homo sapiens

<400> SEQUENCE: 2
tgaggtagta ggttgtgtgg tt                                            22

<210> SEQ ID NO 3
<211> LENGTH: 22
<212> TYPE: DNA
<213> ORGANISM: Homo sapiens

<400> SEQUENCE: 3
tgaggtagta ggttgtatgg tt                                            22

<210> SEQ ID NO 4
<211> LENGTH: 21
<212> TYPE: DNA
<213> ORGANISM: Homo sapiens

<400> SEQUENCE: 4
agaggtagta ggttgcatag t                                             21

<210> SEQ ID NO 5
<211> LENGTH: 21
<212> TYPE: DNA
<213> ORGANISM: Homo sapiens

<400> SEQUENCE: 5
tgaggtagga ggttgtatag t                                             21

<210> SEQ ID NO 6
<211> LENGTH: 22
<212> TYPE: DNA
<213> ORGANISM: Homo sapiens

<400> SEQUENCE: 6
tgaggtagta gattgtatag tt                                            22

<210> SEQ ID NO 7
<211> LENGTH: 22
<212> TYPE: DNA
<213> ORGANISM: Homo sapiens

<400> SEQUENCE: 7
tagcagcaca taatggtttg tg                                            22

<210> SEQ ID NO 8
<211> LENGTH: 22
<212> TYPE: DNA
<213> ORGANISM: Homo sapiens

<400> SEQUENCE: 8

```
tagcagcacg taaatattgg cg                                              22

<210> SEQ ID NO 9
<211> LENGTH: 24
<212> TYPE: DNA
<213> ORGANISM: Homo sapiens

<400> SEQUENCE: 9
caaagtgctt acagtgcagg tagt                                            24

<210> SEQ ID NO 10
<211> LENGTH: 20
<212> TYPE: DNA
<213> ORGANISM: Homo sapiens

<400> SEQUENCE: 10
actgcagtga aggcacttgt                                                 20

<210> SEQ ID NO 11
<211> LENGTH: 22
<212> TYPE: DNA
<213> ORGANISM: Homo sapiens

<400> SEQUENCE: 11
taaggtgcat ctagtgcaga ta                                              22

<210> SEQ ID NO 12
<211> LENGTH: 23
<212> TYPE: DNA
<213> ORGANISM: Homo sapiens

<400> SEQUENCE: 12
tgtgcaaatc tatgcaaaac tga                                             23

<210> SEQ ID NO 13
<211> LENGTH: 23
<212> TYPE: DNA
<213> ORGANISM: Homo sapiens

<400> SEQUENCE: 13
tgtgcaaatc catgcaaaac tga                                             23

<210> SEQ ID NO 14
<211> LENGTH: 23
<212> TYPE: DNA
<213> ORGANISM: Homo sapiens

<400> SEQUENCE: 14
taaagtgctt atagtgcagg tag                                             23

<210> SEQ ID NO 15
<211> LENGTH: 22
<212> TYPE: DNA
<213> ORGANISM: Homo sapiens

<400> SEQUENCE: 15
tagcttatca gactgatgtt ga                                              22

<210> SEQ ID NO 16
<211> LENGTH: 22
<212> TYPE: DNA
<213> ORGANISM: Homo sapiens
```

<400> SEQUENCE: 16
aagctgccag ttgaagaact gt                                            22

<210> SEQ ID NO 17
<211> LENGTH: 21
<212> TYPE: DNA
<213> ORGANISM: Homo sapiens

<400> SEQUENCE: 17
atcacattgc cagggatttc c                                             21

<210> SEQ ID NO 18
<211> LENGTH: 23
<212> TYPE: DNA
<213> ORGANISM: Homo sapiens

<400> SEQUENCE: 18
gtgcctactg agctgatatc agt                                           23

<210> SEQ ID NO 19
<211> LENGTH: 22
<212> TYPE: DNA
<213> ORGANISM: Homo sapiens

<400> SEQUENCE: 19
tggctcagtt cagcaggaac ag                                            22

<210> SEQ ID NO 20
<211> LENGTH: 22
<212> TYPE: DNA
<213> ORGANISM: Homo sapiens

<400> SEQUENCE: 20
cattgcactt gtctcggtct ga                                            22

<210> SEQ ID NO 21
<211> LENGTH: 21
<212> TYPE: DNA
<213> ORGANISM: Homo sapiens

<400> SEQUENCE: 21
ttcaagtaat ccaggatagg c                                             21

<210> SEQ ID NO 22
<211> LENGTH: 22
<212> TYPE: DNA
<213> ORGANISM: Homo sapiens

<400> SEQUENCE: 22
ttcaagtaat tcaggatagg tt                                            22

<210> SEQ ID NO 23
<211> LENGTH: 21
<212> TYPE: DNA
<213> ORGANISM: Homo sapiens

<400> SEQUENCE: 23
ttcacagtgg ctaagttccg c                                             21

<210> SEQ ID NO 24
<211> LENGTH: 22
<212> TYPE: DNA
<213> ORGANISM: Homo sapiens

```
<400> SEQUENCE: 24
aaggagctca cagtctattg ag                                              22

<210> SEQ ID NO 25
<211> LENGTH: 21
<212> TYPE: DNA
<213> ORGANISM: Homo sapiens

<400> SEQUENCE: 25
tagcaccatc tgaaatcggt t                                               21

<210> SEQ ID NO 26
<211> LENGTH: 22
<212> TYPE: DNA
<213> ORGANISM: Homo sapiens

<400> SEQUENCE: 26
tgtaaacatc ctcgactgga ag                                              22

<210> SEQ ID NO 27
<211> LENGTH: 22
<212> TYPE: DNA
<213> ORGANISM: Homo sapiens

<400> SEQUENCE: 27
ctttcagtcg gatgtttgca gc                                              22

<210> SEQ ID NO 28
<211> LENGTH: 21
<212> TYPE: DNA
<213> ORGANISM: Homo sapiens

<400> SEQUENCE: 28
ggcaagatgc tggcatagct g                                               21

<210> SEQ ID NO 29
<211> LENGTH: 21
<212> TYPE: DNA
<213> ORGANISM: Homo sapiens

<400> SEQUENCE: 29
tattgcacat tactaagttg c                                               21

<210> SEQ ID NO 30
<211> LENGTH: 19
<212> TYPE: DNA
<213> ORGANISM: Homo sapiens

<400> SEQUENCE: 30
gtgcattgta gttgcattg                                                  19

<210> SEQ ID NO 31
<211> LENGTH: 21
<212> TYPE: DNA
<213> ORGANISM: Homo sapiens

<400> SEQUENCE: 31
tattgcactt gtcccggcct g                                               21

<210> SEQ ID NO 32
<211> LENGTH: 22
<212> TYPE: DNA
```

```
<213> ORGANISM: Homo sapiens

<400> SEQUENCE: 32
aaagtgctgt tcgtgcaggt ag                                              22

<210> SEQ ID NO 33
<211> LENGTH: 22
<212> TYPE: DNA
<213> ORGANISM: Homo sapiens

<400> SEQUENCE: 33
ttcaacgggt atttattgag ca                                              22

<210> SEQ ID NO 34
<211> LENGTH: 22
<212> TYPE: DNA
<213> ORGANISM: Homo sapiens

<400> SEQUENCE: 34
tttggcacta gcacattttt gc                                              22

<210> SEQ ID NO 35
<211> LENGTH: 22
<212> TYPE: DNA
<213> ORGANISM: Homo sapiens

<400> SEQUENCE: 35
tgaggtagta agttgtattg tt                                              22

<210> SEQ ID NO 36
<211> LENGTH: 22
<212> TYPE: DNA
<213> ORGANISM: Homo sapiens

<400> SEQUENCE: 36
aacccgtaga tccgatcttg tg                                              22

<210> SEQ ID NO 37
<211> LENGTH: 22
<212> TYPE: DNA
<213> ORGANISM: Homo sapiens

<400> SEQUENCE: 37
aacccgtaga tccgaacttg tg                                              22

<210> SEQ ID NO 38
<211> LENGTH: 22
<212> TYPE: DNA
<213> ORGANISM: Homo sapiens

<400> SEQUENCE: 38
tacagtactg tgataactga ag                                              22

<210> SEQ ID NO 39
<211> LENGTH: 23
<212> TYPE: DNA
<213> ORGANISM: Homo sapiens

<400> SEQUENCE: 39
tagcaccatt tgaaatcagt gtt                                             23

<210> SEQ ID NO 40
<211> LENGTH: 23
```

```
<212> TYPE: DNA
<213> ORGANISM: Homo sapiens

<400> SEQUENCE: 40
agcagcattg tacagggcta tga                                    23

<210> SEQ ID NO 41
<211> LENGTH: 20
<212> TYPE: DNA
<213> ORGANISM: Homo sapiens

<400> SEQUENCE: 41
tcaaatgctc agactcctgt                                        20

<210> SEQ ID NO 42
<211> LENGTH: 24
<212> TYPE: DNA
<213> ORGANISM: Homo sapiens

<400> SEQUENCE: 42
aaaagtgctt acagtgcagg tagc                                   24

<210> SEQ ID NO 43
<211> LENGTH: 23
<212> TYPE: DNA
<213> ORGANISM: Homo sapiens

<400> SEQUENCE: 43
agcagcattg tacagggcta tca                                    23

<210> SEQ ID NO 44
<211> LENGTH: 21
<212> TYPE: DNA
<213> ORGANISM: Homo sapiens

<400> SEQUENCE: 44
ctgacctatg aattgacagc c                                      21

<210> SEQ ID NO 45
<211> LENGTH: 21
<212> TYPE: DNA
<213> ORGANISM: Homo sapiens

<400> SEQUENCE: 45
taggtagttt catgttgttg g                                      21

<210> SEQ ID NO 46
<211> LENGTH: 22
<212> TYPE: DNA
<213> ORGANISM: Homo sapiens

<400> SEQUENCE: 46
ttcaccacct tctccaccca gc                                     22

<210> SEQ ID NO 47
<211> LENGTH: 19
<212> TYPE: DNA
<213> ORGANISM: Homo sapiens

<400> SEQUENCE: 47
ggtccagagg ggagatagg                                         19

<210> SEQ ID NO 48
```

-continued

```
<211> LENGTH: 23
<212> TYPE: DNA
<213> ORGANISM: Homo sapiens

<400> SEQUENCE: 48
cccagtgttc agactacctg ttc                                              23

<210> SEQ ID NO 49
<211> LENGTH: 22
<212> TYPE: DNA
<213> ORGANISM: Homo sapiens

<400> SEQUENCE: 49
tacagtagtc tgcacattgg tt                                               22

<210> SEQ ID NO 50
<211> LENGTH: 22
<212> TYPE: DNA
<213> ORGANISM: Homo sapiens

<400> SEQUENCE: 50
ataagacgag caaaaagctt gt                                               22

<210> SEQ ID NO 51
<211> LENGTH: 21
<212> TYPE: DNA
<213> ORGANISM: Homo sapiens

<400> SEQUENCE: 51 cttttttgcgg tctgggcttg c                                               21

<210> SEQ ID NO 52
<211> LENGTH: 22
<212> TYPE: DNA
<213> ORGANISM: Homo sapiens

<400> SEQUENCE: 52
tcagtgcact acagaacttt gt                                               22

<210> SEQ ID NO 53
<211> LENGTH: 23
<212> TYPE: DNA
<213> ORGANISM: Homo sapiens

<400> SEQUENCE: 53
tgtaaacatc ctacactctc agc                                              23

<210> SEQ ID NO 54
<211> LENGTH: 22
<212> TYPE: DNA
<213> ORGANISM: Homo sapiens

<400> SEQUENCE: 54
tgtaaacatc cccgactgga ag                                               22

<210> SEQ ID NO 55
<211> LENGTH: 18
<212> TYPE: DNA
<213> ORGANISM: Homo sapiens

<400> SEQUENCE: 55
tctacagtgc acgtgtct                                                    18
```

```
<210> SEQ ID NO 56
<211> LENGTH: 20
<212> TYPE: DNA
<213> ORGANISM: Homo sapiens

<400> SEQUENCE: 56
gtgtgtggaa atgcttctgc                                              20

<210> SEQ ID NO 57
<211> LENGTH: 22
<212> TYPE: DNA
<213> ORGANISM: Homo sapiens

<400> SEQUENCE: 57
tggaagacta gtgatttgt tg                                            22

<210> SEQ ID NO 58
<211> LENGTH: 23
<212> TYPE: DNA
<213> ORGANISM: Homo sapiens

<400> SEQUENCE: 58
taccctgtag atccgaattt gtg                                          23

<210> SEQ ID NO 59
<211> LENGTH: 22
<212> TYPE: DNA
<213> ORGANISM: Homo sapiens

<400> SEQUENCE: 59
taccctgtag aaccgaattt gt                                           22

<210> SEQ ID NO 60
<211> LENGTH: 23
<212> TYPE: DNA
<213> ORGANISM: Homo sapiens

<400> SEQUENCE: 60
tggcagtgtc ttagctggtt gtt                                          23

<210> SEQ ID NO 61
<211> LENGTH: 23
<212> TYPE: DNA
<213> ORGANISM: Homo sapiens

<400> SEQUENCE: 61
aacattcaac gctgtcggtg agt                                          23

<210> SEQ ID NO 62
<211> LENGTH: 22
<212> TYPE: DNA
<213> ORGANISM: Homo sapiens

<400> SEQUENCE: 62
aacattcatt gctgtcggtg gg                                           22

<210> SEQ ID NO 63
<211> LENGTH: 22
<212> TYPE: DNA
<213> ORGANISM: Homo sapiens

<400> SEQUENCE: 63
aacattcaac ctgtcggtga gt                                           22
```

```
<210> SEQ ID NO 64
<211> LENGTH: 22
<212> TYPE: DNA
<213> ORGANISM: Homo sapiens

<400> SEQUENCE: 64
tttggcaatg gtagaactca ca                                              22

<210> SEQ ID NO 65
<211> LENGTH: 21
<212> TYPE: DNA
<213> ORGANISM: Homo sapiens

<400> SEQUENCE: 65
tggttctaga cttgccaact a                                               21

<210> SEQ ID NO 66
<211> LENGTH: 23
<212> TYPE: DNA
<213> ORGANISM: Homo sapiens

<400> SEQUENCE: 66
tatggcactg gtagaattca ctg                                             23

<210> SEQ ID NO 67
<211> LENGTH: 21
<212> TYPE: DNA
<213> ORGANISM: Homo sapiens

<400> SEQUENCE: 67
tcgtgtcttg tgttgcagcc g                                               21

<210> SEQ ID NO 68
<211> LENGTH: 23
<212> TYPE: DNA
<213> ORGANISM: Homo sapiens

<400> SEQUENCE: 68
cccagtgttt agactatctg ttc                                             23

<210> SEQ ID NO 69
<211> LENGTH: 22
<212> TYPE: DNA
<213> ORGANISM: Homo sapiens

<400> SEQUENCE: 69
gtgaaatgtt taggaccact ag                                              22

<210> SEQ ID NO 70
<211> LENGTH: 22
<212> TYPE: DNA
<213> ORGANISM: Homo sapiens

<400> SEQUENCE: 70 ttcccttgt catcctatgc ct                                               22

<210> SEQ ID NO 71
<211> LENGTH: 22
<212> TYPE: DNA
<213> ORGANISM: Homo sapiens

<400> SEQUENCE: 71
tccttcattc caccggagtc tg                                              22
```

```
<210> SEQ ID NO 72
<211> LENGTH: 22
<212> TYPE: DNA
<213> ORGANISM: Homo sapiens

<400> SEQUENCE: 72
ctgtgcgtgt gacagcggct ga                                              22

<210> SEQ ID NO 73
<211> LENGTH: 22
<212> TYPE: DNA
<213> ORGANISM: Homo sapiens

<400> SEQUENCE: 73
ttccctttgt catccttcgc ct                                              22

<210> SEQ ID NO 74
<211> LENGTH: 21
<212> TYPE: DNA
<213> ORGANISM: Homo sapiens

<400> SEQUENCE: 74
taacagtctc cagtcacggc c                                               21

<210> SEQ ID NO 75
<211> LENGTH: 22
<212> TYPE: DNA
<213> ORGANISM: Homo sapiens

<400> SEQUENCE: 75
accatcgacc gttgattgta cc                                              22

<210> SEQ ID NO 76
<211> LENGTH: 21
<212> TYPE: DNA
<213> ORGANISM: Homo sapiens

<400> SEQUENCE: 76
acagcaggca cagacaggca g                                               21

<210> SEQ ID NO 77
<211> LENGTH: 21
<212> TYPE: DNA
<213> ORGANISM: Homo sapiens

<400> SEQUENCE: 77
atgacctatg aattgacaga c                                               21

<210> SEQ ID NO 78
<211> LENGTH: 21
<212> TYPE: DNA
<213> ORGANISM: Homo sapiens

<400> SEQUENCE: 78
taatctcagc tggcaactgt g                                               21

<210> SEQ ID NO 79
<211> LENGTH: 24
<212> TYPE: DNA
<213> ORGANISM: Homo sapiens

<400> SEQUENCE: 79
```

```
tactgcatca ggaactgatt ggat                                         24

<210> SEQ ID NO 80
<211> LENGTH: 21
<212> TYPE: DNA
<213> ORGANISM: Homo sapiens

<400> SEQUENCE: 80
ttgtgcttga tctaaccatg t                                            21

<210> SEQ ID NO 81
<211> LENGTH: 21
<212> TYPE: DNA
<213> ORGANISM: Homo sapiens

<400> SEQUENCE: 81
tgattgtcca aacgcaattc t                                            21

<210> SEQ ID NO 82
<211> LENGTH: 21
<212> TYPE: DNA
<213> ORGANISM: Homo sapiens

<400> SEQUENCE: 82
ccacaccgta tctgacactt t                                            21

<210> SEQ ID NO 83
<211> LENGTH: 23
<212> TYPE: DNA
<213> ORGANISM: Homo sapiens

<400> SEQUENCE: 83
agctacattg tctgctgggt ttc                                          23

<210> SEQ ID NO 84
<211> LENGTH: 24
<212> TYPE: DNA
<213> ORGANISM: Homo sapiens

<400> SEQUENCE: 84
agctacatct ggctactggg tctc                                         24

<210> SEQ ID NO 85
<211> LENGTH: 21
<212> TYPE: DNA
<213> ORGANISM: Homo sapiens

<400> SEQUENCE: 85
tgtcagtttg tcaaataccc c                                            21

<210> SEQ ID NO 86
<211> LENGTH: 23
<212> TYPE: DNA
<213> ORGANISM: Homo sapiens

<400> SEQUENCE: 86
caagtcacta gtggttccgt tta                                          23

<210> SEQ ID NO 87
<211> LENGTH: 23
<212> TYPE: DNA
<213> ORGANISM: Homo sapiens

<400> SEQUENCE: 87
```

```
taatactgcc tggtaatgat gac                                              23

<210> SEQ ID NO 88
<211> LENGTH: 21
<212> TYPE: DNA
<213> ORGANISM: Homo sapiens

<400> SEQUENCE: 88
tgaggtagta gtttgtacag t                                                21

<210> SEQ ID NO 89
<211> LENGTH: 21
<212> TYPE: DNA
<213> ORGANISM: Homo sapiens

<400> SEQUENCE: 89
tgaggtagta gtttgtgctg t                                                21

<210> SEQ ID NO 90
<211> LENGTH: 21
<212> TYPE: DNA
<213> ORGANISM: Homo sapiens

<400> SEQUENCE: 90
tggaatgtaa agaagtatgt a                                                21

<210> SEQ ID NO 91
<211> LENGTH: 22
<212> TYPE: DNA
<213> ORGANISM: Homo sapiens

<400> SEQUENCE: 91
tagcagcaca tcatggttta ca                                               22

<210> SEQ ID NO 92
<211> LENGTH: 21
<212> TYPE: DNA
<213> ORGANISM: Homo sapiens

<400> SEQUENCE: 92
atcacattgc cagggattac c                                                21

<210> SEQ ID NO 93
<211> LENGTH: 21
<212> TYPE: DNA
<213> ORGANISM: Homo sapiens

<400> SEQUENCE: 93
ttcacagtgg ctaagttctg c                                                21

<210> SEQ ID NO 94
<211> LENGTH: 22
<212> TYPE: DNA
<213> ORGANISM: Homo sapiens

<400> SEQUENCE: 94
tgtaaacatc ctacactcag ct                                               22

<210> SEQ ID NO 95
<211> LENGTH: 23
<212> TYPE: DNA
<213> ORGANISM: Homo sapiens
```

<400> SEQUENCE: 95
tggagtgtga caatggtgtt tgt                                              23

<210> SEQ ID NO 96
<211> LENGTH: 22
<212> TYPE: DNA
<213> ORGANISM: Homo sapiens

<400> SEQUENCE: 96
ttaaggcacg cggtgaatgc ca                                               22

<210> SEQ ID NO 97
<211> LENGTH: 22
<212> TYPE: DNA
<213> ORGANISM: Homo sapiens

<400> SEQUENCE: 97
tccctgagac cctaacttgt ga                                               22

<210> SEQ ID NO 98
<211> LENGTH: 22
<212> TYPE: DNA
<213> ORGANISM: Homo sapiens

<400> SEQUENCE: 98
tcacagtgaa ccggtctctt tt                                               22

<210> SEQ ID NO 99
<211> LENGTH: 22
<212> TYPE: DNA
<213> ORGANISM: Homo sapiens

<400> SEQUENCE: 99
cagtgcaatg ttaaagggc at                                                22

<210> SEQ ID NO 100
<211> LENGTH: 22
<212> TYPE: DNA
<213> ORGANISM: Homo sapiens

<400> SEQUENCE: 100
taacagtcta cagccatggt cg                                               22

<210> SEQ ID NO 101
<211> LENGTH: 22
<212> TYPE: DNA
<213> ORGANISM: Homo sapiens

<400> SEQUENCE: 101
ttggtcccct tcaaccagct gt                                               22

<210> SEQ ID NO 102
<211> LENGTH: 23
<212> TYPE: DNA
<213> ORGANISM: Homo sapiens

<400> SEQUENCE: 102
tatggctttt tattcctatg tga                                              23

<210> SEQ ID NO 103
<211> LENGTH: 22
<212> TYPE: DNA
<213> ORGANISM: Homo sapiens

```
<400> SEQUENCE: 103
tattgcttaa gaatacgcgt ag                                        22

<210> SEQ ID NO 104
<211> LENGTH: 17
<212> TYPE: DNA
<213> ORGANISM: Homo sapiens

<400> SEQUENCE: 104
agctggtgtt gtgaatc                                              17

<210> SEQ ID NO 105
<211> LENGTH: 21
<212> TYPE: DNA
<213> ORGANISM: Homo sapiens

<400> SEQUENCE: 105
agtggtttta ccctatggta g                                         21

<210> SEQ ID NO 106
<211> LENGTH: 22
<212> TYPE: DNA
<213> ORGANISM: Homo sapiens

<400> SEQUENCE: 106
taacactgtc tggtaaagat gg                                        22

<210> SEQ ID NO 107
<211> LENGTH: 20
<212> TYPE: DNA
<213> ORGANISM: Homo sapiens

<400> SEQUENCE: 107
cataaagtag aaagcactac                                           20

<210> SEQ ID NO 108
<211> LENGTH: 23
<212> TYPE: DNA
<213> ORGANISM: Homo sapiens

<400> SEQUENCE: 108
tgtagtgttt cctactttat gga                                       23

<210> SEQ ID NO 109
<211> LENGTH: 22
<212> TYPE: DNA
<213> ORGANISM: Homo sapiens

<400> SEQUENCE: 109
tgagatgaag cactgtagct ca                                        22

<210> SEQ ID NO 110
<211> LENGTH: 22
<212> TYPE: DNA
<213> ORGANISM: Homo sapiens

<400> SEQUENCE: 110
tacagtatag atgatgtact ag                                        22

<210> SEQ ID NO 111
<211> LENGTH: 24
<212> TYPE: DNA
```

<213> ORGANISM: Homo sapiens

<400> SEQUENCE: 111
gtccagtttt cccaggaatc cctt 24

<210> SEQ ID NO 112
<211> LENGTH: 22
<212> TYPE: DNA
<213> ORGANISM: Homo sapiens

<400> SEQUENCE: 112
tcagtgcatg acagaacttg gg 22

<210> SEQ ID NO 113
<211> LENGTH: 20
<212> TYPE: DNA
<213> ORGANISM: Homo sapiens

<400> SEQUENCE: 113
ttgcatagtc acaaaagtga 20

<210> SEQ ID NO 114
<211> LENGTH: 22
<212> TYPE: DNA
<213> ORGANISM: Homo sapiens

<400> SEQUENCE: 114
caacggaatc ccaaaagcag ct 22

<210> SEQ ID NO 115
<211> LENGTH: 22
<212> TYPE: DNA
<213> ORGANISM: Homo sapiens

<400> SEQUENCE: 115
gctgcgcttg gatttcgtcc cc 22

<210> SEQ ID NO 116
<211> LENGTH: 23
<212> TYPE: DNA
<213> ORGANISM: Homo sapiens

<400> SEQUENCE: 116
tctttggtta tctagctgta tga 23

<210> SEQ ID NO 117
<211> LENGTH: 21
<212> TYPE: DNA
<213> ORGANISM: Homo sapiens

<400> SEQUENCE: 117
taaagctaga taaccgaaag t 21

<210> SEQ ID NO 118
<211> LENGTH: 23
<212> TYPE: DNA
<213> ORGANISM: Homo sapiens

<400> SEQUENCE: 118
tccctgagac cctttaacct gtg 23

<210> SEQ ID NO 119
<211> LENGTH: 21

<212> TYPE: DNA
<213> ORGANISM: Homo sapiens

<400> SEQUENCE: 119
cattattact tttggtacgc g                                              21

<210> SEQ ID NO 120
<211> LENGTH: 21
<212> TYPE: DNA
<213> ORGANISM: Homo sapiens

<400> SEQUENCE: 120
tcgtaccgtg agtaataatg c                                              21

<210> SEQ ID NO 121
<211> LENGTH: 22
<212> TYPE: DNA
<213> ORGANISM: Homo sapiens

<400> SEQUENCE: 121
tcggatccgt ctgagcttgg ct                                             22

<210> SEQ ID NO 122
<211> LENGTH: 21
<212> TYPE: DNA
<213> ORGANISM: Homo sapiens

<400> SEQUENCE: 122
tgtgactggt tgaccagagg g                                              21

<210> SEQ ID NO 123
<211> LENGTH: 23
<212> TYPE: DNA
<213> ORGANISM: Homo sapiens

<400> SEQUENCE: 123
actccatttg ttttgatgat gga                                            23

<210> SEQ ID NO 124
<211> LENGTH: 22
<212> TYPE: DNA
<213> ORGANISM: Homo sapiens

<400> SEQUENCE: 124
tgagaactga attccatggg tt                                             22

<210> SEQ ID NO 125
<211> LENGTH: 22
<212> TYPE: DNA
<213> ORGANISM: Homo sapiens

<400> SEQUENCE: 125
tctggctccg tgtcttcact cc                                             22

<210> SEQ ID NO 126
<211> LENGTH: 22
<212> TYPE: DNA
<213> ORGANISM: Homo sapiens

<400> SEQUENCE: 126
tctcccaacc cttgtaccag tg                                             22

<210> SEQ ID NO 127

```
<211> LENGTH: 22
<212> TYPE: DNA
<213> ORGANISM: Homo sapiens

<400> SEQUENCE: 127
taggttatcc gtgttgcctt cg                                              22

<210> SEQ ID NO 128
<211> LENGTH: 22
<212> TYPE: DNA
<213> ORGANISM: Homo sapiens

<400> SEQUENCE: 128
aatcatacac ggttgaccta tt                                              22

<210> SEQ ID NO 129
<211> LENGTH: 22
<212> TYPE: DNA
<213> ORGANISM: Homo sapiens

<400> SEQUENCE: 129
tggacggaga actgataagg gt                                              22

<210> SEQ ID NO 130
<211> LENGTH: 18
<212> TYPE: DNA
<213> ORGANISM: Homo sapiens

<400> SEQUENCE: 130
tggagagaaa ggcagttc                                                   18

<210> SEQ ID NO 131
<211> LENGTH: 23
<212> TYPE: DNA
<213> ORGANISM: Homo sapiens

<400> SEQUENCE: 131
caaagaattc tcctttggg ctt                                              23

<210> SEQ ID NO 132
<211> LENGTH: 22
<212> TYPE: DNA
<213> ORGANISM: Homo sapiens

<400> SEQUENCE: 132
catcccttgc atggtggagg gt                                              22

<210> SEQ ID NO 133
<211> LENGTH: 22
<212> TYPE: DNA
<213> ORGANISM: Homo sapiens

<400> SEQUENCE: 133
tgatatgttt gatatattag gt                                              22

<210> SEQ ID NO 134
<211> LENGTH: 21
<212> TYPE: DNA
<213> ORGANISM: Homo sapiens

<400> SEQUENCE: 134
aactggccta caaagtccca g                                               21
```

```
<210> SEQ ID NO 135
<211> LENGTH: 22
<212> TYPE: DNA
<213> ORGANISM: Homo sapiens

<400> SEQUENCE: 135
tgtaacagca actccatgtg ga                                              22

<210> SEQ ID NO 136
<211> LENGTH: 21
<212> TYPE: DNA
<213> ORGANISM: Homo sapiens

<400> SEQUENCE: 136
tagcagcaca gaaatattgg c                                               21

<210> SEQ ID NO 137
<211> LENGTH: 22
<212> TYPE: DNA
<213> ORGANISM: Homo sapiens

<400> SEQUENCE: 137
tggaatgtaa ggaagtgtgt gg                                              22

<210> SEQ ID NO 138
<211> LENGTH: 23
<212> TYPE: DNA
<213> ORGANISM: Homo sapiens

<400> SEQUENCE: 138
aaaagctggg ttgagagggc gaa                                             23

<210> SEQ ID NO 139
<211> LENGTH: 22
<212> TYPE: DNA
<213> ORGANISM: Homo sapiens

<400> SEQUENCE: 139
taatactgcc gggtaatgat gg                                              22

<210> SEQ ID NO 140
<211> LENGTH: 22
<212> TYPE: DNA
<213> ORGANISM: Homo sapiens

<400> SEQUENCE: 140
ttaatgctaa tcgtgatagg gg                                              22

<210> SEQ ID NO 141
<211> LENGTH: 22
<212> TYPE: DNA
<213> ORGANISM: Homo sapiens

<400> SEQUENCE: 141
tcacagtgaa ccggtctctt tc                                              22

<210> SEQ ID NO 142
<211> LENGTH: 21
<212> TYPE: DNA
<213> ORGANISM: Homo sapiens

<400> SEQUENCE: 142
taaagtgctg acagtgcaga t                                               21
```

<210> SEQ ID NO 143
<211> LENGTH: 20
<212> TYPE: DNA
<213> ORGANISM: Homo sapiens

<400> SEQUENCE: 143
tagcaccatt tgaaatcggt                                            20

<210> SEQ ID NO 144
<211> LENGTH: 22
<212> TYPE: DNA
<213> ORGANISM: Homo sapiens

<400> SEQUENCE: 144
catcttaccg gacagtgctg ga                                         22

<210> SEQ ID NO 145
<211> LENGTH: 22
<212> TYPE: DNA
<213> ORGANISM: Homo sapiens

<400> SEQUENCE: 145
taacactgtc tggtaacgat gt                                         22

<210> SEQ ID NO 146
<211> LENGTH: 22
<212> TYPE: DNA
<213> ORGANISM: Homo sapiens

<400> SEQUENCE: 146
taaacgtgga tgtacttgct tt                                         22

<210> SEQ ID NO 147
<211> LENGTH: 23
<212> TYPE: DNA
<213> ORGANISM: Homo sapiens

<400> SEQUENCE: 147
taagtgcttc catgttttgg tga                                        23

<210> SEQ ID NO 148
<211> LENGTH: 23
<212> TYPE: DNA
<213> ORGANISM: Homo sapiens

<400> SEQUENCE: 148
taggcagtgt cattagctga ttg                                        23

<210> SEQ ID NO 149
<211> LENGTH: 23
<212> TYPE: DNA
<213> ORGANISM: Homo sapiens

<400> SEQUENCE: 149
aggcagtgta gttagctgat tgc                                        23

<210> SEQ ID NO 150
<211> LENGTH: 22
<212> TYPE: DNA
<213> ORGANISM: Homo sapiens

<400> SEQUENCE: 150
tggtttaccg tcccacatac at                                         22

```
<210> SEQ ID NO 151
<211> LENGTH: 22
<212> TYPE: DNA
<213> ORGANISM: Homo sapiens

<400> SEQUENCE: 151
tatgtgggat ggtaaaccgc tt                                              22

<210> SEQ ID NO 152
<211> LENGTH: 23
<212> TYPE: DNA
<213> ORGANISM: Homo sapiens

<400> SEQUENCE: 152
cagtgcaata gtattgtcaa agc                                             23

<210> SEQ ID NO 153
<211> LENGTH: 22
<212> TYPE: DNA
<213> ORGANISM: Homo sapiens

<400> SEQUENCE: 153
cacccgtaga accgaccttg cg                                              22

<210> SEQ ID NO 154
<211> LENGTH: 21
<212> TYPE: DNA
<213> ORGANISM: Homo sapiens

<400> SEQUENCE: 154
agggcccccc ctcaatcctg t                                               21

<210> SEQ ID NO 155
<211> LENGTH: 22
<212> TYPE: DNA
<213> ORGANISM: Homo sapiens

<400> SEQUENCE: 155
cagtgcaatg atgaaagggc at                                              22

<210> SEQ ID NO 156
<211> LENGTH: 20
<212> TYPE: DNA
<213> ORGANISM: Homo sapiens

<400> SEQUENCE: 156
tgtaaacatc cttgactgga                                                 20

<210> SEQ ID NO 157
<211> LENGTH: 22
<212> TYPE: DNA
<213> ORGANISM: Homo sapiens

<400> SEQUENCE: 157
ctttcagtcg gatgtttaca gc                                              22

<210> SEQ ID NO 158
<211> LENGTH: 22
<212> TYPE: DNA
<213> ORGANISM: Homo sapiens

<400> SEQUENCE: 158
```
ttatcagaat ctccaggggt ac                                                    22

<210> SEQ ID NO 159
<211> LENGTH: 23
<212> TYPE: DNA
<213> ORGANISM: Homo sapiens

<400> SEQUENCE: 159
aatccttgga acctaggtgt gag                                                   23

<210> SEQ ID NO 160
<211> LENGTH: 22
<212> TYPE: DNA
<213> ORGANISM: Homo sapiens

<400> SEQUENCE: 160
attgcacggt atccatctgt aa                                                    22

<210> SEQ ID NO 161
<211> LENGTH: 22
<212> TYPE: DNA
<213> ORGANISM: Homo sapiens

<400> SEQUENCE: 161
taatgcccct aaaaatcctt at                                                    22

<210> SEQ ID NO 162
<211> LENGTH: 23
<212> TYPE: DNA
<213> ORGANISM: Homo sapiens

<400> SEQUENCE: 162
actttaacat ggaagtgctt tct                                                   23

<210> SEQ ID NO 163
<211> LENGTH: 23
<212> TYPE: DNA
<213> ORGANISM: Homo sapiens

<400> SEQUENCE: 163
taagtgcttc catgttttag tag                                                   23

<210> SEQ ID NO 164
<211> LENGTH: 22
<212> TYPE: DNA
<213> ORGANISM: Homo sapiens

<400> SEQUENCE: 164
tttaacatgg gggtacctgc tg                                                    22

<210> SEQ ID NO 165
<211> LENGTH: 23
<212> TYPE: DNA
<213> ORGANISM: Homo sapiens

<400> SEQUENCE: 165
taagtgcttc catgtttcag tgg                                                   23

<210> SEQ ID NO 166
<211> LENGTH: 23
<212> TYPE: DNA
<213> ORGANISM: Homo sapiens

<400> SEQUENCE: 166

```
taagtgcttc catgtttgag tgt                                          23
```

<210> SEQ ID NO 167
<211> LENGTH: 22
<212> TYPE: DNA
<213> ORGANISM: Homo sapiens

<400> SEQUENCE: 167

```
aattgcactt tagcaatggt ga                                           22
```

<210> SEQ ID NO 168
<211> LENGTH: 22
<212> TYPE: DNA
<213> ORGANISM: Homo sapiens

<400> SEQUENCE: 168

```
acatagagga aattccacgt tt                                           22
```

<210> SEQ ID NO 169
<211> LENGTH: 22
<212> TYPE: DNA
<213> ORGANISM: Homo sapiens

<400> SEQUENCE: 169

```
agatcgaccg tgttatattc gc                                           22
```

<210> SEQ ID NO 170
<211> LENGTH: 21
<212> TYPE: DNA
<213> ORGANISM: Homo sapiens

<400> SEQUENCE: 170

```
aataatacat ggttgatctt t                                            21
```

<210> SEQ ID NO 171
<211> LENGTH: 21
<212> TYPE: DNA
<213> ORGANISM: Homo sapiens

<400> SEQUENCE: 171

```
gcctgctggg gtggaacctg g                                            21
```

<210> SEQ ID NO 172
<211> LENGTH: 21
<212> TYPE: DNA
<213> ORGANISM: Homo sapiens

<400> SEQUENCE: 172

```
gtgccgccat cttttgagtg t                                            21
```

<210> SEQ ID NO 173
<211> LENGTH: 23
<212> TYPE: DNA
<213> ORGANISM: Homo sapiens

<400> SEQUENCE: 173

```
aaagtgctgc gacatttgag cgt                                          23
```

<210> SEQ ID NO 174
<211> LENGTH: 22
<212> TYPE: DNA
<213> ORGANISM: Homo sapiens

<400> SEQUENCE: 174
actcaaaatg ggggcgcttt cc                    22

<210> SEQ ID NO 175
<211> LENGTH: 23
<212> TYPE: DNA
<213> ORGANISM: Homo sapiens

<400> SEQUENCE: 175
gaagtgcttc gattttgggg tgt                   23

<210> SEQ ID NO 176
<211> LENGTH: 22
<212> TYPE: DNA
<213> ORGANISM: Homo sapiens

<400> SEQUENCE: 176
ttataataca acctgataag tg                    22

<210> SEQ ID NO 177
<211> LENGTH: 22
<212> TYPE: DNA
<213> ORGANISM: Homo sapiens

<400> SEQUENCE: 177
tttgttcgtt cggctcgcgt ga                    22

<210> SEQ ID NO 178
<211> LENGTH: 21
<212> TYPE: DNA
<213> ORGANISM: Homo sapiens

<400> SEQUENCE: 178
atcatagagg aaaatccacg t                     21

<210> SEQ ID NO 179
<211> LENGTH: 22
<212> TYPE: DNA
<213> ORGANISM: Homo sapiens

<400> SEQUENCE: 179
atcacacaaa ggcaactttt gt                    22

<210> SEQ ID NO 180
<211> LENGTH: 22
<212> TYPE: DNA
<213> ORGANISM: Homo sapiens

<400> SEQUENCE: 180
ctcctgactc caggtcctgt gt                    22

<210> SEQ ID NO 181
<211> LENGTH: 22
<212> TYPE: DNA
<213> ORGANISM: Homo sapiens

<400> SEQUENCE: 181
ctggacttgg agtcagaagg cc                    22

<210> SEQ ID NO 182
<211> LENGTH: 19
<212> TYPE: DNA
<213> ORGANISM: Homo sapiens

```
<400> SEQUENCE: 182
tggtagacta tggaacgta                                              19

<210> SEQ ID NO 183
<211> LENGTH: 22
<212> TYPE: DNA
<213> ORGANISM: Homo sapiens

<400> SEQUENCE: 183
tggttgacca tagaacatgc gc                                          22

<210> SEQ ID NO 184
<211> LENGTH: 22
<212> TYPE: DNA
<213> ORGANISM: Homo sapiens

<400> SEQUENCE: 184
tatgtaatat ggtccacatc tt                                          22

<210> SEQ ID NO 185
<211> LENGTH: 22
<212> TYPE: DNA
<213> ORGANISM: Homo sapiens

<400> SEQUENCE: 185
tatacaaggg caagctctct gt                                          22

<210> SEQ ID NO 186
<211> LENGTH: 22
<212> TYPE: DNA
<213> ORGANISM: Homo sapiens

<400> SEQUENCE: 186
gaagttgttc gtggtggatt cg                                          22

<210> SEQ ID NO 187
<211> LENGTH: 22
<212> TYPE: DNA
<213> ORGANISM: Homo sapiens

<400> SEQUENCE: 187
agatcagaag gtgattgtgg ct                                          22

<210> SEQ ID NO 188
<211> LENGTH: 23
<212> TYPE: DNA
<213> ORGANISM: Homo sapiens

<400> SEQUENCE: 188
tccgtctcag ttactttata gcc                                         23

<210> SEQ ID NO 189
<211> LENGTH: 23
<212> TYPE: DNA
<213> ORGANISM: Homo sapiens

<400> SEQUENCE: 189
gcaaagcaca cggcctgcag aga                                         23

<210> SEQ ID NO 190
<211> LENGTH: 22
<212> TYPE: DNA
```

```
<213> ORGANISM: Homo sapiens

<400> SEQUENCE: 190
ctggccctct ctgcccttcc gt                                              22

<210> SEQ ID NO 191
<211> LENGTH: 24
<212> TYPE: DNA
<213> ORGANISM: Homo sapiens

<400> SEQUENCE: 191
tctcacacag aaatcgcacc cgtc                                            24

<210> SEQ ID NO 192
<211> LENGTH: 23
<212> TYPE: DNA
<213> ORGANISM: Homo sapiens

<400> SEQUENCE: 192
tccagctcct atatgatgcc ttt                                             23

<210> SEQ ID NO 193
<211> LENGTH: 22
<212> TYPE: DNA
<213> ORGANISM: Homo sapiens

<400> SEQUENCE: 193
gcacattaca cggtcgacct ct                                              22

<210> SEQ ID NO 194
<211> LENGTH: 20
<212> TYPE: DNA
<213> ORGANISM: Homo sapiens

<400> SEQUENCE: 194
cctctgggcc cttcctccag                                                 20

<210> SEQ ID NO 195
<211> LENGTH: 22
<212> TYPE: DNA
<213> ORGANISM: Homo sapiens

<400> SEQUENCE: 195
actagactga agctccttga gg                                              22

<210> SEQ ID NO 196
<211> LENGTH: 22
<212> TYPE: DNA
<213> ORGANISM: Homo sapiens

<400> SEQUENCE: 196
tatggctttt cattcctatg tg                                              22

<210> SEQ ID NO 197
<211> LENGTH: 22
<212> TYPE: DNA
<213> ORGANISM: Homo sapiens

<400> SEQUENCE: 197
tcagtgcatc acagaacttt gt                                              22

<210> SEQ ID NO 198
<211> LENGTH: 21
```

```
<212> TYPE: DNA
<213> ORGANISM: Homo sapiens

<400> SEQUENCE: 198
gcccctgggc ctatcctaga a                                              21

<210> SEQ ID NO 199
<211> LENGTH: 23
<212> TYPE: DNA
<213> ORGANISM: Homo sapiens

<400> SEQUENCE: 199
cgcatcccct agggcattgg tgt                                            23

<210> SEQ ID NO 200
<211> LENGTH: 22
<212> TYPE: DNA
<213> ORGANISM: Homo sapiens

<400> SEQUENCE: 200
ccactgcccc aggtgctgct gg                                             22

<210> SEQ ID NO 201
<211> LENGTH: 23
<212> TYPE: DNA
<213> ORGANISM: Homo sapiens

<400> SEQUENCE: 201
tccagcatca gtgattttgt tga                                            23

<210> SEQ ID NO 202
<211> LENGTH: 21
<212> TYPE: DNA
<213> ORGANISM: Homo sapiens

<400> SEQUENCE: 202
tccctgtcct ccaggagctc a                                              21

<210> SEQ ID NO 203
<211> LENGTH: 23
<212> TYPE: DNA
<213> ORGANISM: Homo sapiens

<400> SEQUENCE: 203
tcaagagcaa taacgaaaaa tgt                                            23

<210> SEQ ID NO 204
<211> LENGTH: 21
<212> TYPE: DNA
<213> ORGANISM: Homo sapiens

<400> SEQUENCE: 204 ttggtccect tcaaccagct a                                              21

<210> SEQ ID NO 205
<211> LENGTH: 23
<212> TYPE: DNA
<213> ORGANISM: Homo sapiens

<400> SEQUENCE: 205
cctagtaggt gtccagtaag tgt                                            23

<210> SEQ ID NO 206
```

```
<211> LENGTH: 21
<212> TYPE: DNA
<213> ORGANISM: Homo sapiens

<400> SEQUENCE: 206
tgctgactcc tagtccaggg c                                              21

<210> SEQ ID NO 207
<211> LENGTH: 23
<212> TYPE: DNA
<213> ORGANISM: Homo sapiens

<400> SEQUENCE: 207
tgtctgcccg catgcctgcc tct                                            23

<210> SEQ ID NO 208
<211> LENGTH: 20
<212> TYPE: DNA
<213> ORGANISM: Homo sapiens

<400> SEQUENCE: 208
attcctagaa attgttcata                                                20

<210> SEQ ID NO 209
<211> LENGTH: 21
<212> TYPE: DNA
<213> ORGANISM: Homo sapiens

<400> SEQUENCE: 209
taggtagttt cctgttgttg g                                              21

<210> SEQ ID NO 210
<211> LENGTH: 22
<212> TYPE: DNA
<213> ORGANISM: Homo sapiens

<400> SEQUENCE: 210
ctggacttag ggtcagaagg cc                                             22

<210> SEQ ID NO 211
<211> LENGTH: 22
<212> TYPE: DNA
<213> ORGANISM: Homo sapiens

<400> SEQUENCE: 211
agctcggtct gaggcccctc ag                                             22

<210> SEQ ID NO 212
<211> LENGTH: 22
<212> TYPE: DNA
<213> ORGANISM: Homo sapiens

<400> SEQUENCE: 212
cagcagcaat tcatgttttg aa                                             22

<210> SEQ ID NO 213
<211> LENGTH: 21
<212> TYPE: DNA
<213> ORGANISM: Homo sapiens

<400> SEQUENCE: 213
atcgggaatg tcgtgtccgc c                                              21
```

```
<210> SEQ ID NO 214
<211> LENGTH: 22
<212> TYPE: DNA
<213> ORGANISM: Homo sapiens

<400> SEQUENCE: 214
taaggtgcat ctagtgcagt ta                                              22

<210> SEQ ID NO 215
<211> LENGTH: 23
<212> TYPE: DNA
<213> ORGANISM: Homo sapiens

<400> SEQUENCE: 215
caaagtgctc atagtgcagg tag                                             23

<210> SEQ ID NO 216
<211> LENGTH: 22
<212> TYPE: DNA
<213> ORGANISM: Homo sapiens

<400> SEQUENCE: 216
ttgcatatgt aggatgtccc at                                              22

<210> SEQ ID NO 217
<211> LENGTH: 22
<212> TYPE: DNA
<213> ORGANISM: Homo sapiens

<400> SEQUENCE: 217
taatactgtc tggtaaaacc gt                                              22

<210> SEQ ID NO 218
<211> LENGTH: 22
<212> TYPE: DNA
<213> ORGANISM: Homo sapiens

<400> SEQUENCE: 218
tggcagtgta ttgttagctg gt                                              22

<210> SEQ ID NO 219
<211> LENGTH: 22
<212> TYPE: DNA
<213> ORGANISM: Homo sapiens

<400> SEQUENCE: 219
tttttgcgat gtgttcctaa ta                                              22

<210> SEQ ID NO 220
<211> LENGTH: 21
<212> TYPE: DNA
<213> ORGANISM: Homo sapiens

<400> SEQUENCE: 220
tgtcttgcag gccgtcatgc a                                               21

<210> SEQ ID NO 221
<211> LENGTH: 22
<212> TYPE: DNA
<213> ORGANISM: Homo sapiens

<400> SEQUENCE: 221
atcatgatgg gctcctcggt gt                                              22
```

```
<210> SEQ ID NO 222
<211> LENGTH: 22
<212> TYPE: DNA
<213> ORGANISM: Homo sapiens

<400> SEQUENCE: 222
aacacacctg gttaacctct tt                                              22

<210> SEQ ID NO 223
<211> LENGTH: 22
<212> TYPE: DNA
<213> ORGANISM: Homo sapiens

<400> SEQUENCE: 223
gaggttgtcc gtggtgagtt cg                                              22

<210> SEQ ID NO 224
<211> LENGTH: 23
<212> TYPE: DNA
<213> ORGANISM: Homo sapiens

<400> SEQUENCE: 224
aaaccgttac cattactgag ttt                                             23

<210> SEQ ID NO 225
<211> LENGTH: 22
<212> TYPE: DNA
<213> ORGANISM: Homo sapiens

<400> SEQUENCE: 225
tgtttgcaga ggaaactgag ac                                              22

<210> SEQ ID NO 226
<211> LENGTH: 21
<212> TYPE: DNA
<213> ORGANISM: Homo sapiens

<400> SEQUENCE: 226
tcagtctcat ctgcaaagaa g                                               21

<210> SEQ ID NO 227
<211> LENGTH: 22
<212> TYPE: DNA
<213> ORGANISM: Homo sapiens

<400> SEQUENCE: 227
aggttacccg agcaactttg ca                                              22

<210> SEQ ID NO 228
<211> LENGTH: 23
<212> TYPE: DNA
<213> ORGANISM: Homo sapiens

<400> SEQUENCE: 228
cgaatgttgc tcggtgaacc cct                                             23

<210> SEQ ID NO 229
<211> LENGTH: 23
<212> TYPE: DNA
<213> ORGANISM: Homo sapiens

<400> SEQUENCE: 229
acttcacctg gtccactagc cgt                                             23
```

```
<210> SEQ ID NO 230
<211> LENGTH: 22
<212> TYPE: DNA
<213> ORGANISM: Homo sapiens

<400> SEQUENCE: 230
aatataacac agatggcctg tt                                        22

<210> SEQ ID NO 231
<211> LENGTH: 22
<212> TYPE: DNA
<213> ORGANISM: Homo sapiens

<400> SEQUENCE: 231
atcatagagg aaaatccatg tt                                        22

<210> SEQ ID NO 232
<211> LENGTH: 22
<212> TYPE: DNA
<213> ORGANISM: Homo sapiens

<400> SEQUENCE: 232
agaggctggc cgtgatgaat tc                                        22

<210> SEQ ID NO 233
<211> LENGTH: 20
<212> TYPE: DNA
<213> ORGANISM: Homo sapiens

<400> SEQUENCE: 233
gtcatacacg gctctcctct                                           20

<210> SEQ ID NO 234
<211> LENGTH: 21
<212> TYPE: DNA
<213> ORGANISM: Homo sapiens

<400> SEQUENCE: 234
cccagataat ggcactctca a                                         21

<210> SEQ ID NO 235
<211> LENGTH: 23
<212> TYPE: DNA
<213> ORGANISM: Homo sapiens

<400> SEQUENCE: 235
agtgacatca catatacggc agc                                       23

<210> SEQ ID NO 236
<211> LENGTH: 22
<212> TYPE: DNA
<213> ORGANISM: Homo sapiens

<400> SEQUENCE: 236
caacctggag gactccatgc tg                                        22

<210> SEQ ID NO 237
<211> LENGTH: 23
<212> TYPE: DNA
<213> ORGANISM: Homo sapiens

<400> SEQUENCE: 237
```
agtggggaac ccttccatga gga          23

<210> SEQ ID NO 238
<211> LENGTH: 21
<212> TYPE: DNA
<213> ORGANISM: Homo sapiens

<400> SEQUENCE: 238
gtgtcttttg ctctgcagtc a            21

<210> SEQ ID NO 239
<211> LENGTH: 22
<212> TYPE: DNA
<213> ORGANISM: Homo sapiens

<400> SEQUENCE: 239
tgagaactga attccatagg ct           22

<210> SEQ ID NO 240
<211> LENGTH: 22
<212> TYPE: DNA
<213> ORGANISM: Homo sapiens

<400> SEQUENCE: 240
tttcctatgc atatacttct tt           22

<210> SEQ ID NO 241
<211> LENGTH: 22
<212> TYPE: DNA
<213> ORGANISM: Homo sapiens

<400> SEQUENCE: 241
agaggtatag ggcatgggaa aa           22

<210> SEQ ID NO 242
<211> LENGTH: 23
<212> TYPE: DNA
<213> ORGANISM: Homo sapiens

<400> SEQUENCE: 242
aggacctgcg ggacaagatt ctt          23

<210> SEQ ID NO 243
<211> LENGTH: 22
<212> TYPE: DNA
<213> ORGANISM: Homo sapiens

<400> SEQUENCE: 243
ttgtacatgg taggctttca tt           22

<210> SEQ ID NO 244
<211> LENGTH: 23
<212> TYPE: DNA
<213> ORGANISM: Homo sapiens

<400> SEQUENCE: 244
tcttggagta ggtcattggg tgg          23

<210> SEQ ID NO 245
<211> LENGTH: 21
<212> TYPE: DNA
<213> ORGANISM: Homo sapiens

<400> SEQUENCE: 245

```
ctggatggct cctccatgtc t                                      21

<210> SEQ ID NO 246
<211> LENGTH: 24
<212> TYPE: DNA
<213> ORGANISM: Homo sapiens

<400> SEQUENCE: 246
tgaaacatac acgggaaacc tctt                                   24

<210> SEQ ID NO 247
<211> LENGTH: 23
<212> TYPE: DNA
<213> ORGANISM: Homo sapiens

<400> SEQUENCE: 247
aaacaaacat ggtgcacttc ttt                                    23

<210> SEQ ID NO 248
<211> LENGTH: 17
<212> TYPE: DNA
<213> ORGANISM: Homo sapiens

<400> SEQUENCE: 248
attacatggc caatctc                                           17

<210> SEQ ID NO 249
<211> LENGTH: 24
<212> TYPE: DNA
<213> ORGANISM: Homo sapiens

<400> SEQUENCE: 249
aactggccct caaagtcccg cttt                                   24

<210> SEQ ID NO 250
<211> LENGTH: 21
<212> TYPE: DNA
<213> ORGANISM: Homo sapiens

<400> SEQUENCE: 250
cagcagcaca ctgtggtttg t                                      21

<210> SEQ ID NO 251
<211> LENGTH: 24
<212> TYPE: DNA
<213> ORGANISM: Homo sapiens

<400> SEQUENCE: 251
aacattcatt gttgtcggtg ggtt                                   24

<210> SEQ ID NO 252
<211> LENGTH: 23
<212> TYPE: DNA
<213> ORGANISM: Homo sapiens

<400> SEQUENCE: 252
cactcagcct tgagggcact ttc                                    23

<210> SEQ ID NO 253
<211> LENGTH: 22
<212> TYPE: DNA
<213> ORGANISM: Homo sapiens
```

```
<400> SEQUENCE: 253
aagtgctgtc atagctgagg tc                                            22

<210> SEQ ID NO 254
<211> LENGTH: 23
<212> TYPE: DNA
<213> ORGANISM: Homo sapiens

<400> SEQUENCE: 254
tttcaagcca gggggcgttt ttc                                           23

<210> SEQ ID NO 255
<211> LENGTH: 21
<212> TYPE: DNA
<213> ORGANISM: Homo sapiens

<400> SEQUENCE: 255
aaagtgcttc cttttttgagg g                                            21

<210> SEQ ID NO 256
<211> LENGTH: 24
<212> TYPE: DNA
<213> ORGANISM: Homo sapiens

<400> SEQUENCE: 256
ttctccaaaa gaaagcactt tctg                                          24

<210> SEQ ID NO 257
<211> LENGTH: 21
<212> TYPE: DNA
<213> ORGANISM: Homo sapiens

<400> SEQUENCE: 257
gagtgccttc ttttggagcg t                                             21

<210> SEQ ID NO 258
<211> LENGTH: 22
<212> TYPE: DNA
<213> ORGANISM: Homo sapiens

<400> SEQUENCE: 258
ttctccaaaa gggagcactt tc                                            22

<210> SEQ ID NO 259
<211> LENGTH: 22
<212> TYPE: DNA
<213> ORGANISM: Homo sapiens

<400> SEQUENCE: 259
aaagtgcctc cttttagagt gt                                            22

<210> SEQ ID NO 260
<211> LENGTH: 22
<212> TYPE: DNA
<213> ORGANISM: Homo sapiens

<400> SEQUENCE: 260
aagtgcttcc ttttagaggg tt                                            22

<210> SEQ ID NO 261
<211> LENGTH: 24
<212> TYPE: DNA
<213> ORGANISM: Homo sapiens
```

```
<400> SEQUENCE: 261
ctctagaggg aagcgctttc tgtt                                           24

<210> SEQ ID NO 262
<211> LENGTH: 22
<212> TYPE: DNA
<213> ORGANISM: Homo sapiens

<400> SEQUENCE: 262
aaagtgcatc tttttagagg at                                             22

<210> SEQ ID NO 263
<211> LENGTH: 22
<212> TYPE: DNA
<213> ORGANISM: Homo sapiens

<400> SEQUENCE: 263
aaagtgcatc tttttagagg at                                             22

<210> SEQ ID NO 264
<211> LENGTH: 22
<212> TYPE: DNA
<213> ORGANISM: Homo sapiens

<400> SEQUENCE: 264
aaagtgcttc cctttggact gt                                             22

<210> SEQ ID NO 265
<211> LENGTH: 24
<212> TYPE: DNA
<213> ORGANISM: Homo sapiens

<400> SEQUENCE: 265
ctcttgaggg aagcactttc tgtt                                           24

<210> SEQ ID NO 266
<211> LENGTH: 21
<212> TYPE: DNA
<213> ORGANISM: Homo sapiens

<400> SEQUENCE: 266
aaagtgcttc ctttagagg c                                               21

<210> SEQ ID NO 267
<211> LENGTH: 23
<212> TYPE: DNA
<213> ORGANISM: Homo sapiens

<400> SEQUENCE: 267
aaagtgcatc cttttagagg ttt                                            23

<210> SEQ ID NO 268
<211> LENGTH: 21
<212> TYPE: DNA
<213> ORGANISM: Homo sapiens

<400> SEQUENCE: 268
ctccagaggg atgcactttc t                                              21

<210> SEQ ID NO 269
<211> LENGTH: 21
<212> TYPE: DNA
```

```
<213> ORGANISM: Homo sapiens

<400> SEQUENCE: 269
gaaggcgctt ccctttagag c                                              21

<210> SEQ ID NO 270
<211> LENGTH: 21
<212> TYPE: DNA
<213> ORGANISM: Homo sapiens

<400> SEQUENCE: 270
aacgcgcttc cctatagagg g                                              21

<210> SEQ ID NO 271
<211> LENGTH: 23
<212> TYPE: DNA
<213> ORGANISM: Homo sapiens

<400> SEQUENCE: 271
ctctagaggg aagcactttc tct                                            23

<210> SEQ ID NO 272
<211> LENGTH: 21
<212> TYPE: DNA
<213> ORGANISM: Homo sapiens

<400> SEQUENCE: 272
aaagcgcttc tctttagagg a                                              21

<210> SEQ ID NO 273
<211> LENGTH: 21
<212> TYPE: DNA
<213> ORGANISM: Homo sapiens

<400> SEQUENCE: 273
aaagtgcttc cttttagagg g                                              21

<210> SEQ ID NO 274
<211> LENGTH: 22
<212> TYPE: DNA
<213> ORGANISM: Homo sapiens

<400> SEQUENCE: 274
caaagcgctc cccttagag gt                                              22

<210> SEQ ID NO 275
<211> LENGTH: 21
<212> TYPE: DNA
<213> ORGANISM: Homo sapiens

<400> SEQUENCE: 275
ctctagaggg aagcactttc t                                              21

<210> SEQ ID NO 276
<211> LENGTH: 23
<212> TYPE: DNA
<213> ORGANISM: Homo sapiens

<400> SEQUENCE: 276
aaagtgcttc cttttagagg gtt                                            23

<210> SEQ ID NO 277
<211> LENGTH: 23
```

<212> TYPE: DNA
<213> ORGANISM: Homo sapiens

<400> SEQUENCE: 277
tctctggagg gaagcacttt ctg                                              23

<210> SEQ ID NO 278
<211> LENGTH: 22
<212> TYPE: DNA
<213> ORGANISM: Homo sapiens

<400> SEQUENCE: 278
caaagcgctt ctctttagag tg                                               22

<210> SEQ ID NO 279
<211> LENGTH: 22
<212> TYPE: DNA
<213> ORGANISM: Homo sapiens

<400> SEQUENCE: 279
ctacaaaggg aagcactttc tc                                               22

<210> SEQ ID NO 280
<211> LENGTH: 21
<212> TYPE: DNA
<213> ORGANISM: Homo sapiens

<400> SEQUENCE: 280
gaaggcgctt ccctttggag t                                                21

<210> SEQ ID NO 281
<211> LENGTH: 22
<212> TYPE: DNA
<213> ORGANISM: Homo sapiens

<400> SEQUENCE: 281
cctctagatg gaagcactgt ct                                               22

<210> SEQ ID NO 282
<211> LENGTH: 23
<212> TYPE: DNA
<213> ORGANISM: Homo sapiens

<400> SEQUENCE: 282
atcgtgcatc cctttagagt gtt                                              23

<210> SEQ ID NO 283
<211> LENGTH: 23
<212> TYPE: DNA
<213> ORGANISM: Homo sapiens

<400> SEQUENCE: 283
caaagtgcct ccctttagag tgt                                              23

<210> SEQ ID NO 284
<211> LENGTH: 22
<212> TYPE: DNA
<213> ORGANISM: Homo sapiens

<400> SEQUENCE: 284
aacgcacttc cctttagagt gt                                               22

<210> SEQ ID NO 285

```
<211> LENGTH: 23
<212> TYPE: DNA
<213> ORGANISM: Homo sapiens

<400> SEQUENCE: 285
tctacaaagg gaagcccttt ctg                                           23

<210> SEQ ID NO 286
<211> LENGTH: 23
<212> TYPE: DNA
<213> ORGANISM: Homo sapiens

<400> SEQUENCE: 286
aaagtgcttc tctttggtgg gtt                                           23

<210> SEQ ID NO 287
<211> LENGTH: 22
<212> TYPE: DNA
<213> ORGANISM: Homo sapiens

<400> SEQUENCE: 287
tcgtgcatcc ctttagagtg tt                                            22

<210> SEQ ID NO 288
<211> LENGTH: 24
<212> TYPE: DNA
<213> ORGANISM: Homo sapiens

<400> SEQUENCE: 288
acaaagtgct tccctttaga gtgt                                          24

<210> SEQ ID NO 289
<211> LENGTH: 22
<212> TYPE: DNA
<213> ORGANISM: Homo sapiens

<400> SEQUENCE: 289
atctggaggt aagaagcact tt                                            22

<210> SEQ ID NO 290
<211> LENGTH: 18
<212> TYPE: DNA
<213> ORGANISM: Homo sapiens

<400> SEQUENCE: 290
tgcttccttt cagagggt                                                 18

<210> SEQ ID NO 291
<211> LENGTH: 22
<212> TYPE: DNA
<213> ORGANISM: Homo sapiens

<400> SEQUENCE: 291
aaagcgcttc ccttcagagt gt                                            22

<210> SEQ ID NO 292
<211> LENGTH: 21
<212> TYPE: DNA
<213> ORGANISM: Homo sapiens

<400> SEQUENCE: 292
ctgcaaaggg aagccctttc t                                             21
```

```
<210> SEQ ID NO 293
<211> LENGTH: 21
<212> TYPE: DNA
<213> ORGANISM: Homo sapiens

<400> SEQUENCE: 293
aaagcgcttc cctttgctgg a                                              21

<210> SEQ ID NO 294
<211> LENGTH: 21
<212> TYPE: DNA
<213> ORGANISM: Homo sapiens

<400> SEQUENCE: 294
caaagcgctt ccctttggag c                                              21

<210> SEQ ID NO 295
<211> LENGTH: 20
<212> TYPE: DNA
<213> ORGANISM: Homo sapiens

<400> SEQUENCE: 295
tctgcaaagg gaagcccttt                                                20

<210> SEQ ID NO 296
<211> LENGTH: 22
<212> TYPE: DNA
<213> ORGANISM: Homo sapiens

<400> SEQUENCE: 296
atcgtgcatc cttttagagt gt                                             22

<210> SEQ ID NO 297
<211> LENGTH: 22
<212> TYPE: DNA
<213> ORGANISM: Homo sapiens

<400> SEQUENCE: 297
acaaagtgct tcccttagta gt                                             22

<210> SEQ ID NO 298
<211> LENGTH: 23
<212> TYPE: DNA
<213> ORGANISM: Homo sapiens

<400> SEQUENCE: 298
aaaatggttc cctttagagt gtt                                            23

<210> SEQ ID NO 299
<211> LENGTH: 25
<212> TYPE: DNA
<213> ORGANISM: Homo sapiens

<400> SEQUENCE: 299
aaagtgcatc cttttagagt gttac                                          25

<210> SEQ ID NO 300
<211> LENGTH: 23
<212> TYPE: DNA
<213> ORGANISM: Homo sapiens

<400> SEQUENCE: 300
ttaagacttg cagtgatgtt taa                                            23
```

```
<210> SEQ ID NO 301
<211> LENGTH: 22
<212> TYPE: DNA
<213> ORGANISM: Homo sapiens

<400> SEQUENCE: 301
atgcacctgg gcaaggattc tg                                          22

<210> SEQ ID NO 302
<211> LENGTH: 22
<212> TYPE: DNA
<213> ORGANISM: Homo sapiens

<400> SEQUENCE: 302
aatcctttgt ccctgggtga ga                                          22

<210> SEQ ID NO 303
<211> LENGTH: 21
<212> TYPE: DNA
<213> ORGANISM: Homo sapiens

<400> SEQUENCE: 303
atccttgcta tctgggtgct a                                           21

<210> SEQ ID NO 304
<211> LENGTH: 23
<212> TYPE: DNA
<213> ORGANISM: Homo sapiens

<400> SEQUENCE: 304
tagcagcggg aacagttctg cag                                         23

<210> SEQ ID NO 305
<211> LENGTH: 21
<212> TYPE: DNA
<213> ORGANISM: Homo sapiens

<400> SEQUENCE: 305
agaccctggt ctgcactcta t                                           21

<210> SEQ ID NO 306
<211> LENGTH: 22
<212> TYPE: DNA
<213> ORGANISM: Homo sapiens

<400> SEQUENCE: 306
gtcaacactt gctggtttcc tc                                          22

<210> SEQ ID NO 307
<211> LENGTH: 22
<212> TYPE: DNA
<213> ORGANISM: Homo sapiens

<400> SEQUENCE: 307
ttcacaggga ggtgtcattt at                                          22

<210> SEQ ID NO 308
<211> LENGTH: 21
<212> TYPE: DNA
<213> ORGANISM: Homo sapiens

<400> SEQUENCE: 308
taaggcaccc ttctgagtag a                                           21
```

<210> SEQ ID NO 309
<211> LENGTH: 21
<212> TYPE: DNA
<213> ORGANISM: Homo sapiens

<400> SEQUENCE: 309
ttttgcacct tttggagtga a                                         21

<210> SEQ ID NO 310
<211> LENGTH: 23
<212> TYPE: DNA
<213> ORGANISM: Homo sapiens

<400> SEQUENCE: 310
tgattgtagc cttttggagt aga                                       23

<210> SEQ ID NO 311
<211> LENGTH: 23
<212> TYPE: DNA
<213> ORGANISM: Homo sapiens

<400> SEQUENCE: 311
tgattggtac gtctgtgggt aga                                       23

<210> SEQ ID NO 312
<211> LENGTH: 23
<212> TYPE: DNA
<213> ORGANISM: Homo sapiens

<400> SEQUENCE: 312
tactcaggag agtggcaatc aca                                       23

<210> SEQ ID NO 313
<211> LENGTH: 20
<212> TYPE: DNA
<213> ORGANISM: Homo sapiens

<400> SEQUENCE: 313
attgacactt ctgtgagtag                                           20

<210> SEQ ID NO 314
<211> LENGTH: 1474
<212> TYPE: DNA
<213> ORGANISM: Homo sapiens

<400> SEQUENCE: 314
atctgcaatc ccagagaatc ctgacaaagc gtgccaccct tttattttcc gtcaggtgcc    60
aggtcttagt taagattcac aatctttaga aagaatgaga ttcacaataa ttaactcttc   120
ctctcttctg ataaattccc catacctccc aatccaagta gcatctgtag ctacataacc   180 tatataccte cagcagctgg acatggggag gcgacagtcc tatctagaca tcatacacat   240
ttgccaagaa aggatctctg gggcttccgg gggtgagatt caagtaggac aataacaaga   300
ggctggacac cctacagatg tctttgatgt tttcagttgt ttgatatatc tccectgtag   360 ggcatgttga ggaaggagga gggctgatca aggccaagct ggtctagcct gacatcctag   420
ctcctgactg aacactatag acttcccagc agcatttcac ccagcagcca gagccggctt   480
taagtcccca acccttacag acaccactgc caccaccacc aaccacgacc accaccacca   540
ccaccactca ccaccatcat cacctccgga aagtgtagtc ctgccctaac ccaagtcacc   600

```
cccgacagta aatttacct  tcatgttgag aaagcttcct ggtgcttaat caagagctgg    660
agttcaatga gtcctagaca gtgagagggg cctgagcttc agctcaatgg aagcctgctg    720
tgtgccacaa gacggaaaag tggaagaagc tgcagtggga gacaaagcct cggtccccca    780
cccatccaca cacacctaca ctcacacacg cgcacatggg cgcgcacgaa ctaccattca    840
ggcagtcagt gggcaagagg aaagataagt aagtaccata cacacctaaa agatgagaga    900
attcatccag acatattaca gccagtttgg ggccctgac  tgcaatgtga aacctctcgc    960
tgctgctagg tttacaaaca gcccattgt  cctgtgcctc ctaatatcat ttgtactgaa   1020
gaccccatct ggggacttga gactttggtc ccagcccaga ctcctcagac ttttctctca   1080
gttgggatgc ttcactcgct gggggtgttt gtttgccctc tcatttttca gtacttctac   1140
agaattttct ctagagtcag tcattatgaa atgtacttcc ctccatctta acctatcaac   1200
tttctgcccc tccttcaagg cccagtataa atgccacctc ctccatgaag ccttccctaa   1260
ttccacccca aaccccacc  ttcaacaata tttcaacgct tctgcaatga tgaaaaagaa   1320
acatagttgt agtacttagc ctacctagac cagcaagcat tcattttag  ctcgctcatt   1380 ttttaccatg ttttccagtc tgtttaactt ctgcagtgcc ttcactacac tgccttacat   1440
aaaccaaatc acaataaagt tcatattcag taca                               1474

<210> SEQ ID NO 315
<211> LENGTH: 663
<212> TYPE: DNA
<213> ORGANISM: Homo sapiens

<400> SEQUENCE: 315
gcacctagtt ttctgaaaac tgatttacca ggtttaggtt gatgtcatct aatagtgcca     60 gaatttaat  gtttgaactt ctgttttttc taattatccc catttcttca atatcatttt    120
tgaggctttg gcagtcttca tttactacca cttgttcttt agccaaaagc tgattacata    180
tgatataaac agagaaatac ctttagaggt gactttaagg aaaatgaaga aaaagaacca    240
aaatgacttt attaaaataa tttccaagat tatttgtggc tcacctgaag gctttgcaaa    300
atttgtacca taaccgttta tttaacatat atttttattt ttgattgcac ttaaattttg    360
tataatttgt gtttcttttt ctgttctaca taaaatcaga aacttcaagc tctctaaata    420
aaatgaagga ctatatctag tggtatttca caatgaatat catgaactct caatgggtag    480
gtttcatcct acccattgcc actctgtttc ctgagagata cctcacattc caatgccaaa    540
catttctgca cagggaagct agaggtggat acacgtgttg caagtataaa agcatcactg    600
ggatttaagg agaattgaga gaatgtaccc acaaatggca gcaataataa atggatcaca    660
ctt                                                                  663

<210> SEQ ID NO 316
<211> LENGTH: 1832
<212> TYPE: DNA
<213> ORGANISM: Homo sapiens

<400> SEQUENCE: 316
cctgaccctc ctccactcca cctccaccca ctgtccgcct ctgcccgcag agcccacgcc     60
cgactagcag gcatgccgcg gtaggtaagg gccgccggac cgcgtagaga gccgggcccc    120
ggacggacgt tggttctgca ctaaaaccca tcttccccgg atgtgtgtct caccctcat     180 ccttttactt tttgccccett ccactttgag taccaaatcc acaagccatt ttttgaggag    240
agtgaaagag agtaccatgc tggcggcgca gagggaaggg gcctacaccc gtcttgggc     300
```

| | |
|---|---|
| tcgccccacc cagggctccc tcctggagca tcccaggcgg gcggcacgcc aacagccccc | 360 |
| cccttgaatc tgcagggagc aactctccac tccatattta tttaaacaat ttttttcccca | 420 |
| aaggcatcca tagtgcacta gcattttctt gaaccaataa tgtattaaaa ttttttgatg | 480 |
| tcagccttgc atcaagggct ttatcaaaaa gtacaataat aaatcctcag gtagtactgg | 540 |
| gaatggaagg cttttgccatg ggcctgctgc gtcagaccag tactgggaag gaggacggtt | 600 |
| gtaagcagtt gttatttagt gatattgtgg gtaacgtgag aagatagaac aatgctataa | 660 |
| tatataatga acacgtgggt atttaataag aaacatgatg tgagattact ttgtcccgct | 720 |
| tattctcctc cctgttatct gctagatcta gttctcaatc actgctcccc cgtgtgtatt | 780 |
| agaatgcatg taaggtcttc ttgtgtcctg atgaaaaata tgtgcttgaa atgagaaact | 840 |
| ttgatctctg cttactaatg tgccccatgt ccaagtccaa cctgcctgtg catgacctga | 900 |
| tcattacatg gctgtggttc ctaagcctgt tgctgaagtc attgtcgctc agcaataggg | 960 |
| tgcagttttc caggaatagg catttgccta attcctggca tgacactcta gtgacttcct | 1020 |
| ggtgaggccc agcctgtcct ggtacagcag ggtcttgctg taactcagac attccaaggg | 1080 |
| tatgggaagc catattcaca cctcacgctc tggacatgat ttagggaagc agggacaccc | 1140 |
| cccgccccc accttttggga tcagcctccg ccattccaag tcaacactct tcttgagcag | 1200 |
| accgtgattt ggaagagagg cacctgctgg aaaccacact tcttgaaaca gcctgggtga | 1260 |
| cggtccttta ggcagcctgc cgccgtctct gtcccggttc accttgccga gagaggcgcg | 1320 |
| tctgccccac cctcaaaccc tgtggggcct gatggtgctc acgactcttc ctgcaaaggg | 1380 |
| aactgaagac ctccacatta agtggctttt taacatgaaa aacacggcag ctgtagctcc | 1440 |
| cgagctactc tcttgccagc attttcacat tttgcctttc tcgtggtaga agccagtaca | 1500 |
| gagaaattct gtggtgggaa cattcgaggt gtcaccctgc agagctatgg tgaggtgtgg | 1560 |
| ataaggctta ggtgccaggc tgtaagcatt ctgagctggg cttgttgttt ttaagtcctg | 1620 |
| tatatgtatg tagtagtttg ggtgtgtata tatagtagca tttcaaaatg gacgtactgg | 1680 |
| tttaacctcc tatccttgga gagcagctgg ctctccacct tgttacacat tatgttagag | 1740 |
| aggtagcgag ctgctctgct atatgcctta agccaatatt tactcatcag gtcattattt | 1800 |
| tttacaatgg ccatggaata aaccattttt ac | 1832 |

<210> SEQ ID NO 317
<211> LENGTH: 957
<212> TYPE: DNA
<213> ORGANISM: Homo sapiens

<400> SEQUENCE: 317

| | |
|---|---|
| ggtcctgagg acaccgtgag ccagccaggc ctggccgctg ggcctgaccg gccccccagc | 60 |
| ccctacaccc cgcttctccc ggactctccc agcggacagc ccccagccc cacagcctga | 120 |
| gcctcccagc tgccatgtgc ctgttgcaca cctgcacaca cgccctggca cacatacaca | 180 |
| catgcgtgca ggcttgtgca gacactcagg gatggagctg ctgctgaagg gacttgtagg | 240 |
| gagaggctcg tcaacaagca ctgttctgga accttctctc cacgtggccc acaggcctga | 300 |
| ccacaggggc tgtgggtcct gcgtccccctt cctcgggtga gcctggcctg tcccgttcag | 360 |
| ccgttgggcc caggcttcct cccctccaag gtgaaacact gcagtcccgg tgtggtggct | 420 |
| ccccatgcag gacgggccag gctgggagtg ccgccttcct gtgccaaatt cagtggggac | 480 |
| tcagtgccca ggccctggcc acgagctttg gccttggtct acctgccagg ccaggcaaag | 540 |

| | |
|---|---|
| cgcctttaca caggcctcgg aaaacaatgg agtgagcaca agatgccctg tgcagctgcc | 600 |
| cgagggtctc cgcccacccc ggccggactt tgatccccc gaagtcttca caggcactgc | 660 |
| atcgggttgt ctggcgccct tttcctccag cctaaactga catcatccta tggactgagc | 720 |
| cggccactct ctggccgaag tggccgcagg ctgtgccccc gagctgcccc caccccctca | 780 |
| cagggtccct cagattatag gtgcccaggc tgaggtgaag aggcctgggg gccctgcctt | 840 |
| ccgggcgctc ctggaccctg ggcaaacct gtgacccttt tctactggaa tagaaatgag | 900 |
| ttttatcatc tttgaaaaat aattcactct tgaagtaata aacgtttaaa aaaatgg | 957 |

<210> SEQ ID NO 318
<211> LENGTH: 168
<212> TYPE: DNA
<213> ORGANISM: Homo sapiens

<400> SEQUENCE: 318

| | |
|---|---|
| atagttttca ggttaagaaa gccagaatct ttgttcagcc acactgactg aacagacttt | 60 |
| tagtggggtt acctggctaa cagcagcagc ggcaacggca gcagcagcag cagcagcagc | 120 |
| agcagcagca gcagggctcc tgggataact caggcatagt tcaacact | 168 |

<210> SEQ ID NO 319
<211> LENGTH: 106
<212> TYPE: DNA
<213> ORGANISM: Homo sapiens

<400> SEQUENCE: 319

| | |
|---|---|
| ctctcgcccc tactctttct ggtgttagat cgagctaccc tctaaaagca gtttagagtg | 60 |
| gtaaaaaaaa aaaaaaacac accaaacgct cgcagccaca aaggg | 106 |

<210> SEQ ID NO 320
<211> LENGTH: 174
<212> TYPE: DNA
<213> ORGANISM: Homo sapiens

<400> SEQUENCE: 320

| | |
|---|---|
| gtgatgcgta gttccggctg ccggttgaca tgaagaagca gcagcggcta gggcggcggt | 60 |
| agctgcaggg gtcggggatt gcagcgggcc tcggggctaa gagcgcgacg cggcctagag | 120 |
| cggcagacgg cgcagtgggc cgagaaggag gcgcagcagc cgccctggcc cgtc | 174 |

<210> SEQ ID NO 321
<211> LENGTH: 68
<212> TYPE: DNA
<213> ORGANISM: Homo sapiens

<400> SEQUENCE: 321

| | |
|---|---|
| gtcgccgtcc ccgtctcctg ccaggcgcgg agccctgcga gccgcgggtg ggccccaggc | 60 |
| gcgcagac | 68 |

<210> SEQ ID NO 322
<211> LENGTH: 23
<212> TYPE: DNA
<213> ORGANISM: Homo sapiens

<400> SEQUENCE: 322

| | |
|---|---|
| gcttcactcg ctgggggtgt ttg | 23 |

<210> SEQ ID NO 323
<211> LENGTH: 23

```
<212> TYPE: DNA
<213> ORGANISM: Homo sapiens

<400> SEQUENCE: 323
taagtgcttc catgtttgag tgt                                            23

<210> SEQ ID NO 324
<211> LENGTH: 23
<212> TYPE: DNA
<213> ORGANISM: Homo sapiens

<400> SEQUENCE: 324
taactcaggc atagttcaac act                                            23

<210> SEQ ID NO 325
<211> LENGTH: 23
<212> TYPE: DNA
<213> ORGANISM: Homo sapiens

<400> SEQUENCE: 325
taagtgcttc catgtttgag tgt                                            23

<210> SEQ ID NO 326
<211> LENGTH: 21
<212> TYPE: DNA
<213> ORGANISM: Homo sapiens

<400> SEQUENCE: 326
tcactcgctg ggggtgtttg t                                              21

<210> SEQ ID NO 327
<211> LENGTH: 21
<212> TYPE: DNA
<213> ORGANISM: Homo sapiens

<400> SEQUENCE: 327
taaggcaccc ttctgagtag a                                              21

<210> SEQ ID NO 328
<211> LENGTH: 21
<212> TYPE: DNA
<213> ORGANISM: Homo sapiens

<400> SEQUENCE: 328
tttgttcagc cacactgact g                                              21

<210> SEQ ID NO 329
<211> LENGTH: 21
<212> TYPE: DNA
<213> ORGANISM: Homo sapiens

<400> SEQUENCE: 329
taaggcaccc ttctgagtag a                                              21

<210> SEQ ID NO 330
<211> LENGTH: 22
<212> TYPE: DNA
<213> ORGANISM: Homo sapiens

<400> SEQUENCE: 330
cttcactcgc tgggggtgtt tg                                             22

<210> SEQ ID NO 331
```

```
<211> LENGTH: 22
<212> TYPE: DNA
<213> ORGANISM: Homo sapiens

<400> SEQUENCE: 331
aaagtgcttc cctttggact gt                                               22

<210> SEQ ID NO 332
<211> LENGTH: 13
<212> TYPE: DNA
<213> ORGANISM: Homo sapiens

<400> SEQUENCE: 332
atagttcaac act                                                         13

<210> SEQ ID NO 333
<211> LENGTH: 22
<212> TYPE: DNA
<213> ORGANISM: Homo sapiens

<400> SEQUENCE: 333
aaagtgcttc cctttggact gt                                               22

<210> SEQ ID NO 334
<211> LENGTH: 21
<212> TYPE: DNA
<213> ORGANISM: Homo sapiens

<400> SEQUENCE: 334
ttcactcgct gggggtgttt g                                                21

<210> SEQ ID NO 335
<211> LENGTH: 21
<212> TYPE: DNA
<213> ORGANISM: Homo sapiens

<400> SEQUENCE: 335
aaagcgcttc cctttgctgg a                                                21

<210> SEQ ID NO 336
<211> LENGTH: 21
<212> TYPE: DNA
<213> ORGANISM: Homo sapiens

<400> SEQUENCE: 336
tttagtgggg ttacctggct a                                                21

<210> SEQ ID NO 337
<211> LENGTH: 21
<212> TYPE: DNA
<213> ORGANISM: Homo sapiens

<400> SEQUENCE: 337
aaagcgcttc cctttgctgg a                                                21

<210> SEQ ID NO 338
<211> LENGTH: 22
<212> TYPE: DNA
<213> ORGANISM: Homo sapiens

<400> SEQUENCE: 338
aaaactgatt taccaggttt ag                                               22
```

```
<210> SEQ ID NO 339
<211> LENGTH: 22
<212> TYPE: DNA
<213> ORGANISM: Homo sapiens

<400> SEQUENCE: 339
ctggacttgg agtcagaagg cc                                              22

<210> SEQ ID NO 340
<211> LENGTH: 22
<212> TYPE: DNA
<213> ORGANISM: Homo sapiens

<400> SEQUENCE: 340
ctctttctgg tgttagatcg ag                                              22

<210> SEQ ID NO 341
<211> LENGTH: 22
<212> TYPE: DNA
<213> ORGANISM: Homo sapiens

<400> SEQUENCE: 341
ctggacttgg agtcagaagg cc                                              22

<210> SEQ ID NO 342
<211> LENGTH: 23
<212> TYPE: DNA
<213> ORGANISM: Homo sapiens

<400> SEQUENCE: 342
cttgttacac attatgttag aga                                             23

<210> SEQ ID NO 343
<211> LENGTH: 23
<212> TYPE: DNA
<213> ORGANISM: Homo sapiens

<400> SEQUENCE: 343
actttaacat ggaagtgctt tct                                             23

<210> SEQ ID NO 344
<211> LENGTH: 23
<212> TYPE: DNA
<213> ORGANISM: Homo sapiens

<400> SEQUENCE: 344
aggaggcgca gcagccgccc tgg                                             23

<210> SEQ ID NO 345
<211> LENGTH: 23
<212> TYPE: DNA
<213> ORGANISM: Homo sapiens

<400> SEQUENCE: 345
actttaacat ggaagtgctt tct                                             23

<210> SEQ ID NO 346
<211> LENGTH: 21
<212> TYPE: DNA
<213> ORGANISM: Homo sapiens

<400> SEQUENCE: 346
ttgtaagcag ttgttattta g                                               21
```

```
<210> SEQ ID NO 347
<211> LENGTH: 21
<212> TYPE: DNA
<213> ORGANISM: Homo sapiens

<400> SEQUENCE: 347
tgaggtagta gtttgtgctg t                                              21

<210> SEQ ID NO 348
<211> LENGTH: 21
<212> TYPE: DNA
<213> ORGANISM: Homo sapiens

<400> SEQUENCE: 348
tgagctgggc ttgttgtttt t                                              21

<210> SEQ ID NO 349
<211> LENGTH: 21
<212> TYPE: DNA
<213> ORGANISM: Homo sapiens

<400> SEQUENCE: 349
tgaggtagta gtttgtgctg t                                              21

<210> SEQ ID NO 350
<211> LENGTH: 21
<212> TYPE: DNA
<213> ORGANISM: Homo sapiens

<400> SEQUENCE: 350
acatgatgtg agattacttt g                                              21

<210> SEQ ID NO 351
<211> LENGTH: 21
<212> TYPE: DNA
<213> ORGANISM: Homo sapiens

<400> SEQUENCE: 351
tgaggtagta gtttgtgctg t                                              21

<210> SEQ ID NO 352
<211> LENGTH: 21
<212> TYPE: DNA
<213> ORGANISM: Homo sapiens

<400> SEQUENCE: 352
attctcctcc ctgttatctg c                                              21

<210> SEQ ID NO 353
<211> LENGTH: 21
<212> TYPE: DNA
<213> ORGANISM: Homo sapiens

<400> SEQUENCE: 353
tgaggtagta gtttgtgctg t                                              21

<210> SEQ ID NO 354
<211> LENGTH: 21
<212> TYPE: DNA
<213> ORGANISM: Homo sapiens

<400> SEQUENCE: 354
acggcgcagt gggccgagaa g                                              21
```

```
<210> SEQ ID NO 355
<211> LENGTH: 21
<212> TYPE: DNA
<213> ORGANISM: Homo sapiens

<400> SEQUENCE: 355
tgaggtagta gtttgtgctg t                                              21

<210> SEQ ID NO 356
<211> LENGTH: 21
<212> TYPE: DNA
<213> ORGANISM: Homo sapiens

<400> SEQUENCE: 356
aacatgatgt gagattactt t                                              21

<210> SEQ ID NO 357
<211> LENGTH: 21
<212> TYPE: DNA
<213> ORGANISM: Homo sapiens

<400> SEQUENCE: 357
taggtagttt cctgttgttg g                                              21

<210> SEQ ID NO 358
<211> LENGTH: 21
<212> TYPE: DNA
<213> ORGANISM: Homo sapiens

<400> SEQUENCE: 358
gcagcagcgg ctagggcggc g                                              21

<210> SEQ ID NO 359
<211> LENGTH: 21
<212> TYPE: DNA
<213> ORGANISM: Homo sapiens

<400> SEQUENCE: 359
taggtagttt cctgttgttg g                                              21

<210> SEQ ID NO 360
<211> LENGTH: 21
<212> TYPE: DNA
<213> ORGANISM: Homo sapiens

<400> SEQUENCE: 360
gcggcggtag ctgcaggggt c                                              21

<210> SEQ ID NO 361
<211> LENGTH: 21
<212> TYPE: DNA
<213> ORGANISM: Homo sapiens

<400> SEQUENCE: 361
taggtagttt cctgttgttg g                                              21

<210> SEQ ID NO 362
<211> LENGTH: 36
<212> TYPE: DNA
<213> ORGANISM: Homo sapiens

<400> SEQUENCE: 362
```

```
gcccggggga gtcggctgga gccggctgcg ctttga                              36

<210> SEQ ID NO 363
<211> LENGTH: 39
<212> TYPE: DNA
<213> ORGANISM: Homo sapiens

<400> SEQUENCE: 363
cgggcaacaa ccaaagtcgc cgcaactgca gcacagagc                            39

<210> SEQ ID NO 364
<211> LENGTH: 36
<212> TYPE: DNA
<213> ORGANISM: Artificial Sequence
<220> FEATURE:
<223> OTHER INFORMATION: mutated sequence from human

<400> SEQUENCE: 364
gcccggggga ctagagtggg ucgggctgcg ctttga                              36

<210> SEQ ID NO 365
<211> LENGTH: 36
<212> TYPE: DNA
<213> ORGANISM: Artificial Sequence
<220> FEATURE:
<223> OTHER INFORMATION: mutated sequence from human

<400> SEQUENCE: 365
gcccggggga gggatagtgg ucgggctgcg ctttga                              36

<210> SEQ ID NO 366
<211> LENGTH: 39
<212> TYPE: DNA
<213> ORGANISM: Artificial Sequence
<220> FEATURE:
<223> OTHER INFORMATION: mutated sequence from human

<400> SEQUENCE: 366
cgggcaacta ggaaagtcgc cgcaactgca gcacagagc                            39

<210> SEQ ID NO 367
<211> LENGTH: 55
<212> TYPE: DNA
<213> ORGANISM: Caenorhabditis elegans

<400> SEQUENCE: 367
gtggtattgt tgttctgtaa gccacatagg ttgtattctc tagttaacac atagt          55

<210> SEQ ID NO 368
<211> LENGTH: 55
<212> TYPE: DNA
<213> ORGANISM: Caenorhabditis elegans

<400> SEQUENCE: 368
cacctacctc ctcaaattgc actctcaggg attcttttt ttttcaaata gaact           55

<210> SEQ ID NO 369
<211> LENGTH: 55
<212> TYPE: DNA
<213> ORGANISM: Artificial Sequence
<220> FEATURE:
<223> OTHER INFORMATION: mutated sequence from C.elegans

<400> SEQUENCE: 369
gtggtattgt tgttctgtat atttgatagg ttgtattctc tagttaacac atagt          55
```

<210> SEQ ID NO 370
<211> LENGTH: 21
<212> TYPE: RNA
<213> ORGANISM: Caenorhabditis elegans

<400> SEQUENCE: 370
ucccugagac cuguggcuug a                                                  21

<210> SEQ ID NO 371
<211> LENGTH: 21
<212> TYPE: RNA
<213> ORGANISM: Artificial Sequence
<220> FEATURE:
<223> OTHER INFORMATION: partial complementary sequence of C.elegans

<400> SEQUENCE: 371
aagccacagg ucucagaagu u                                                  21

<210> SEQ ID NO 372
<211> LENGTH: 10
<212> TYPE: RNA
<213> ORGANISM: Homo sapiens

<400> SEQUENCE: 372
gaccauggcu                                                               10

<210> SEQ ID NO 373
<211> LENGTH: 11
<212> TYPE: RNA
<213> ORGANISM: Homo sapiens

<400> SEQUENCE: 373
auguaugugg g                                                             11

<210> SEQ ID NO 374
<211> LENGTH: 10
<212> TYPE: RNA
<213> ORGANISM: Homo sapiens

<400> SEQUENCE: 374
cagcauggag                                                               10

<210> SEQ ID NO 375
<211> LENGTH: 10
<212> TYPE: RNA
<213> ORGANISM: Homo sapiens

<400> SEQUENCE: 375
agcauggagu                                                               10

<210> SEQ ID NO 376
<211> LENGTH: 11
<212> TYPE: RNA
<213> ORGANISM: Homo sapiens

<400> SEQUENCE: 376
ccucauggaa g                                                             11

<210> SEQ ID NO 377
<211> LENGTH: 10
<212> TYPE: RNA
<213> ORGANISM: Homo sapiens

```
<400> SEQUENCE: 377
auaaaugaca                                                          10

<210> SEQ ID NO 378
<211> LENGTH: 10
<212> TYPE: RNA
<213> ORGANISM: Homo sapiens

<400> SEQUENCE: 378
aaagaugagc                                                          10

<210> SEQ ID NO 379
<211> LENGTH: 10
<212> TYPE: RNA
<213> ORGANISM: Homo sapiens

<400> SEQUENCE: 379
aaggaugaau                                                          10

<210> SEQ ID NO 380
<211> LENGTH: 11
<212> TYPE: RNA
<213> ORGANISM: Homo sapiens

<400> SEQUENCE: 380
gcccaugcuc c                                                        11

<210> SEQ ID NO 381
<211> LENGTH: 11
<212> TYPE: RNA
<213> ORGANISM: Homo sapiens

<400> SEQUENCE: 381
ggggaugcua a                                                        11

<210> SEQ ID NO 382
<211> LENGTH: 11
<212> TYPE: RNA
<213> ORGANISM: Homo sapiens

<400> SEQUENCE: 382
aaggaugcgc c                                                        11

<210> SEQ ID NO 383
<211> LENGTH: 11
<212> TYPE: RNA
<213> ORGANISM: Homo sapiens

<400> SEQUENCE: 383
uaucauguua a                                                        11

<210> SEQ ID NO 384
<211> LENGTH: 11
<212> TYPE: RNA
<213> ORGANISM: Homo sapiens

<400> SEQUENCE: 384
aaagaugagc g                                                        11

<210> SEQ ID NO 385
<211> LENGTH: 11
<212> TYPE: RNA
<213> ORGANISM: Homo sapiens
```

<400> SEQUENCE: 385
gcagaugugc u                                                            11

<210> SEQ ID NO 386
<211> LENGTH: 11
<212> TYPE: RNA
<213> ORGANISM: Homo sapiens

<400> SEQUENCE: 386
aaagauggag c                                                            11

<210> SEQ ID NO 387
<211> LENGTH: 11
<212> TYPE: RNA
<213> ORGANISM: Homo sapiens

<400> SEQUENCE: 387
uggaaugauc c                                                            11

<210> SEQ ID NO 388
<211> LENGTH: 11
<212> TYPE: RNA
<213> ORGANISM: Homo sapiens

<400> SEQUENCE: 388
gcccaugccu c                                                            11

<210> SEQ ID NO 389
<211> LENGTH: 11
<212> TYPE: RNA
<213> ORGANISM: Homo sapiens

<400> SEQUENCE: 389
ccggauguca g                                                            11

<210> SEQ ID NO 390
<211> LENGTH: 11
<212> TYPE: RNA
<213> ORGANISM: Artificial Sequence
<220> FEATURE:
<223> OTHER INFORMATION: mutated sequence from human

<400> SEQUENCE: 390
cacaaugcgc g                                                            11

<210> SEQ ID NO 391
<211> LENGTH: 11
<212> TYPE: RNA
<213> ORGANISM: Homo sapiens

<400> SEQUENCE: 391
ccccaugcgc u                                                            11

<210> SEQ ID NO 392
<211> LENGTH: 11
<212> TYPE: RNA
<213> ORGANISM: Homo sapiens

<400> SEQUENCE: 392
gcggaugcgc g                                                            11

<210> SEQ ID NO 393

```
-continued

<211> LENGTH: 11
<212> TYPE: RNA
<213> ORGANISM: Homo sapiens

<400> SEQUENCE: 393
uugcaugaaa c                                                                11

<210> SEQ ID NO 394
<211> LENGTH: 11
<212> TYPE: RNA
<213> ORGANISM: Homo sapiens

<400> SEQUENCE: 394
cuggaugccu c                                                                11

<210> SEQ ID NO 395
<211> LENGTH: 11
<212> TYPE: RNA
<213> ORGANISM: Homo sapiens

<400> SEQUENCE: 395
cuggaugucu g                                                                11

<210> SEQ ID NO 396
<211> LENGTH: 11
<212> TYPE: RNA
<213> ORGANISM: Homo sapiens

<400> SEQUENCE: 396
cucuaugauu c                                                                11

<210> SEQ ID NO 397
<211> LENGTH: 11
<212> TYPE: RNA
<213> ORGANISM: Homo sapiens

<400> SEQUENCE: 397
cuuuauguuc a                                                                11

<210> SEQ ID NO 398
<211> LENGTH: 11
<212> TYPE: RNA
<213> ORGANISM: Homo sapiens

<400> SEQUENCE: 398
gaggaugggu g                                                                11

<210> SEQ ID NO 399
<211> LENGTH: 11
<212> TYPE: RNA
<213> ORGANISM: Homo sapiens

<400> SEQUENCE: 399
uuggaugcuu g                                                                11

<210> SEQ ID NO 400
<211> LENGTH: 11
<212> TYPE: RNA
<213> ORGANISM: Homo sapiens

<400> SEQUENCE: 400
cgcuauguca g                                                                11
```

```
<210> SEQ ID NO 401
<211> LENGTH: 11
<212> TYPE: RNA
<213> ORGANISM: Homo sapiens

<400> SEQUENCE: 401
cagaaugggg c                                                         11

<210> SEQ ID NO 402
<211> LENGTH: 11
<212> TYPE: RNA
<213> ORGANISM: Homo sapiens

<400> SEQUENCE: 402
gaguaugagc c                                                         11

<210> SEQ ID NO 403
<211> LENGTH: 11
<212> TYPE: RNA
<213> ORGANISM: Homo sapiens

<400> SEQUENCE: 403
cggcaugagu u                                                         11

<210> SEQ ID NO 404
<211> LENGTH: 11
<212> TYPE: RNA
<213> ORGANISM: Homo sapiens

<400> SEQUENCE: 404
gauuaugcaa u                                                         11

<210> SEQ ID NO 405
<211> LENGTH: 11
<212> TYPE: RNA
<213> ORGANISM: Homo sapiens

<400> SEQUENCE: 405
agcaauggcu c                                                         11

<210> SEQ ID NO 406
<211> LENGTH: 11
<212> TYPE: RNA
<213> ORGANISM: Homo sapiens

<400> SEQUENCE: 406
caucaugcau u                                                         11

<210> SEQ ID NO 407
<211> LENGTH: 11
<212> TYPE: RNA
<213> ORGANISM: Homo sapiens

<400> SEQUENCE: 407
aagaauguuu u                                                         11

<210> SEQ ID NO 408
<211> LENGTH: 11
<212> TYPE: RNA
<213> ORGANISM: Homo sapiens

<400> SEQUENCE: 408
uuuaauggaa a                                                         11
```

<210> SEQ ID NO 409
<211> LENGTH: 11
<212> TYPE: RNA
<213> ORGANISM: Homo sapiens

<400> SEQUENCE: 409
aucaauguga c                                                              11

<210> SEQ ID NO 410
<211> LENGTH: 11
<212> TYPE: RNA
<213> ORGANISM: Homo sapiens

<400> SEQUENCE: 410
acaaauggau g                                                              11

<210> SEQ ID NO 411
<211> LENGTH: 11
<212> TYPE: RNA
<213> ORGANISM: Homo sapiens

<400> SEQUENCE: 411
auggaugaau g                                                              11

<210> SEQ ID NO 412
<211> LENGTH: 11
<212> TYPE: RNA
<213> ORGANISM: Homo sapiens

<400> SEQUENCE: 412
augaaugaau a                                                              11

<210> SEQ ID NO 413
<211> LENGTH: 11
<212> TYPE: RNA
<213> ORGANISM: Homo sapiens

<400> SEQUENCE: 413
cauaaugggg u                                                              11

<210> SEQ ID NO 414
<211> LENGTH: 11
<212> TYPE: RNA
<213> ORGANISM: Homo sapiens

<400> SEQUENCE: 414
aaagaugugu c                                                              11

<210> SEQ ID NO 415
<211> LENGTH: 11
<212> TYPE: RNA
<213> ORGANISM: Homo sapiens

<400> SEQUENCE: 415
gccaaugcca g                                                              11

<210> SEQ ID NO 416
<211> LENGTH: 11
<212> TYPE: RNA
<213> ORGANISM: Homo sapiens

<400> SEQUENCE: 416
aaagaugugu c                                                              11

<210> SEQ ID NO 417
<211> LENGTH: 11
<212> TYPE: RNA
<213> ORGANISM: Homo sapiens

<400> SEQUENCE: 417
uuaaauguca g                                                          11

<210> SEQ ID NO 418
<211> LENGTH: 11
<212> TYPE: RNA
<213> ORGANISM: Homo sapiens

<400> SEQUENCE: 418
cgugauggga u                                                          11

<210> SEQ ID NO 419
<211> LENGTH: 11
<212> TYPE: RNA
<213> ORGANISM: Artificial Sequence
<220> FEATURE:
<223> OTHER INFORMATION: mutated sequence from human

<400> SEQUENCE: 419
cgugaaggga u                                                          11

<210> SEQ ID NO 420
<211> LENGTH: 11
<212> TYPE: RNA
<213> ORGANISM: Homo sapiens

<400> SEQUENCE: 420
gagaaugccg g                                                          11

<210> SEQ ID NO 421
<211> LENGTH: 11
<212> TYPE: RNA
<213> ORGANISM: Artificial Sequence
<220> FEATURE:
<223> OTHER INFORMATION: mutated sequence from human

<400> SEQUENCE: 421
gagaaagccg g                                                          11

<210> SEQ ID NO 422
<211> LENGTH: 11
<212> TYPE: RNA
<213> ORGANISM: Homo sapiens

<400> SEQUENCE: 422
gugaaugucc u                                                          11

<210> SEQ ID NO 423
<211> LENGTH: 11
<212> TYPE: RNA
<213> ORGANISM: Homo sapiens

<400> SEQUENCE: 423
guggaugcug c                                                          11

<210> SEQ ID NO 424
<211> LENGTH: 11
<212> TYPE: RNA

```
<213> ORGANISM: Homo sapiens

<400> SEQUENCE: 424
aaagaugagg g                                                        11

<210> SEQ ID NO 425
<211> LENGTH: 22
<212> TYPE: RNA
<213> ORGANISM: Homo sapiens

<400> SEQUENCE: 425
uggcaguguc uuagcugguu gu                                            22

<210> SEQ ID NO 426
<211> LENGTH: 22
<212> TYPE: RNA
<213> ORGANISM: Homo sapiens

<400> SEQUENCE: 426
uggcaguguc uuagcugguu gu                                            22

<210> SEQ ID NO 427
<211> LENGTH: 21
<212> TYPE: RNA
<213> ORGANISM: Artificial Sequence
<220> FEATURE:
<223> OTHER INFORMATION: reverse complementary sequence to C.elegans

<400> SEQUENCE: 427
uugaagacuc uggacaccga a                                             21

<210> SEQ ID NO 428
<211> LENGTH: 21
<212> TYPE: RNA
<213> ORGANISM: Caenorhabditis elegans

<400> SEQUENCE: 428
ucccugagac cuguggcuua a                                             21

<210> SEQ ID NO 429
<211> LENGTH: 15
<212> TYPE: RNA
<213> ORGANISM: Homo sapiens

<400> SEQUENCE: 429
ggagaagcga ccgca                                                    15

<210> SEQ ID NO 430
<211> LENGTH: 11
<212> TYPE: RNA
<213> ORGANISM: Homo sapiens

<400> SEQUENCE: 430
gugccuucuc c                                                        11

<210> SEQ ID NO 431
<211> LENGTH: 11
<212> TYPE: RNA
<213> ORGANISM: Homo sapiens

<400> SEQUENCE: 431
uugggauuua u                                                        11
```

```
<210> SEQ ID NO 432
<211> LENGTH: 11
<212> TYPE: RNA
<213> ORGANISM: Homo sapiens

<400> SEQUENCE: 432
uaaaucccau g                                                           11

<210> SEQ ID NO 433
<211> LENGTH: 21
<212> TYPE: RNA
<213> ORGANISM: Caenorhabditis elegans

<400> SEQUENCE: 433
ucccugagac cuguggcuua a                                                21

<210> SEQ ID NO 434
<211> LENGTH: 17
<212> TYPE: RNA
<213> ORGANISM: Caenorhabditis elegans

<400> SEQUENCE: 434
ucacaacaac ucaggga                                                     17

<210> SEQ ID NO 435
<211> LENGTH: 21
<212> TYPE: RNA
<213> ORGANISM: Caenorhabditis elegans

<400> SEQUENCE: 435
ucccugagac cucaagugug a                                                21

<210> SEQ ID NO 436
<211> LENGTH: 28
<212> TYPE: RNA
<213> ORGANISM: Caenorhabditis elegans

<400> SEQUENCE: 436
gucacuuuga caccacgauc cagccuaa                                         28

<210> SEQ ID NO 437
<211> LENGTH: 21
<212> TYPE: RNA
<213> ORGANISM: Caenorhabditis elegans

<400> SEQUENCE: 437
ucccugagac cucaagugug a                                                21

<210> SEQ ID NO 438
<211> LENGTH: 21
<212> TYPE: RNA
<213> ORGANISM: Artificial Sequence
<220> FEATURE:
<223> OTHER INFORMATION: modified C. elegans sequence

<400> SEQUENCE: 438
gucacuuuga caacucaggg a                                                21

<210> SEQ ID NO 439
<211> LENGTH: 22
<212> TYPE: RNA
<213> ORGANISM: Homo sapiens

<400> SEQUENCE: 439
```

```
uggcaguguc uuagcugguu gu                                              22

<210> SEQ ID NO 440
<211> LENGTH: 46
<212> TYPE: RNA
<213> ORGANISM: Homo sapiens

<400> SEQUENCE: 440
uauugaagau gcugccugua uuugagagac ugccauacau aauaua                    46

<210> SEQ ID NO 441
<211> LENGTH: 22
<212> TYPE: RNA
<213> ORGANISM: Homo sapiens

<400> SEQUENCE: 441
uggcaguguu ucagcugguu gu                                              22

<210> SEQ ID NO 442
<211> LENGTH: 36
<212> TYPE: RNA
<213> ORGANISM: Homo sapiens

<400> SEQUENCE: 442
gcccggggga gucggcugga gccggcugcg cuuuga                               36

<210> SEQ ID NO 443
<211> LENGTH: 22
<212> TYPE: RNA
<213> ORGANISM: Homo sapiens

<400> SEQUENCE: 443
uggcaguguc uuagcugguu gu                                              22

<210> SEQ ID NO 444
<211> LENGTH: 22
<212> TYPE: RNA
<213> ORGANISM: Homo sapiens

<400> SEQUENCE: 444
uggcaguguc uuagcugguu gu                                              22

<210> SEQ ID NO 445
<211> LENGTH: 35
<212> TYPE: RNA
<213> ORGANISM: Artificial Sequence
<220> FEATURE:
<223> OTHER INFORMATION: mutated human RNA sequence

<400> SEQUENCE: 445
gcccggggga cuagaguggg ucgggcugcg uuuga                                35

<210> SEQ ID NO 446
<211> LENGTH: 22
<212> TYPE: RNA
<213> ORGANISM: Homo sapiens

<400> SEQUENCE: 446
uggcaguguc uuagcugguu gu                                              22

<210> SEQ ID NO 447
<211> LENGTH: 36
<212> TYPE: RNA
<213> ORGANISM: Homo sapiens
```

```
<400> SEQUENCE: 447
gcccggggga gggauagugg ucgggcugcg cuuuga                                 36

<210> SEQ ID NO 448
<211> LENGTH: 20
<212> TYPE: RNA
<213> ORGANISM: Homo sapiens

<400> SEQUENCE: 448
uggcaguguc uuagcugguu                                                   20

<210> SEQ ID NO 449
<211> LENGTH: 35
<212> TYPE: RNA
<213> ORGANISM: Homo sapiens

<400> SEQUENCE: 449 ggagacccu uguugcacug cccccuggcc aggag                                   35

<210> SEQ ID NO 450
<211> LENGTH: 15
<212> TYPE: RNA
<213> ORGANISM: Homo sapiens

<400> SEQUENCE: 450
uggcaguguc uuagc                                                        15

<210> SEQ ID NO 451
<211> LENGTH: 36
<212> TYPE: RNA
<213> ORGANISM: Homo sapiens

<400> SEQUENCE: 451
cggggcaaca accaaagucg ccgcaacugc agcaca                                 36

<210> SEQ ID NO 452
<211> LENGTH: 22
<212> TYPE: RNA
<213> ORGANISM: Homo sapiens

<400> SEQUENCE: 452
uggcaguguc uuagcugguu gu                                                22

<210> SEQ ID NO 453
<211> LENGTH: 35
<212> TYPE: RNA
<213> ORGANISM: Artificial Sequence
<220> FEATURE:
<223> OTHER INFORMATION: mutated human sequence

<400> SEQUENCE: 453
cgggcaacua ggaaagucgc cgcaacugca gcaca                                  35

<210> SEQ ID NO 454
<211> LENGTH: 21
<212> TYPE: RNA
<213> ORGANISM: Artificial Sequence
<220> FEATURE:
<223> OTHER INFORMATION: modified C. elegans RNA sequence

<400> SEQUENCE: 454
ucccugagac cuguggcuua a                                                 21
```

```
<210> SEQ ID NO 455
<211> LENGTH: 21
<212> TYPE: RNA
<213> ORGANISM: Artificial Sequence
<220> FEATURE:
<223> OTHER INFORMATION: modified C. elegans sequence

<400> SEQUENCE: 455
aagccacagg ucucagaagu u                                              21

<210> SEQ ID NO 456
<211> LENGTH: 21
<212> TYPE: RNA
<213> ORGANISM: Artificial Sequence
<220> FEATURE:
<223> OTHER INFORMATION: modified C. elegans RNA sequence

<400> SEQUENCE: 456
ucccugagac cuguggcuua a                                              21

<210> SEQ ID NO 457
<211> LENGTH: 55
<212> TYPE: RNA
<213> ORGANISM: Caenorhabditis elegans

<400> SEQUENCE: 457
caccuaccuc cucaaauugc acucucaggg auucuuuuuu uuucaaaua gaacu          55

<210> SEQ ID NO 458
<211> LENGTH: 21
<212> TYPE: RNA
<213> ORGANISM: Artificial Sequence
<220> FEATURE:
<223> OTHER INFORMATION: modified c. elegans RNA sequence

<400> SEQUENCE: 458
ucccugagac cuguggcuua a                                              21

<210> SEQ ID NO 459
<211> LENGTH: 55
<212> TYPE: RNA
<213> ORGANISM: Caenorhabditis elegans

<400> SEQUENCE: 459
gugguauugu uguucuguaa gccacauagg uuguauucuc uaguuaacac auagu         55

<210> SEQ ID NO 460
<211> LENGTH: 21
<212> TYPE: RNA
<213> ORGANISM: Artificial Sequence
<220> FEATURE:
<223> OTHER INFORMATION: modified C. elegans RNA sequence

<400> SEQUENCE: 460
ucccugagac cuguggcuua a                                              21

<210> SEQ ID NO 461
<211> LENGTH: 55
<212> TYPE: RNA
<213> ORGANISM: Artificial Sequence
<220> FEATURE:
<223> OTHER INFORMATION: modified C. elegans RNA sequence

<400> SEQUENCE: 461
caccuacugu uguucuguau auuugauagg uuguauucuc uaguuaacac auagu         55
```

```
<210> SEQ ID NO 462
<211> LENGTH: 16
<212> TYPE: RNA
<213> ORGANISM: Homo sapiens

<400> SEQUENCE: 462
gggagaagcg accgca                                                     16

<210> SEQ ID NO 463
<211> LENGTH: 11
<212> TYPE: RNA
<213> ORGANISM: Homo sapiens

<400> SEQUENCE: 463
gugccuucuc c                                                          11

<210> SEQ ID NO 464
<211> LENGTH: 10
<212> TYPE: RNA
<213> ORGANISM: Homo sapiens

<400> SEQUENCE: 464
uugggauuua                                                            10

<210> SEQ ID NO 465
<211> LENGTH: 11
<212> TYPE: RNA
<213> ORGANISM: Homo sapiens

<400> SEQUENCE: 465
uaaaucccau g                                                          11
```

MIRNA TARGET PREDICTION

CROSS-REFERENCE TO RELATED APPLICATIONS

This application claims the benefit of U.S. provisional Application No. 61/306,353 filed Feb. 19, 2010, the disclosure of which is incorporated in its entirety by reference herein.

SEQUENCE LISTING

The text file revised_sequence_listing.txt, created Sep. 9, 2013, and of size 76 KB, filed herewith, is hereby incorporated by reference.

REFERENCE TO A COMPUTER PROGRAM LISTING COMPACT DISK APPENDIX

The material in the accompanying computer program listing is hereby incorporated by reference into this application. The computer program listing appendix includes the files Example 2.txt created Jan. 22, 2013 having a size of 38 KB; and Example 3.txt created Jan. 22, 2013 having a size of 40 KB, both of which are incorporated in their entirety by reference herein.

FIELD OF THE INVENTION

The present invention relates to methods of predicting miRNA targets using sequence similarity and thermodynamic stability of miRNA-bridges across both 3' and 5' untranslated regions (UTRs). Such methods find use in research, diagnostic and therapeutic settings (e.g., to discover targets, drugs, diagnostic products, etc.).

BACKGROUND

Current microRNA (miRNA) study presumes miRNAs interact with the 3'UTR of mRNAs to inhibit translation. Because of the non-perfect complementary sequences between mRNA and miRNA, miRNA target determination constitutes a bottleneck in miRNA applications, even with the latest achievements in miRNA profiling of cancer signatures. Currently, only a few miRNA of the thousands known to exist in animals and viruses have had their functionality and targets experimentally verified. The known interaction between the 5' end region of miRNA with the 3' UTR of mRNA has been utilized by several programs for target prediction. However, because the stretch of perfectly-matched sequences can be as small as 6-mer and G-U wobbles can contribute to functional hybridization, the problem of false positive targets becomes a major issue.

MiRNAs are small non-coding RNAs which regulate gene expression either by direct cleavage of the target mRNA or by inhibition of protein synthesis while preserving the target mRNAs. In animals, nascent miRNA transcripts are processed into ~70 nucleotide (nt) precursors (pre-miRNA) in the nucleus and exported into the cytoplasm to be cleaved by Dicer enzymes to generate ~22 nt imperfect double stranded RNA (dsRNA). In most cases, one of the two strands, called mature miRNA, is incorporated into the RNA-induced silencing complex (RISC), while the other strand appears to be degraded. This mature miRNA-RISC complex interacts with mRNA by complementary sequences. The complex either cleaves the target mRNA when the miRNA and mRNA are almost totally complementary, or represses protein translation when there are only partial complementary sequences between them. In addition to post-transcriptional regulation, miRNA appears to influence DNA methylation.

The first miRNA lin-4 was found in *C. elegans* in 1993, and the second miRNA let-7 was found much later in 2000 (both were discovered through genetic mutation studies). The identification of let-7 raised the possibility of similar small RNAs, and hundreds of miRNAs have since been identified in plants, worms, vertebrates, and human viruses by a combination of computational predictions and reverse genetics. Currently 321 human miRNAs are listed in the miRBase::Sequences database at the Sanger Institute; a recent study has added 89 miRNAs (S. Griffiths-Jones, The microRNA Registry. Nucleic Acids Res 32: D109-11 (2004); I. Bentwich, A. Avniel, Y. Karov, R. Aharonov, S. Gilad, O. Barad, A. Barzilai, P. Einat, U. Einav, E. Meiri, E. Sharon, Y. Spector, and Z. Bentwich, Identification of hundreds of conserved and non-conserved human microRNAs. Nat Genet (2005)). Current estimates are that miRNAs represent ~1% of each organism's genes, and show developmental stage-, cell type-, and tissue-specificity. Some miRNAs are highly abundant. Recent comparative analysis of the human, mouse, rat and dog genome suggests that there are more miRNAs to be identified and that known miRNAs regulate at least 20% of human genes.

Studies of RNA interference, where dsRNAs are processed into ~21 nt lengths and one strand's perfect complement to mRNA guides the RISC to degrade mRNAs, have progressed rapidly, and the shared biochemical processes of miRNA are rather well known. Publications on miRNAs are also quickly accumulating, including recent genome-wide miRNA profiling efforts and other data. This may leave the impression that miRNA function is relatively well characterized. However, fewer than 10 miRNAs in animal have experimentally validated functions and targets (Table 1). Unlike plant miRNAs, whose complementary sequences very closely match the target mRNA, most animal miRNAs are only partially complementary, making it a daunting task to connect miRNA-mRNA functional pairs. To complicate matters, one miRNA can target several genes, while one gene may be regulated by multiple miRNAs.

TABLE 1

Experimentally-verified miRNA functions and targets

| Animal | miRNA | Target Gene | Function | References |
|---|---|---|---|---|
| *Caenorhabditis elegans* | lin-4 | lin-14 | developmental timing | [9, 19] |
| | | lin-28 | developmental timing | [20] |
| | let-7 | lin-41 | developmental timing | [21] |
| | | hbl-1 | developmental timing | [22, 23] |
| | lsy-6 | cog-1 | neuronal cell fate | [24] |
| | miR-273 | die-1 | neuronal cell fate | [25] |
| *Drosophila melanogaster* | bantam | Hid | cell death, proliferation | [26] |
| | miR-14 | Unknown | cell death, fat storage | [27] |
| *Mus musculus* | miR-181a | Unknown | haematopoietic cell fate | [28] |
| | miR-196 | Hoxb8 | unknown (direct cleavage) | [29] |
| | miR-375 (islet specific) | Mtpn | insulin secretion | [30] |
| *Homo sapiens* | miR-143 | ERK5 | adipocyte differentiation | [31] |
| | miR-84 (let-7 family) | RAS | unknown (cancer related) | [32] |
| | miR-17-5p | E2F1 | tumor suppressor? | [33] |
| | miR-20a | E2F1 | tumor suppressor? | [33] |

Several computational efforts to identify miRNA targets have been well covered in a recent review (J. R. Brown and P. Sanseau, A computational view of microRNAs and their targets. *Drug Discov Today* 10: 595-601 (2005)). All of these algorithms are based on the knowledge of two known miRNAs (lin-4 and let-7) and their target mRNAs: partial complementary sequences to the target mRNA 3'UTR (untranslated region in 3'-end side) and conserved target 3' UTR sequences in orthologous genes. Even before the experimental confirmation of critical pairing of the 5' end region of miRNAs, this feature was widely included in all the prediction tools following a computational approach. In the first versions of TargetS can (B. P. Lewis, I. H. Shih, M. W. Jones-Rhoades, D. P. Bartel, and C. B. Burge, Prediction of mammalian microRNA targets. Cell 115: 787-98 (2003)) and miRanda (A. J. Enright, B. John, U. Gaul, T. Tuschl, C. Sander, and D. S. Marks, MicroRNA targets in Drosophila. Genome Biol 5: R1 (2003)), multiple binding sites in a 3' UTR were predicted, while RNAhybrid (M. Rehmsmeier, P. Steffen, M. Hochsmann, and R. Giegerich, Fast and effective prediction of microRNA/target duplexes. Rna 10: 1507-17 (2004)) and the second version of TargetScanS (B. P. Lewis, C. B. Burge, and D. P. Bartel, Conserved seed pairing, often flanked by adenosines, indicates that thousands of human genes are microRNA targets. Cell 120: 15-20 (2005)) include a single binding site per UTR. Recently, an algorithm to identify targets for both single miRNAs and combinations of miRNAs has been developed, showing coordinated miRNA control (A. Krek, D. Grun, M. N. Poy, R. Wolf, L. Rosenberg, E. J. Epstein, P. MacMenamin, I. da Piedade, K. C. Gunsalus, M. Stoffel, and N. Rajewsky, Combinatorial microRNA target predictions. Nat Genet 37: 495-500 (2005)). Some of the computationally predicted targets were confirmed by a reporter gene assay containing target 3' UTR sequences. Single-site target prediction have improved by structure-function studies of a model miRNA (M. Kiriakidou, P. T. Nelson, A. Kouranov, P. Fitziev, C. Bouyioukos, Z. Mourelatos, and A. Hatzigeorgiou, A combined computational-experimental approach predicts human microRNA targets. Genes Dev 18: 1165-78 (2004)), while secondary structures of target 3' UTRs were considered in an algorithm (H. Robins, Y. Li, and R. W. Padgett, Incorporating structure to predict microRNA targets. Proc Natl Acad Sci USA 102: 4006-9 (2005)). The importance of architecture of 3' UTR target sites has been experimentally demonstrated.

Unfortunately, predicted targets for mammalian miRNAs lack overlap among research groups. Recent progress in miRNA detection methods via microarrays enables the detection of genome-wide miRNA expression patterns. One study tried to correlate miRNA and mRNA co-expression with previously predicted miRNAs and target mRNAs pairs, but reported unrelated expression patterns and predicted targets, raising doubts regarding the validity of target mRNAs. Additionally, recent rigorous experiments show the levels of putative target mRNAs computationally predicted with verified reporter assays to be independent of the tested miRNA levels. These studies raise the possibility of mRNA degradation or translational level regulation by miRNAs. Currently, miR-196 is the only known animal miRNA that cleaves mRNA directly through its almost total complementary sequence to the target mRNA (only one G:U wobble among 21 nt), a rare feature in animal miRNAs. Another study reported that a broad range of mRNAs showed reduced expression levels due to externally introduced miRNAs. The study also reported that most of the reduced mRNAs had partially matched sequences in their 3' UTR with the introduced miRNA. Therefore, even given the current progress, there is a major lack of knowledge of the function and targets of miRNAs.

A recent NEWS & VIEW section in the journal Nature reported on three cancer-related miRNA studies (P. S. Meltzer, Cancer genomics: small RNAs with big impacts. Nature 435: 745-6 (2005)): a global miRNA profile study of various tumor types (J. Lu, G. Getz, E. A. Miska, E. Alvarez-Saavedra, J. Lamb, D. Peck, A. Sweet-Cordero, B. L. Ebert, R. H. Mak, A. A. Ferrando, J. R. Downing, T. Jacks, H. R. Horvitz, and T. R. Golub, MicroRNA expression profiles classify human cancers. Nature 435: 834-8 (2005)), and two studies focused more on the miRNA cluster from a c13orf25 gene (a gene among amplified copies in a chromosome 13 fragment in human lymphomas). Different miRNA profiles of normal and cancer cells have been reported previously, but the new global miRNA profile study showed, remarkably, that the expression pattern of miRNAs can define cancer types better than mRNA expression. The other two studies represent the complexity of the miRNA-related regulation process, building on the reports that miRNA genes themselves are frequently located at cancer related genomic regions. One group nominated c13orf25 miRNA as a candidate non-coding oncogene, while the other group proposed that the miRNAs encoded from the c13orf25 gene may antagonize the effects of different oncogenes.

Accordingly, there is a need for accurate miRNA target prediction models. Specifically, there is a great need for a model that predicts targets based not only on the 3'UTR interactions but also on 5'UTR interactions (e.g., bridging action).

SUMMARY OF THE INVENTION

The present invention solves one or more problems of the prior art by providing in at least one embodiment, a computer implemented method of identifying microRNA-mRNA complexes. The method comprises receiving data identifying an mRNA nucleotide sequence representing a gene or portions thereof into computer memory. The nucleotide sequence has an upstream region that is upstream of translation start site, a downstream region that is downstream of translation stop site, and an open reading frame. Data identifying a second set of microRNA (miRNA) nucleotide sequences is also received into computer memory. Each microRNA sequence of the second set has a 5' miRNA section and a 3' miRNA section. The downstream region is evaluated for sub-regions that are capable of stably hybridizing to at least of a portion of the 5' miRNA section. Similarly, the upstream region is evaluated for sub-regions that are capable of stably hybridizing to at least of a portion of the 3' miRNA section. Candidates for microRNA-mRNA complexes are identified as combinations of stably hybridizing sub-regions of the downstream section to portions of the 5' miRNA section and stably hybridizing sub-regions of the upstream section to portions of the 3'miRNA section.

In another embodiment, a non-transitory computer medium is encoded with instructions to carry out the method set forth above.

DESCRIPTION OF THE DRAWINGS

FIG. 7 shows human miRNA hsa-miR-34a and target AXIN2. (A) Predicted interactions between hsa-miR-34a and Axin2 UTR sequences. Extended seed match between the 5'-end of miR-34a and one of the 3'-UTR binding sites is shown in bold. Overlapping interactions between the 3'-end of miR-34a and the 5'-UTR inserted sequences are shown in bold. Energy was calculated using RNAhybrid. The sequences are SEQ ID NO: 439, SEQ ID NO: 440, SEQ ID NO: 441, SEQ ID NO: 442, SEQ ID NO: 443, SEQ ID NO: 444, SEQ ID NO: 445, SEQ ID NO: 446, and SEQ ID NO: 447 from top to bottom. (B) Schematic showing vector constructs containing firefly luciferase reporter gene used in transfection experiments. The 5'-UTR and 3'-UTR inserts are indicated as 5U and 3U respectively. (C) Luciferase expression fold change with miR-34a (no shading) normalized with negative control RNA oligo (dark shading). Firefly luciferase protein expression was normalized with Renilla luciferase protein. (D) Reporter constructs were co-transfected with anti-miR-34a oligo (no shading), Ambion, product ID, AM11030) and normalized with negative control RNA oligo (dark shading). (E) Effect of mutations in the 5'-UTR site—luciferase protein levels when reporter constructs were co-transfected with miR-34a (no shading) or negative control (dark shading). Error bars in panels C to E represent standard deviation from triplicate experiments;

FIG. 8 shows results for human miRNA hsa-miR-34a and target WNT1. (A) Predicted interactions between hsa-miR-34a and WNT1 UTR sequences. Extended seed match between the 5'-end of miR-34a and the 3'-UTR binding site is shown in bold. Interactions between the 3'-end of miR-34a and the 5'-UTR inserted sequences are shown in bold. The sequences are SEQ ID NO: 439, SEQ ID NO: 440, SEQ ID NO: 441, SEQ ID NO: 442, SEQ ID NO: 443, SEQ ID NO: 444, SEQ ID NO: 445, SEQ ID NO: 446, and SEQ ID NO: 447 from top to bottom. (B) Schematic of vector constructs containing firefly luciferase reporter gene used in transfection experiments. 5'-UTR and 3'-UTR inserts are indicated as 5U and 3U respectively. (C) Effect of 5'-UTR site in wildtype and mutant form on luciferase expression when treated with miR-34a. Renilla-normalized luciferase expression was normalized with negative control RNA oligo. Error bars represent standard deviation from triplicate experiments;

FIG. 10 shows results human miRNA hsa-miR-605 and SEC24D. (A) Predicted sites on the 5'-UTR and 3'-UTR targeted by the 3'-end and 5'-end, respectively, of hsa-miR-605. RNAhybrid. The sequences are SEQ ID NO: 462, SEQ ID NO: 463, SEQ ID NO: 464, SEQ ID NO: 465 from top to bottom then left to right. (B) Western blot of analysis of SEC24D. Protein extract (40n) from three days post-transfected HeLa cells was separated by SDS-PAGE and probed with anti-SEC24D monoclonal antibody, with actin (ACTB) as control. (C) Densitometric analysis of the western blots. X-ray films were scanned with hp scanjet 3570c (Hewlett-Packard) and quantified using NIH image software. (D) SEC24D mRNA expression fold change in HeLa cells two days post-transfection with Negative Control-1, Pre-mir-605 or anti-mir-605. Error bars represent standard deviation from a triplicate experiment;

DETAILED DESCRIPTION OF THE INVENTION

Embodiments of the present invention sought to analyze the hypothesis that mRNA translation repression occurs as a sequence-specific mechanism. More specifically, after the miRNA-RISC complex recruits mostly the 3'UTR region of mRNA, sequences of the 3'end region of miRNA are also crucial in blocking translation. The novel miRNA-mRNA functional model of the present invention predicts that miRNAs pairing with 3'UTR of target mRNAs will replace their 3'end parts by pairing with 5'UTR of target mRNAs when 3'UTR and 5'UTR sequences are in close proximity during the translation initiation process (See FIG. 1B).

Figure 1:
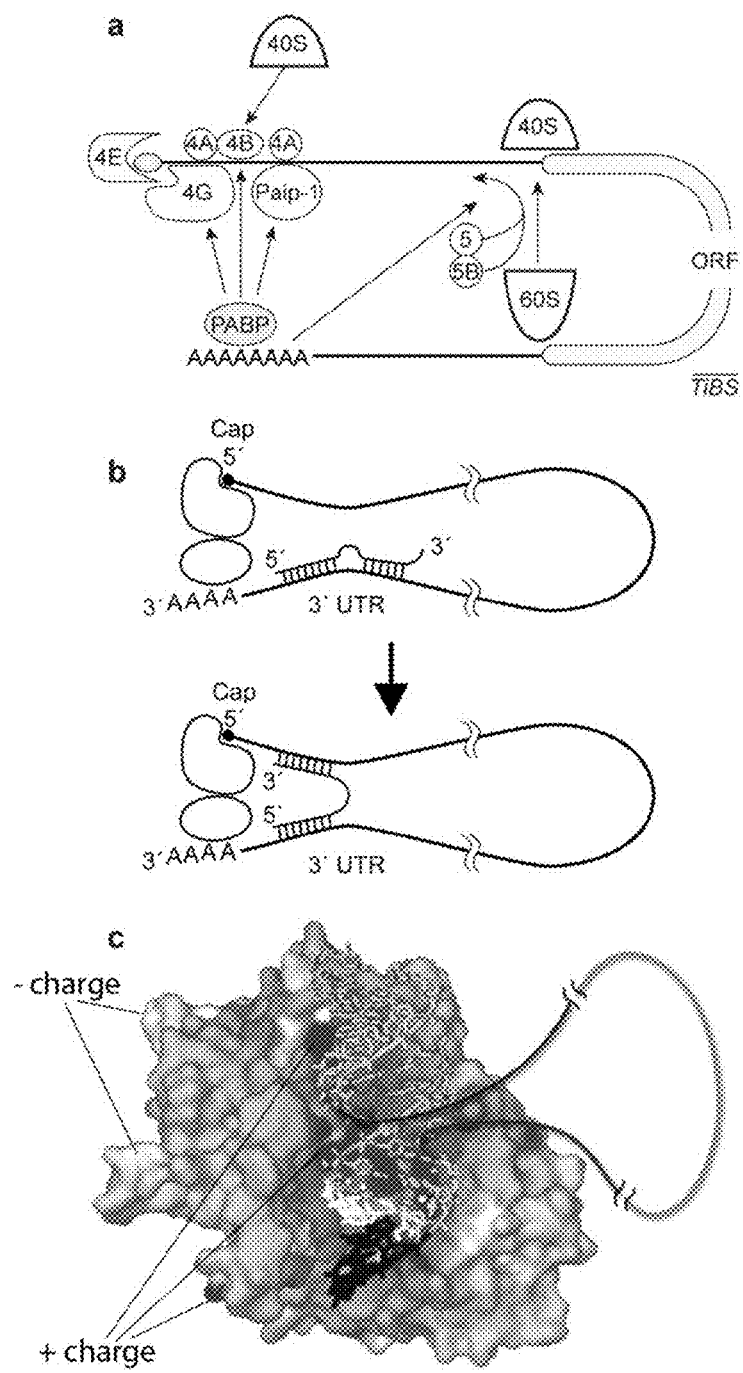
FIG. 1 provides an illustration of a miRNA functional model. (A) translation process depicted in the Wilkie et al.'s paper (1). (B) miRNA interaction with the 3'-UTR of a looping mRNA configuration. Loosely-bound (or non-bound) 3'-end miRNA can interact with a nearby 5'-UTR. The blobs represent the several interacting proteins between 5' cap and poly-A tail. (C) Available sites for the 5'-UTR and 3'-UTR in miRNP (miRNA and protein complex). The PIWI-dsRNA model by Ma et al. (J. B. Ma, Y. R. Yuan, G. Meister, Y. Pei, T. Tuschl, and D. J. Patel, Structural basis for 5'-end-specific recognition of guide RNA by the *A. fulgidus* Piwi protein. Nature 434: 666-70 (2005)), based on their PIWI-dsRNA crystal structure, is shown with electrostatic surface charge density on the PIWI. Some features are resolved-structure by X-ray crystallography, while features are from the A-form RNA model. We extrapolate RNA backbones—3'-UTR portion) and 5'-UTR portion lines, showing how miRNP might hold up both UTRs in an omega configuration. The extrapolated lines go over the additional positively-charged groove.

The poly(A) tail enhances translation through several protein interactions. A schematic diagram from a review paper (1) is shown in FIG. 1A. Through this kind of interaction, 3'UTR and 5'UTR may become physically adjacent. The loosely-bound 3'UTR region of mRNA to miRNA can be replaced by the 5'UTR region of mRNA if the 5'UTR target region exists nearby to form a more stable duplex with those portions of miRNA. A figure of one embodiment of the present invention is shown in FIG. 1B. Such a model has several heretofore unrealized merits, including, but not limited to: 1) it explains the differences between translation repression and mRNA degradation with one enzymatic process; 2) it accounts for an additional positively charged groove near the putative slicer catalytic site in the PIWI domain (a highly conserved motif within Argonaute protein, a component of RISC) in recent crystal structure papers (J. J. Song, S. K. Smith, G. J. Hannon, and L. Joshua-Tor, Crystal structure of Argonaute and its implications for RISC slicer activity. Science 305: 1434-7 (2004); J. B. Ma, Y. R. Yuan, G. Meister, Y. Pei, T. Tuschl, and D. J. Patel, Structural basis for 5'-end-specific recognition of guide RNA by the *A. fulgidus* Piwi protein. Nature 434: 666-70 (2005)); 3) it explains the 3'end sequence usage of miRNA; 4) it allows complex formation with ribosomes; and 5) it gives insights into the recent systematic analysis of miRNA-mRNA bind criteria.

Figure 2:
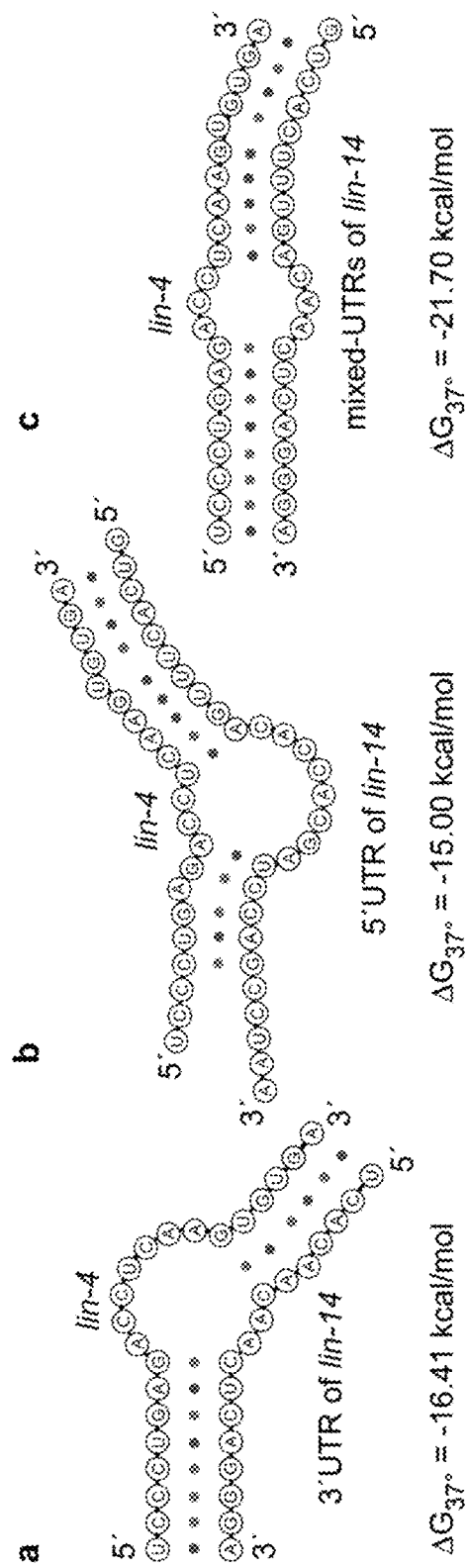
FIGS. 2A-C depict interactions between lin-4 and portions of lin-14 with G-C interactions represented by lines, A-U and G-U represented by dots between pairs and sequences in grey circles being paired and those in plain circles being non-paired. The sequences are SEQ ID NO: 433 and SEQ ID NO: 434 (from top to bottom) in FIG. 2A, SEQ ID NO: 435 and SEQ ID NO: 436 (from top to bottom) in FIG. 2B, and SEQ ID NO: 437 and SEQ ID NO: 438 (from top to bottom) in FIG. 2C.
Figure 3:
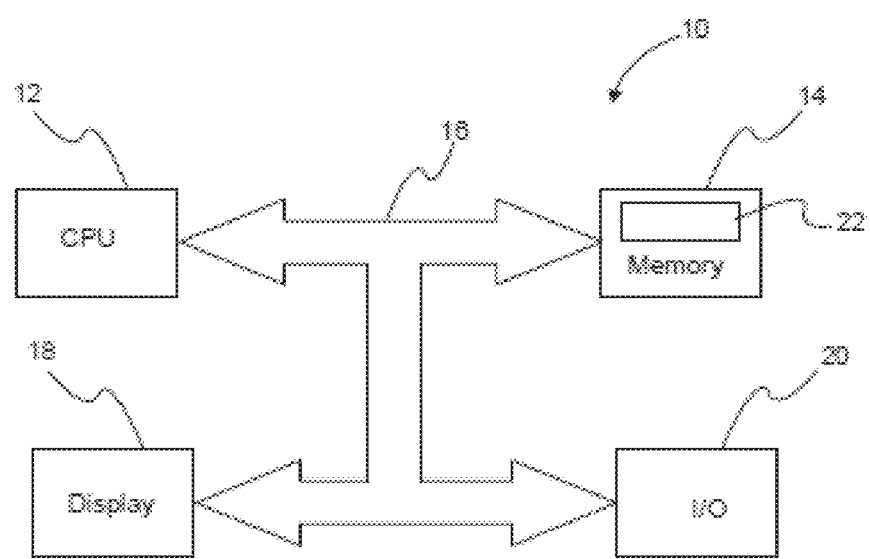
FIG. 3 is a schematic illustration of a computer system implementing an embodiment of the invention.

It was first determined whether such interactions are possible in the canonical miRNA-mRNA set of lin-4 and lin-14. The hybridizations of lin-4 and all previously suggested binding sites in 3'UTR of lin-14 were calculated using OMP software (DNA Software, Inc., Ann Arbor, Mich.). OMP calculates nucleotide thermodynamics using a nearest neighbor model that considers two adjacent nucleotides at a time to compute stability in terms of the Gibb's free energy ($\Delta G$) of double stranded formation. FIG. 2A shows the site with the lowest $\Delta G$ value (most stable) among them. Most of the predicted binding structures are different from the sequence-based illustrative figure in Lee et al.'s paper (R. C. Lee, R. L. Feinbaum, and V. Ambros, The *C. elegans* heterochronic gene lin-4 encodes small RNAs with antisense complementarity to lin-14. Cell 75: 843-54 (1993)): the 3'end part of lin-4 does not interact with some of suggested binding sites in 3'UTR of lin-14. Next, a possible binding position was searched for between lin-4 and 5'UTR of lin-14. Since OMP calculates the binding structure based on $\Delta G$, identify the stable hybridization site could be identified (e.g., shown in FIG. 2B). Due to a bulge and G-U wobble, BLAST search or TargetScanS fail to find this pair. In order to reduce variables, flanking regions are excluded in the calculations. Since the software cannot compute three nucleotide strands together, artificial sequences were prepared having target-3'UTR and 5'UTR sequences on each side: the artificial mixed UTR has its 5'end side from 5'UTR and its 3'end side from 3'UTR sequences. As shown in FIGS. 2A and 2C, 3'UTR site and lin-4 hybridization is less stable than this mixed UTR and lin-4 case, and the $\Delta G$ difference between them is about 5 kcal/mol.

All miRNA and target mRNA sets were selected in *C. elegans* (e.g., shown in Table 1, pairs with experimentally validated functions/targets) to check if mixed UTR sequences exist in target mRNAs for a miRNA and if the differences ($\Delta\Delta G$) between $\Delta G$ of 3'UTR and miRNA ($\Delta G\_3$'UTR) and $\Delta G$ of mixed UTR and miRNA ($\Delta G\_$mixed UTR) are similar to 5 kcal/mol ($\Delta\Delta G=\Delta G\_3$'UTR$-\Delta G\_$mixed UTR). BLAST search was performed for the initial screen, followed by OMP calculation in-depth analysis. As shown in Table 2, all of them satisfy the criteria. To find if the mixed UTR is specific to miRNA-mRNA functional pairs, we checked the hybridization possibility of mixed UTR of cog-1 and four randomly chosen miRNAs (miR-273, miR-235, miR-353, and miR-1). None of them showed considerable hybridization possibility.

TABLE 2 the differences between $\Delta G\_3$'UTR and $\Delta G\_$mixed UTR

| miRNA | mRNA | $\Delta G\_3$'UTR (kcal/mol) | $\Delta G\_$mixed UTR (kcal/mol) | $\Delta\Delta G$ (kcal/mol) |
|---|---|---|---|---|
| lin-4 | lin-14 | −16.41 | −21.70 | 5.29 |
| lin-4 | lin-28 | −18.58 | −22.86 | 4.28 |
| let-7 | lin-41 | −10.76 | −15.29 | 4.53 |
| let-7 | hbl-1 | −13.97 | −20.01 | 6.04 |
| mir-273 | die-1 | −19.77 | −24.63 | 4.86 |
| lsy-6 | cog-1 | −11.79 | −20.23 | 8.44 |

Reporter gene assays have been used in target verification experiments. Most studies use luciferase as a reporter gene ligated to 3'UTR sequences of predicted target mRNAs. They co-transfect the vectors containing target sequence and reporter genes with putative functional miRNAs and measure the luciferase intensity changes. Only a few experiments measured mRNA expression together with luciferase intensity to distinguish translation repression (mRNA present but protein absent) from mRNA degradation (mRNA absent by RNA interference effect). Although an understanding of the mechanism is not necessary to practice the present invention and the present invention is not limited to any particular mechanism of action, based on the model of the present invention, if there are no complementary 5'UTR sequences to the miRNA 3'end region and the interaction between 3'UTR and miRNA is stable enough, there is a possibility of mRNA degradation by an enzymatic effect. Furthermore, when the sequence of the luciferase gene close to the 5' end region was analyzed, sites were found to accommodate let-7 miRNAs, the miRNA used in experiments measuring both mRNA and luciferase expression levels. Since, in some embodiments, the model of the present invention does not exclude miRNA bridging 3'UTR and the coding region sequences and the coding region starts almost immediately after the transcription starting site in the vectors used in the Kiriakidou et al. paper, models of the present invention do not contradict the reporter assay experiments.

Next, predicted targets generated by the methods of the present invention were compared with targets of other groups. As a preliminary study, only sequence similarity was used without considering thermodynamics. To study the sequence properties of miRNAs, all human miRNA sequences from the miRNA Registry was collected (S. Griffiths-Jones, The microRNA Registry. Nucleic Acids Res 32: D109-11 (2004)). From previous work by Lewis et al. B. P. Lewis, C. B. Burge, and D. P. Bartel, *Conserved seed pairing, often flanked by adenosines, indicates that thousands of human genes are microRNA targets. Cell* 120: 15-20 (2005)), ten transcripts were identified and predicted to be targeted by more than three miRNAs. For each of these transcripts, the 5'UTR and 3'UTR sequences were collected after making sure that their RefSeq annotations were given reviewed or validated status. A computational analysis was carried out to determine which miRNAs target each of the transcripts. Comparing with Lewis et al.'s dataset, 9 out of 10 genes were predicted to be targeted by at least one miRNA from them.

In order to estimate the false positive rates, each of the miRNAs were shuffled, maintaining the composition of original sequences, and the same analyses was repeated as for the original miRNA sequences. Only 3'UTR, only 5'UTR or both UTR regions were considered as targets, and for each case: 1) perfect canonical matches (A:U, G:C) or 2) canonical and G:U wobbles were searched for. The 5' ends of the miRNAs were assumed to pair with the 3'UTR regions and the 3'ends of the miRNAs with the 5'UTR regions.

Table 4 shows various scenarios that were taken into consideration. For each scenario, the UTR(s) considered, the presence or absence of G:U wobbles and the signal:noise ratio from the prediction are listed. The signal:noise ratio was calculated as the sum of the number of predicted miRNA-target relationships over the sum of the number of predicted shuffled miRNA-target relationships. As can be seen from the table, the consideration of 5' UTR sequences in target recognition, either by itself or along with 3'UTR sequences, significantly increases the signal:noise ratio. This analysis does not consider the thermodynamics of base-pairing between the miRNA and the target. If the free energy changes were considered an even more pronounced improvement in the signal to noise ratio would be expected.

TABLE 4

Signal to noise ratio of total human miRNAs searching targets among 10 human genes. Match sequences and considering regions are shown together.

| 5'UTR | 3'UTR | signal/noise |
|---|---|---|
|  | A:U, G:C, G:U | 0.98 |
|  | A:U, G:C | 1.47 |
| A:U, G:C, G:U |  | 0.98 |
| A:U, G:C |  | 1.77 |
| A:U, G:C, G:U | A:U, G:C, G:U | 1.08 |
| A:U, G:C, G:U | A:U, G:C | 1.69 |
| A:U, G:C | A:U, G:C | 2.67 |

With reference to FIG. 3, the present invention provides a computer system for determining mRNA sequences that are susceptible to regulation by microRNA. System 10 of the present invention includes central processing unit (CPU) 12, memory 14, and input/output interface 16. Computer system 10 communicates with display 18 and input devices 20 such as a keyboard and mouse via interface 16. In one variation, memory 14 includes one or more of the following: random access memory (RAM), read only memory (ROM), CDROM, DVD, flasch drive, disk drive, tape drive and the like. The method of various embodiments is implemented by routine 22 that is stored in memory 14 and executed by the CPU 12.

Figure 4:
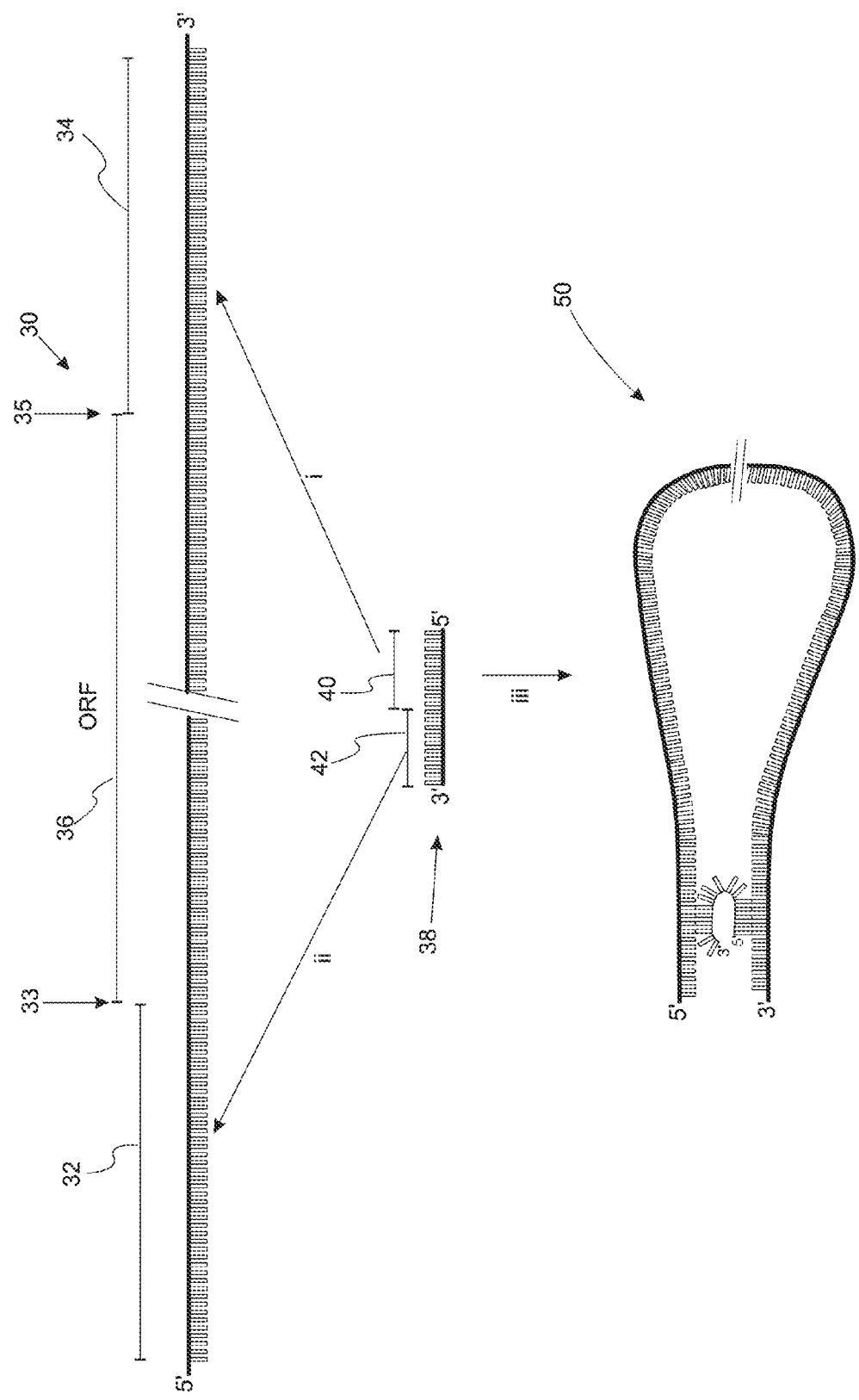
FIG. 4 is a schematic flowchart illustrating an embodiment of the invention.

With reference to FIG. 4, the method implemented by routine 22 includes a step of receiving data identifying an mRNA nucleotide sequence 30 representing a gene or portions thereof. Candidate mRNA sequences can be downloaded from http://www.ncbi.nlm.nih.gov/. Characteristically, the nucleotide sequence has a region 32 that is upstream of translation start site 33, a section 34 that is downstream of translation stop site 35, and an open reading frame 36. The method also includes a step of receiving data identifying a set of microRNA (miRNA) nucleotide sequences. Candidate miRNA sequences can be downloaded from http://mirbase.org/ftp.shtml. Each microRNA sequence 38 in the set has 5' miRNA section 40 and a 3' miRNA section 42. In step i), section 34 is evaluated for sub-regions that are capable of stable hybridizing to at least of a portion of 5' miRNA section 40. In general, one or more portions of section 40 and one or more sub-sections of section 34 are evaluated. In one refinement, stable hybridization is determine by the degree of complementariness of miRNA section 40 to a sub-region of section 34 with perfect complementary sub-regions of section 34 being the most stable. In another refinement, stable hybridization is determined by thermodynamic criteria. Specifically, the change $\Delta G$ in Gibbs free energy for the interaction of a portion of 5' miRNA section 40 with sub-regions of section 34 is evaluated with interactions having $\Delta G$ less than a predetermined value being identified as candidate sites for in vivo interactions. In a further refinement, $\Delta G$ for these hybridizations is less than about $-10$ kcal/mol. In still a further refinement, $\Delta G$ for these hybridizations is less than about $-13$ kcal/mol. The thermodynamic calculation may be carried out using the RNAhybrid™ software available from http://bibiserv.techfak.uni-bielefeld.de/rnahybrid/.

Still referring to FIG. 4, in step ii), section 32 is evaluated for sub-regions that are capable of stable hybridizing to at least of a portion of 3' miRNA section 42. In general, one or more portions of 3' miRNA section 42 and one or more sub-sections of section 32 are evaluated. In one refinement, stable hybridization is determine by the degree of complementariness of 3'miRNA section 42 to a sub-region of section 32 with perfect complementary sub-regions of section 32 being the most stable. In another refinement, stable hybridization is determined by thermodynamic criteria. Specifically, the change $\Delta G$ in Gibbs free energy for the interaction of a portion of 3' miRNA section 42 with sub-regions of section 32 is evaluated with interactions having $\Delta G$ less than a predetermined value being identified as candidate sites for in vivo interactions. In a further refinement, $\Delta G$ for these hybridizations is less than about $-10$ kcal/mol. In still a further refinement, $\Delta G$ for these hybridizations is less than about $-13$ kcal/mol. In still a further refinement, $\Delta G$ for these hybridizations is less than about $-14$ kcal/mol. In yet another refinement, section 32 includes an AUG motif that intereacts with one or more portions of 3' miRNA section 42 as described in more detail in the examples below.

In step iii), combinations of stably hybridizing sub-regions of section 34 to portions of 5' miRNA section 40 and stably hybridizing sub-regions of section 32 to portions of 3' miRNA section 42 are used to identify candidates 50 for microRNA-mRNA complexes. In an optional subsequent step, the miRNA is introduced into a cell expressisng the mRNA to verify regulation of the mRNA by the miRNA. In a variation, a nucleic acid sequence (e.g., antisense-miRNA, microRNA sponge, anti-miR, etc) that blocks miRNA is introduced into a cell expressing the mRNA to verify regulation of the mRNA by the miRNA.

Figure 5:
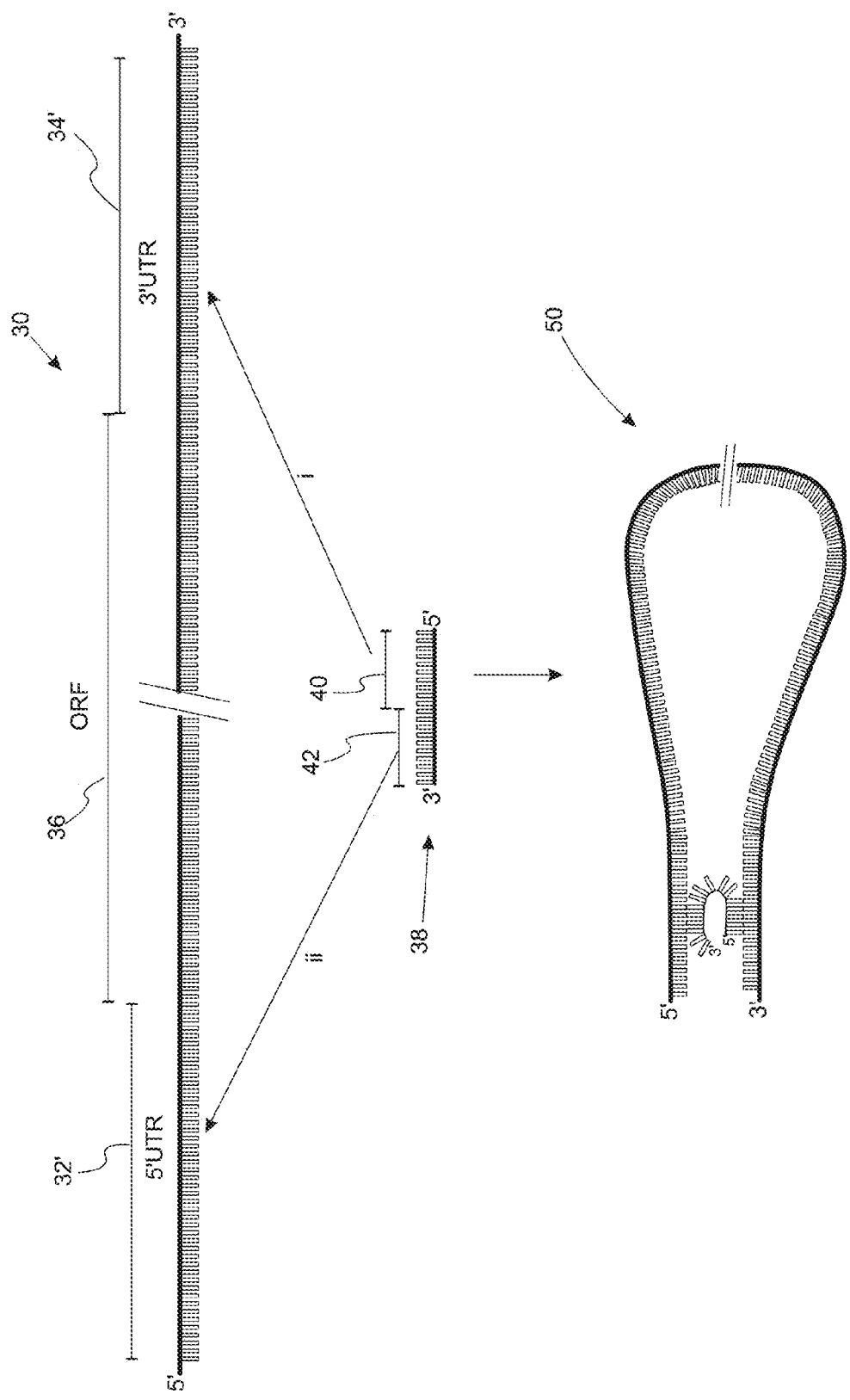
FIG. 5 is a schematic flowchart illustrating an embodiment of the invention.

With reference to FIG. 5, the method implemented by routine 22 includes a step of receiving data identifying an mRNA nucleotide sequence 30 representing a gene. Characteristically, the nucleotide sequence has a 5' untranslated region (UTR) section 32', a 3' UTR section 34', and an open reading frame 36. The method also includes a step of receiving data identifying a microRNA nucleotide sequence 38. The microRNA (miRNA) sequence has 5' miRNA section 40 and a 3' miRNA section 42. In step i), 3' UTR section 34' is evaluated for sub-regions that are capable of stable hybridizing to at least of a portion of 5' miRNA section 40. In general, one or more portions of 5' miRNA section 40 and one or more sub-sections of 3' UTR section 34' are evaluated. In one refinement, stable hybridization is determine by the degree of complementariness of miRNA section 40 to a sub-region of 3' UTR section 34' with perfect complementary sub-regions of 3' UTR section 34' being the most stable. In another refinement, stable hybridization is determined by thermodynamic criteria. Specifically, the change $\Delta G$ in Gibbs free energy for the interaction of a portion of 5' miRNA section 40 with sub-regions of 3' UTR section 34' is evaluated with interactions having $\Delta G$ less than a predetermined value being identified as candidate sites for in vivo interactions. In a further refinement, $\Delta G$ for these hybridizations is less than or equal to about $-10$ kcal/mol. In still a further refinement, $\Delta G$ for these hybridizations is less than or equal to about $-13$ kcal/mol.

Still referring to FIG. 5, in step ii), 5' UTR section 32' is evaluated for sub-regions that are capable of stable hybridizing to at least of a portion of 3' miRNA section 42. In general, one or more portions of 3' miRNA section 42 and one or more sub-sections of 5' UTR section 32' are evaluated. In one refinement, stable hybridization is determine by the degree of complementariness of 3'miRNA section 42 to a sub-region of 5' UTR section 32' with perfect complementary sub-regions of 5' UTR section 32' being the most stable. In another refinement, stable hybridization is determined by thermodynamic criteria. Specifically, the change $\Delta G$ in Gibbs free energy for the interaction of a portion of 3' miRNA section 42 with sub-regions of 5' UTR section 32' is evaluated with interactions having $\Delta G$ less than a predetermined value being identified as candidate sites for in vivo interactions. In a further refinement, $\Delta G$ for these hybridizations is less than or equal to about $-10$ kcal/mol. In still a further refinement, $\Delta G$ for these hybridizations is less than or equal to about $-13$ kcal/mol. In another variation, the mRNA has an AUG motif that intereacts with one or more portions of 3' miRNA section.

In step iii), combinations of stably hybridizing sub-regions of 3' UTR section 34' to portions of 5' miRNA section 40 and stably hybridizing sub-regions of 5' UTR section 32' to portions of 3' miRNA section 42 are used to identify candidates 50 for microRNA-mRNA complexes. In a subsequent step, the miRNA is introduced into a cell expressisng the mRNA to verify regulation of the mRNA by the miRNA. In a variation, a nucleic acid sequence (e.g., antisense-miRNA, microRNA sponge, anti-miR, etc) that blocks miRNA is introduced into a cell expressing the mRNA to verify regulation of the mRNA by the miRNA.

Additional details of the present invention are found in the article *New class of microRNA targets containing simultaneous 5'-UTR and 3'-UTR interaction*, I. Lee et al., Genome Research, 19:1175-1183 (2008). The entire disclosure of which is hereby incorporated by reference. Moreover, additional applications of the methods of the invention are found in PCT application no. PCT/US11/25726 entitled MIRFILTER: EFFICIENT NOISE REDUCTION METHOD TO IDENTIFY MIRNA AND TARGET GENE NETWORKS FROM GENOME-WIDE EXPRESSION DATA filed on Feb. 22, 2011, the entire disclosure of which is hereby incorporated by reference.

In another variation, a non-transitory computer readable medium embodying a program of instructions executable by a processor to perform the method steps set forth above is provided. Specifically, the computer readable medium is encoded with instructions for the steps of the methods of the invention. Example of useful computer readable media include, but are not limited to, harddrives, floppy drives, CDROM, DVD, optical drives, random acess medium, and the like.

EXPERIMENTAL

The following examples are provided in order to demonstrate and further illustrate certain preferred embodiments and aspects of the present invention and are not to be construed as limiting the scope thereof.

Example 1 findmiRNA and findTarget Programs

In some embodiments, the present invention provides the following programs: findmiRNA and findTarget. FindmiRNA predicts targets and orders them by gene. This is beneficial when there are very few UTR's in the UTR file. For example, this program can be used when one is looking for all the miRNAs that target a particular gene. FindTarget predicts targets and orders them by microRNA. This is usually beneficial when there are very few microRNAs in the miRNA file. For example, if one is looking for all the UTRs that are targeted by a particular miRNA, then this would be the program of choice. In some embodiments, the order in which the UTR files and the miRNA files are specified in both programs is followed.

Exemplary program formats and code are provided below. One of skill in the art will appreciate that the same or similar results can be encoded a variety of different ways.

1. findMiRNA:

Usage:

./findMiRNA-U 8-K <kmersize> —M mismatch.txt miRNA.fna 5UTR.txt 3UTR.txt Options:

-U <number>—This is a default setting that specifies that both UTRs have to be searched Other versions may include the capability of searching the 5' or 3' UTRs or both.

-K <number>—This indicates the word size to be used to build the search tree and for the search routine. Preferably, but not limited to, 6-8.

-M<file> —This specifies the filename that contains the mismatches that are considered while looking for targets in preferred embodiments. This must be specified 2. findTarget Usage:

./findTarget-U 8-K<kmersize> —M mismatch.txt miRNA.fna 5UTR.txt 3UTR.txt

The options are the same as for findMiRNA. However this program has the added feature of NOT specifying the '-M' option, which would then tell the program to look for perfect matches alone.

Example 2

Find miRNA Program Source Code

Example 3 findTarget Program Source Code

Example 4 miRNA Input

```
>ref|NM_100000|hsa-let-7a MIMAT0000062 Homo sapiens let-7a
                                                    SEQ ID NO: 1
TGAGGTAGTAGGTTGTATAGTT >ref|NM_100001|hsa-let-7b MIMAT0000063 Homo sapiens let-7b
                                                    SEQ ID NO: 2
TGAGGTAGTAGGTTGTGTGGTT >ref|NM_100002|hsa-let-7c MIMAT0000064 Homo sapiens let-7c
                                                    SEQ ID NO: 3
TGAGGTAGTAGGTTGTATGGTT >ref|NM_100003|hsa-let-7d MIMAT0000065 Homo sapiens let-7d
                                                    SEQ ID NO: 4
AGAGGTAGTAGGTTGCATAGT >ref|NM_100004|hsa-let-7e MIMAT0000066 Homo sapiens let-7e
                                                    SEQ ID NO: 5
TGAGGTAGGAGGTTGTATAGT >ref|NM_100005|hsa-let-7f MIMAT0000067 Homo sapiens let-7f
                                                    SEQ ID NO: 6
TGAGGTAGTAGATTGTATAGTT >ref|NM_100006|hsa-miR-15a MIMAT0000068 Homo sapiens miR-15a
                                                    SEQ ID NO: 7
TAGCAGCACATAATGGTTTGTG >ref|NM_100007|hsa-miR-16 MIMAT0000069 Homo sapiens miR-16
                                                    SEQ ID NO: 8
TAGCAGCACGTAAATATTGGCG >ref|NM_100008|hsa-miR-17-5p MIMAT0000070 Homo sapiens miR-17-5p
                                                    SEQ ID NO: 9
CAAAGTGCTTACAGTGCAGGTAGT >ref|NM_100009|hsa-miR-17-3p MIMAT0000071 Homo sapiens miR-17-3p
                                                    SEQ ID NO: 10
ACTGCAGTGAAGGCACTTGT >ref|NM_100010|hsa-miR-18a MIMAT0000072 Homo sapiens miR-18a
                                                    SEQ ID NO: 11
TAAGGTGCATCTAGTGCAGATA >ref|NM_100011|hsa-miR-19a MIMAT0000073 Homo sapiens miR-19a
                                                    SEQ ID NO: 12
TGTGCAAATCTATGCAAAACTGA >ref|NM_100012|hsa-miR-19b MIMAT0000074 Homo sapiens miR-19b
                                                    SEQ ID NO: 13
TGTGCAAATCCATGCAAAACTGA >ref|NM_100013|hsa-miR-20a MIMAT0000075 Homo sapiens miR-20a
                                                    SEQ ID NO: 14
TAAAGTGCTTATAGTGCAGGTAG >ref|NM_100014|hsa-miR-21 MIMAT0000076 Homo sapiens miR-21
                                                    SEQ ID NO: 15
TAGCTTATCAGACTGATGTTGA >ref|NM_100015|hsa-miR-22 MIMAT0000077 Homo sapiens miR-22
                                                    SEQ ID NO: 16
```

AAGCTGCCAGTTGAAGAACTGT

>ref|NM_100016|hsa-miR-23a MIMAT0000078 Homo sapiens miR-23a
                                                          SEQ ID NO: 17
ATCACATTGCCAGGGATTTCC >ref|NM_100017|hsa-miR-189 MIMAT0000079 Homo sapiens miR-189
                                                          SEQ ID NO: 18
GTGCCTACTGAGCTGATATCAGT >ref|NM_100018|hsa-miR-24 MIMAT0000080 Homo sapiens miR-24
                                                          SEQ ID NO: 19
TGGCTCAGTTCAGCAGGAACAG >ref|NM_100019|hsa-miR-25 MIMAT0000081 Homo sapiens miR-25
                                                          SEQ ID NO: 20
CATTGCACTTGTCTCGGTCTGA >ref|NM_100020|hsa-miR-26a MIMAT0000082 Homo sapiens miR-26a
                                                          SEQ ID NO: 21
TTCAAGTAATCCAGGATAGGC >ref|NM_100021|hsa-miR-26b MIMAT0000083 Homo sapiens miR-26b
                                                          SEQ ID NO: 22
TTCAAGTAATTCAGGATAGGTT >ref|NM_100022|hsa-miR-27a MIMAT0000084 Homo sapiens miR-27a
                                                          SEQ ID NO: 23
TTCACAGTGGCTAAGTTCCGC >ref|NM_100023|hsa-miR-28 MIMAT0000085 Homo sapiens miR-28
                                                          SEQ ID NO: 24
AAGGAGCTCACAGTCTATTGAG >ref|NM_100024|hsa-miR-29a MIMAT0000086 Homo sapiens miR-29a
                                                          SEQ ID NO: 25
TAGCACCATCTGAAATCGGTT >ref|NM_100025|hsa-miR-30a-5p MIMAT0000087 Homo sapiens miR-30a-5p
                                                          SEQ ID NO: 26
TGTAAACATCCTCGACTGGAAG >ref|NM_100026|hsa-miR-30a-3p MIMAT0000088 Homo sapiens miR-30a-3p
                                                          SEQ ID NO: 27
CTTTCAGTCGGATGTTTGCAGC >ref|NM_100027|hsa-miR-31 MIMAT0000089 Homo sapiens miR-31
                                                          SEQ ID NO: 28
GGCAAGATGCTGGCATAGCTG >ref|NM_100028|hsa-miR-32 MIMAT0000090 Homo sapiens miR-32
                                                          SEQ ID NO: 29
TATTGCACATTACTAAGTTGC >ref|NM_100029|hsa-miR-33 MIMAT0000091 Homo sapiens miR-33
                                                          SEQ ID NO: 30
GTGCATTGTAGTTGCATTG >ref|NM_100030|hsa-miR-92 MIMAT0000092 Homo sapiens miR-92
                                                          SEQ ID NO: 31
TATTGCACTTGTCCCGGCCTG >ref|NM_100031|hsa-miR-93 MIMAT0000093 Homo sapiens miR-93
                                                          SEQ ID NO: 32
AAAGTGCTGTTCGTGCAGGTAG >ref|NM_100032|hsa-miR-95 MIMAT0000094 Homo sapiens miR-95
                                                          SEQ ID NO: 33
TTCAACGGGTATTTATTGAGCA >ref|NM_100033|hsa-miR-96 MIMAT0000095 Homo sapiens miR-96
                                                          SEQ ID NO: 34
TTTGGCACTAGCACATTTTTGC >ref|NM_100034|hsa-miR-98 MIMAT0000096 Homo sapiens miR-98
                                                          SEQ ID NO: 35
TGAGGTAGTAAGTTGTATTGTT >ref|NM_100035|hsa-miR-99a MIMAT0000097 Homo sapiens miR-99a
                                                          SEQ ID NO: 36

```
                                   -continued
AACCCGTAGATCCGATCTTGTG

>ref|NM_100036|hsa-miR-100 MIMAT0000098 Homo sapiens miR-100
                                                          SEQ ID NO: 37
AACCCGTAGATCCGAACTTGTG >ref|NM_100037|hsa-miR-101 MIMAT0000099 Homo sapiens miR-101
                                                          SEQ ID NO: 38
TACAGTACTGTGATAACTGAAG >ref|NM_100038|hsa-miR-29b MIMAT0000100 Homo sapiens miR-29b
                                                          SEQ ID NO: 39
TAGCACCATTTGAAATCAGTGTT >ref|NM_100039|hsa-miR-103 MIMAT0000101 Homo sapiens miR-103
                                                          SEQ ID NO: 40
AGCAGCATTGTACAGGGCTATGA >ref|NM_100040|hsa-miR-105 MIMAT0000102 Homo sapiens miR-105
                                                          SEQ ID NO: 41
TCAAATGCTCAGACTCCTGT >ref|NM_100041|hsa-miR-106a MIMAT0000103 Homo sapiens miR-106a
                                                          SEQ ID NO: 42
AAAAGTGCTTACAGTGCAGGTAGC >ref|NM_100042|hsa-miR-107 MIMAT0000104 Homo sapiens miR-107
                                                          SEQ ID NO: 43
AGCAGCATTGTACAGGGCTATCA >ref|NM_100043|hsa-miR-192 MIMAT0000222 Homo sapiens miR-192
                                                          SEQ ID NO: 44
CTGACCTATGAATTGACAGCC >ref|NM_100044|hsa-miR-196a MIMAT0000226 Homo sapiens miR-196a
                                                          SEQ ID NO: 45
TAGGTAGTTTCATGTTGTTGG >ref|NM_100045|hsa-miR-197 MIMAT0000227 Homo sapiens miR-197
                                                          SEQ ID NO: 46
TTCACCACCTTCTCCACCCAGC >ref|NM_100046|hsa-miR-198 MIMAT0000228 Homo sapiens miR-198
                                                          SEQ ID NO: 47
GGTCCAGAGGGGAGATAGG >ref|NM_100047|hsa-miR-199a MIMAT0000231 Homo sapiens miR-199a
                                                          SEQ ID NO: 48
CCCAGTGTTCAGACTACCTGTTC >ref|NM_100048|hsa-miR-199a* MIMAT0000232 Homo sapiens miR-199a*
                                                          SEQ ID NO: 49
TACAGTAGTCTGCACATTGGTT >ref|NM_100049|hsa-miR-208 MIMAT0000241 Homo sapiens miR-208
                                                          SEQ ID NO: 50
ATAAGACGAGCAAAAAGCTTGT >ref|NM_100050|hsa-miR-129 MIMAT0000242 Homo sapiens miR-129
                                                          SEQ ID NO: 51
CTTTTTGCGGTCTGGGCTTGC >ref|NM_100051|hsa-miR-148a MIMAT0000243 Homo sapiens miR-148a
                                                          SEQ ID NO: 52
TCAGTGCACTACAGAACTTTGT >ref|NM_100052|hsa-miR-30c MIMAT0000244 Homo sapiens miR-30c
                                                          SEQ ID NO: 53
TGTAAACATCCTACACTCTCAGC >ref|NM_100053|hsa-miR-30d MIMAT0000245 Homo sapiens miR-30d
                                                          SEQ ID NO: 54
TGTAAACATCCCCGACTGGAAG >ref|NM_100054|hsa-miR-139 MIMAT0000250 Homo sapiens miR-139
                                                          SEQ ID NO: 55
TCTACAGTGCACGTGTCT >ref|NM_100055|hsa-miR-147 MIMAT0000251 Homo sapiens miR-147
                                                          SEQ ID NO: 56
GTGTGTGGAAATGCTTCTGC
```

```
>ref|NM_100056|hsa-miR-7 MIMAT0000252 Homo sapiens miR-7
                                                  SEQ ID NO: 57
TGGAAGACTAGTGATTTTGTTG >ref|NM_100057|hsa-miR-10a MIMAT0000253 Homo sapiens miR-10a
                                                  SEQ ID NO: 58
TACCCTGTAGATCCGAATTTGTG >ref|NM_100058|hsa-miR-10b MIMAT0000254 Homo sapiens miR-10b
                                                  SEQ ID NO: 59
TACCCTGTAGAACCGAATTTGT >ref|NM_100059|hsa-miR-34a MIMAT0000255 Homo sapiens miR-34a
                                                  SEQ ID NO: 60
TGGCAGTGTCTTAGCTGGTTGTT >ref|NM_100060|hsa-miR-181a MIMAT0000256 Homo sapiens miR-181a
                                                  SEQ ID NO: 61
AACATTCAACGCTGTCGGTGAGT >ref|NM_100061|hsa-miR-181b MIMAT0000257 Homo sapiens miR-181b
                                                  SEQ ID NO: 62
AACATTCATTGCTGTCGGTGGG >ref|NM_100062|hsa-miR-181c MIMAT0000258 Homo sapiens miR-181c
                                                  SEQ ID NO: 63
AACATTCAACCTGTCGGTGAGT >ref|NM_100063|hsa-miR-182 MIMAT0000259 Homo sapiens miR-182
                                                  SEQ ID NO: 64
TTTGGCAATGGTAGAACTCACA >ref|NM_100064|hsa-miR-182* MIMAT0000260 Homo sapiens miR-182*
                                                  SEQ ID NO: 65
TGGTTCTAGACTTGCCAACTA >ref|NM_100065|hsa-miR-183 MIMAT0000261 Homo sapiens miR-183
                                                  SEQ ID NO: 66
TATGGCACTGGTAGAATTCACTG >ref|NM_100066|hsa-miR-187 MIMAT0000262 Homo sapiens miR-187
                                                  SEQ ID NO: 67
TCGTGTCTTGTGTTGCAGCCG >ref|NM_100067|hsa-miR-199b MIMAT0000263 Homo sapiens miR-199b
                                                  SEQ ID NO: 68
CCCAGTGTTTAGACTATCTGTTC >ref|NM_100068|hsa-miR-203 MIMAT0000264 Homo sapiens miR-203
                                                  SEQ ID NO: 69
GTGAAATGTTTAGGACCACTAG >ref|NM_100069|hsa-miR-204 MIMAT0000265 Homo sapiens miR-204
                                                  SEQ ID NO: 70
TTCCCTTTGTCATCCTATGCCT >ref|NM_100070|hsa-miR-205 MIMAT0000266 Homo sapiens miR-205
                                                  SEQ ID NO: 71
TCCTTCATTCCACCGGAGTCTG >ref|NM_100071|hsa-miR-210 MIMAT0000267 Homo sapiens miR-210
                                                  SEQ ID NO: 72
CTGTGCGTGTGACAGCGGCTGA >ref|NM_100072|hsa-miR-211 MIMAT0000268 Homo sapiens miR-211
                                                  SEQ ID NO: 73
TTCCCTTTGTCATCCTTCGCCT >ref|NM_100073|hsa-miR-212 MIMAT0000269 Homo sapiens miR-212
                                                  SEQ ID NO: 74
TAACAGTCTCCAGTCACGGCC >ref|NM_100074|hsa-miR-213 MIMAT0000270 Homo sapiens miR-213
                                                  SEQ ID NO: 75
ACCATCGACCGTTGATTGTACC >ref|NM_100075|hsa-miR-214 MIMAT0000271 Homo sapiens miR-214
                                                  SEQ ID NO: 76
ACAGCAGGCACAGACAGGCAG
```

```
>ref|NM_100076|hsa-miR-215 MIMAT0000272 Homo sapiens miR-215
                                                         SEQ ID NO: 77
ATGACCTATGAATTGACAGAC >ref|NM_100077|hsa-miR-216 MIMAT0000273 Homo sapiens miR-216
                                                         SEQ ID NO: 78
TAATCTCAGCTGGCAACTGTG >ref|NM_100078|hsa-miR-217 MIMAT0000274 Homo sapiens miR-217
                                                         SEQ ID NO: 79
TACTGCATCAGGAACTGATTGGAT >ref|NM_100079|hsa-miR-218 MIMAT0000275 Homo sapiens miR-218
                                                         SEQ ID NO: 80
TTGTGCTTGATCTAACCATGT >ref|NM_100080|hsa-miR-219 MIMAT0000276 Homo sapiens miR-219
                                                         SEQ ID NO: 81
TGATTGTCCAAACGCAATTCT >ref|NM_100081|hsa-miR-220 MIMAT0000277 Homo sapiens miR-220
                                                         SEQ ID NO: 82
CCACACCGTATCTGACACTTT >ref|NM_100082|hsa-miR-221 MIMAT0000278 Homo sapiens miR-221
                                                         SEQ ID NO: 83
AGCTACATTGTCTGCTGGGTTTC >ref|NM_100083|hsa-miR-222 MIMAT0000279 Homo sapiens miR-222
                                                         SEQ ID NO: 84
AGCTACATCTGGCTACTGGGTCTC >ref|NM_100084|hsa-miR-223 MIMAT0000280 Homo sapiens miR-223
                                                         SEQ ID NO: 85
TGTCAGTTTGTCAAATACCCC >ref|NM_100085|hsa-miR-224 MIMAT0000281 Homo sapiens miR-224
                                                         SEQ ID NO: 86
CAAGTCACTAGTGGTTCCGTTTA >ref|NM_100086|hsa-miR-200b MIMAT0000318 Homo sapiens miR-200b
                                                         SEQ ID NO: 87
TAATACTGCCTGGTAATGATGAC >ref|NM_100087|hsa-let-7g MIMAT0000414 Homo sapiens let-7g
                                                         SEQ ID NO: 88
TGAGGTAGTAGTTTGTACAGT >ref|NM_100088|hsa-let-7i MIMAT0000415 Homo sapiens let-7i
                                                         SEQ ID NO: 89
TGAGGTAGTAGTTTGTGCTGT >ref|NM_100089|hsa-miR-1 MIMAT0000416 Homo sapiens miR-1
                                                         SEQ ID NO: 90
TGGAATGTAAAGAAGTATGTA >ref|NM_100090|hsa-miR-15b MIMAT0000417 Homo sapiens miR-15b
                                                         SEQ ID NO: 91
TAGCAGCACATCATGGTTTACA >ref|NM_100091|hsa-miR-23b MIMAT0000418 Homo sapiens miR-23b
                                                         SEQ ID NO: 92
ATCACATTGCCAGGGATTACC >ref|NM_100092|hsa-miR-27b MIMAT0000419 Homo sapiens miR-27b
                                                         SEQ ID NO: 93
TTCACAGTGGCTAAGTTCTGC >ref|NM_100093|hsa-miR-30b MIMAT0000420 Homo sapiens miR-30b
                                                         SEQ ID NO: 94
TGTAAACATCCTACACTCAGCT >ref|NM_100094|hsa-miR-122a MIMAT0000421 Homo sapiens miR-122a
                                                         SEQ ID NO: 95
TGGAGTGTGACAATGGTGTTTGT >ref|NM_100095|hsa-miR-124a MIMAT0000422 Homo sapiens miR-124a
                                                         SEQ ID NO: 96
TTAAGGCACGCGGTGAATGCCA >ref|NM_100096|hsa-miR-125b MIMAT0000423 Homo sapiens miR-125b
```

-continued

```
                                                      SEQ ID NO: 97
TCCCTGAGACCCTAACTTGTGA

>ref|NM_100097|hsa-miR-128a MIMAT0000424 Homo sapiens miR-128a
                                                      SEQ ID NO: 98
TCACAGTGAACCGGTCTCTTTT >ref|NM_100098|hsa-miR-130a MIMAT0000425 Homo sapiens miR-130a
                                                      SEQ ID NO: 99
CAGTGCAATGTTAAAAGGGCAT >ref|NM_100099|hsa-miR-132 MIMAT0000426 Homo sapiens miR-132
                                                      SEQ ID NO: 100
TAACAGTCTACAGCCATGGTCG >ref|NM_100100|hsa-miR-133a MIMAT0000427 Homo sapiens miR-133a
                                                      SEQ ID NO: 101
TTGGTCCCCTTCAACCAGCTGT >ref|NM_100101|hsa-miR-135a MIMAT0000428 Homo sapiens miR-135a
                                                      SEQ ID NO: 102
TATGGCTTTTTATTCCTATGTGA >ref|NM_100102|hsa-miR-137 MIMAT0000429 Homo sapiens miR-137
                                                      SEQ ID NO: 103
TATTGCTTAAGAATACGCGTAG >ref|NM_100103|hsa-miR-138 MIMAT0000430 Homo sapiens miR-138
                                                      SEQ ID NO: 104
AGCTGGTGTTGTGAATC >ref|NM_100104|hsa-miR-140 MIMAT0000431 Homo sapiens miR-140
                                                      SEQ ID NO: 105
AGTGGTTTTACCCTATGGTAG >ref|NM_100105|hsa-miR-141 MIMAT0000432 Homo sapiens miR-141
                                                      SEQ ID NO: 106
TAACACTGTCTGGTAAAGATGG >ref|NM_100106|hsa-miR-142-5p MIMAT0000433 Homo sapiens miR-142-5p
                                                      SEQ ID NO: 107
CATAAAGTAGAAAGCACTAC >ref|NM_100107|hsa-miR-142-3p MIMAT0000434 Homo sapiens miR-142-3p
                                                      SEQ ID NO: 108
TGTAGTGTTTCCTACTTTATGGA >ref|NM_100108|hsa-miR-143 MIMAT0000435 Homo sapiens miR-143
                                                      SEQ ID NO: 109
TGAGATGAAGCACTGTAGCTCA >ref|NM_100109|hsa-miR-144 MIMAT0000436 Homo sapiens miR-144
                                                      SEQ ID NO: 110
TACAGTATAGATGATGTACTAG >ref|NM_100110|hsa-miR-145 MIMAT0000437 Homo sapiens miR-145
                                                      SEQ ID NO: 111
GTCCAGTTTTCCCAGGAATCCCTT >ref|NM_100111|hsa-miR-152 MIMAT0000438 Homo sapiens miR-152
                                                      SEQ ID NO: 112
TCAGTGCATGACAGAACTTGGG >ref|NM_100112|hsa-miR-153 MIMAT0000439 Homo sapiens miR-153
                                                      SEQ ID NO: 113
TTGCATAGTCACAAAAGTGA >ref|NM_100113|hsa-miR-191 MIMAT0000440 Homo sapiens miR-191
                                                      SEQ ID NO: 114
CAACGGAATCCCAAAAGCAGCT >ref|NM_100114|hsa-miR-191* MIMAT0001618 Homo sapiens miR-191*
                                                      SEQ ID NO: 115
GCTGCGCTTGGATTTCGTCCCC >ref|NM_100115|hsa-miR-9 MIMAT0000441 Homo sapiens miR-9
                                                      SEQ ID NO: 116
TCTTTGGTTATCTAGCTGTATGA >ref|NM_100116|hsa-miR-9* MIMAT0000442 Homo sapiens miR-9*
                                                      SEQ ID NO: 117
```

-continued

TAAAGCTAGATAACCGAAAGT

>ref|NM_100117|hsa-miR-125a MIMAT0000443 Homo sapiens miR-125a
                                                  SEQ ID NO: 118
TCCCTGAGACCCTTTAACCTGTG >ref|NM_100118|hsa-miR-126* MIMAT0000444 Homo sapiens miR-126*
                                                  SEQ ID NO: 119
CATTATTACTTTTGGTACGCG >ref|NM_100119|hsa-miR-126 MIMAT0000445 Homo sapiens miR-126
                                                  SEQ ID NO: 120
TCGTACCGTGAGTAATAATGC >ref|NM_100120|hsa-miR-127 MIMAT0000446 Homo sapiens miR-127
                                                  SEQ ID NO: 121
TCGGATCCGTCTGAGCTTGGCT >ref|NM_100121|hsa-miR-134 MIMAT0000447 Homo sapiens miR-134
                                                  SEQ ID NO: 122
TGTGACTGGTTGACCAGAGGG >ref|NM_100122|hsa-miR-136 MIMAT0000448 Homo sapiens miR-136
                                                  SEQ ID NO: 123
ACTCCATTTGTTTTGATGATGGA >ref|NM_100123|hsa-miR-146a MIMAT0000449 Homo sapiens miR-146a
                                                  SEQ ID NO: 124
TGAGAACTGAATTCCATGGGTT >ref|NM_100124|hsa-miR-149 MIMAT0000450 Homo sapiens miR-149
                                                  SEQ ID NO: 125
TCTGGCTCCGTGTCTTCACTCC >ref|NM_100125|hsa-miR-150 MIMAT0000451 Homo sapiens miR-150
                                                  SEQ ID NO: 126
TCTCCCAACCCTTGTACCAGTG >ref|NM_100126|hsa-miR-154 MIMAT0000452 Homo sapiens miR-154
                                                  SEQ ID NO: 127
TAGGTTATCCGTGTTGCCTTCG >ref|NM_100127|hsa-miR-154* MIMAT0000453 Homo sapiens miR-154*
                                                  SEQ ID NO: 128
AATCATACACGGTTGACCTATT >ref|NM_100128|hsa-miR-184 MIMAT0000454 Homo sapiens miR-184
                                                  SEQ ID NO: 129
TGGACGGAGAACTGATAAGGGT >ref|NM_100129|hsa-miR-185 MIMAT0000455 Homo sapiens miR-185
                                                  SEQ ID NO: 130
TGGAGAGAAAGGCAGTTC >ref|NM_100130|hsa-miR-186 MIMAT0000456 Homo sapiens miR-186
                                                  SEQ ID NO: 131
CAAAGAATTCTCCTTTTGGGCTT >ref|NM_100131|hsa-miR-188 MIMAT0000457 Homo sapiens miR-188
                                                  SEQ ID NO: 132
CATCCCTTGCATGGTGGAGGGT >ref|NM_100132|hsa-miR-190 MIMAT0000458 Homo sapiens miR-190
                                                  SEQ ID NO: 133
TGATATGTTTGATATATTAGGT >ref|NM_100133|hsa-miR-193a MIMAT0000459 Homo sapiens miR-193a
                                                  SEQ ID NO: 134
AACTGGCCTACAAAGTCCCAG >ref|NM_100134|hsa-miR-194 MIMAT0000460 Homo sapiens miR-194
                                                  SEQ ID NO: 135
TGTAACAGCAACTCCATGTGGA >ref|NM_100135|hsa-miR-195 MIMAT0000461 Homo sapiens miR-195
                                                  SEQ ID NO: 136
TAGCAGCACAGAAATATTGGC >ref|NM_100136|hsa-miR-206 MIMAT0000462 Homo sapiens miR-206
                                                  SEQ ID NO: 137
TGGAATGTAAGGAAGTGTGTGG -continued >ref|NM_100137|hsa-miR-320 MIMAT0000510 Homo sapiens miR-320
SEQ ID NO: 138
AAAAGCTGGGTTGAGAGGGCGAA >ref|NM_100138|hsa-miR-200c MIMAT0000617 Homo sapiens miR-200c
SEQ ID NO: 139
TAATACTGCCGGGTAATGATGG >ref|NM_100139|hsa-miR-155 MIMAT0000646 Homo sapiens miR-155
SEQ ID NO: 140
TTAATGCTAATCGTGATAGGGG >ref|NM_100140|hsa-miR-128b MIMAT0000676 Homo sapiens miR-128b
SEQ ID NO: 141
TCACAGTGAACCGGTCTCTTTC >ref|NM_100141|hsa-miR-106b MIMAT0000680 Homo sapiens miR-106b
SEQ ID NO: 142
TAAAGTGCTGACAGTGCAGAT >ref|NM_100142|hsa-miR-29c MIMAT0000681 Homo sapiens miR-29c
SEQ ID NO: 143
TAGCACCATTTGAAATCGGT >ref|NM_100143|hsa-miR-200a* MIMAT0001620 Homo sapiens miR-200a*
SEQ ID NO: 144
CATCTTACCGGACAGTGCTGGA >ref|NM_100144|hsa-miR-200a MIMAT0000682 Homo sapiens miR-200a
SEQ ID NO: 145
TAACACTGTCTGGTAACGATGT >ref|NM_100145|hsa-miR-302a* MIMAT0000683 Homo sapiens miR-302a*
SEQ ID NO: 146
TAAACGTGGATGTACTTGCTTT >ref|NM_100146|hsa-miR-302a MIMAT0000684 Homo sapiens miR-302a
SEQ ID NO: 147
TAAGTGCTTCCATGTTTTGGTGA >ref|NM_100147|hsa-miR-34b MIMAT0000685 Homo sapiens miR-34b
SEQ ID NO: 148
TAGGCAGTGTCATTAGCTGATTG >ref|NM_100148|hsa-miR-34c MIMAT0000686 Homo sapiens miR-34c
SEQ ID NO: 149
AGGCAGTGTAGTTAGCTGATTGC >ref|NM_100149|hsa-miR-299-5p MIMAT0000687 Homo sapiens miR-299-5p
SEQ ID NO: 150
TGGTTTACCGTCCCACATACAT >ref|NM_100150|hsa-miR-299-3p MIMAT0000687 Homo sapiens miR-299-3p
SEQ ID NO: 151
TATGTGGGATGGTAAACCGCTT >ref|NM_100151|hsa-miR-301 MIMAT0000688 Homo sapiens miR-301
SEQ ID NO: 152
CAGTGCAATAGTATTGTCAAAGC >ref|NM_100152|hsa-miR-99b MIMAT0000689 Homo sapiens miR-99b
SEQ ID NO: 153
CACCCGTAGAACCGACCTTGCG >ref|NM_100153|hsa-miR-296 MIMAT0000690 Homo sapiens miR-296
SEQ ID NO: 154
AGGGCCCCCCCTCAATCCTGT >ref|NM_100154|hsa-miR-130b MIMAT0000691 Homo sapiens miR-130b
SEQ ID NO: 155
CAGTGCAATGATGAAAGGGCAT >ref|NM_100155|hsa-miR-30e-5p MIMAT0000692 Homo sapiens miR-30e-5p
SEQ ID NO: 156
TGTAAACATCCTTGACTGGA >ref|NM_100156|hsa-miR-30e-3p MIMAT0000693 Homo sapiens miR-30e-3p
SEQ ID NO: 157
CTTTCAGTCGGATGTTTACAGC -continued >ref|NM_100157|hsa-miR-361 MIMAT0000703 Homo sapiens miR-361
SEQ ID NO: 158
TTATCAGAATCTCCAGGGGTAC >ref|NM_100158|hsa-miR-362 MIMAT0000705 Homo sapiens miR-362
SEQ ID NO: 159
AATCCTTGGAACCTAGGTGTGAG >ref|NM_100159|hsa-miR-363 MIMAT0000707 Homo sapiens miR-363
SEQ ID NO: 160
ATTGCACGGTATCCATCTGTAA >ref|NM_100160|hsa-miR-365 MIMAT0000710 Homo sapiens miR-365
SEQ ID NO: 161
TAATGCCCCTAAAAATCCTTAT >ref|NM_100161|hsa-miR-302b* MIMAT0000714 Homo sapiens miR-302b*
SEQ ID NO: 162
ACTTTAACATGGAAGTGCTTTCT >ref|NM_100162|hsa-miR-302b MIMAT0000715 Homo sapiens miR-302b
SEQ ID NO: 163
TAAGTGCTTCCATGTTTTAGTAG >ref|NM_100163|hsa-miR-302c* MIMAT0000716 Homo sapiens miR-302c*
SEQ ID NO: 164
TTTAACATGGGGGTACCTGCTG >ref|NM_100164|hsa-miR-302c MIMAT0000717 Homo sapiens miR-302c
SEQ ID NO: 165
TAAGTGCTTCCATGTTTCAGTGG >ref|NM_100165|hsa-miR-302d MIMAT0000718 Homo sapiens miR-302d
SEQ ID NO: 166
TAAGTGCTTCCATGTTTGAGTGT >ref|NM_100166|hsa-miR-367 MIMAT0000719 Homo sapiens miR-367
SEQ ID NO: 167
AATTGCACTTTAGCAATGGTGA >ref|NM_100167|hsa-miR-368 MIMAT0000720 Homo sapiens miR-368
SEQ ID NO: 168
ACATAGAGGAAATTCCACGTTT >ref|NM_100168|hsa-miR-369-5p MIMAT0001621 Homo sapiens miR-369-5p
SEQ ID NO: 169
AGATCGACCGTGTTATATTCGC >ref|NM_100169|hsa-miR-369-3p MIMAT0000721 Homo sapiens miR-369-3p
SEQ ID NO: 170
AATAATACATGGTTGATCTTT >ref|NM_100170|hsa-miR-370 MIMAT0000722 Homo sapiens miR-370
SEQ ID NO: 171
GCCTGCTGGGGTGGAACCTGG >ref|NM_100171|hsa-miR-371 MIMAT0000723 Homo sapiens miR-371
SEQ ID NO: 172
GTGCCGCCATCTTTTGAGTGT >ref|NM_100172|hsa-miR-372 MIMAT0000724 Homo sapiens miR-372
SEQ ID NO: 173
AAAGTGCTGCGACATTTGAGCGT >ref|NM_100173|hsa-miR-373* MIMAT0000725 Homo sapiens miR-373*
SEQ ID NO: 174
ACTCAAAATGGGGGCGCTTTCC >ref|NM_100174|hsa-miR-373 MIMAT0000726 Homo sapiens miR-373
SEQ ID NO: 175
GAAGTGCTTCGATTTTGGGGTGT >ref|NM_100175|hsa-miR-374 MIMAT0000727 Homo sapiens miR-374
SEQ ID NO: 176
TTATAATACAACCTGATAAGTG >ref|NM_100176|hsa-miR-375 MIMAT0000728 Homo sapiens miR-375
SEQ ID NO: 177
TTTGTTCGTTCGGCTCGCGTGA >ref|NM_100177|hsa-miR-376a MIMAT0000729 Homo sapiens miR-376a -continued >ref|NM_100178|hsa-miR-377 MIMAT0000730 Homo sapiens miR-377
SEQ ID NO: 179
ATCACACAAAGGCAACTTTTGT >ref|NM_100179|hsa-miR-378 MIMAT0000731 Homo sapiens miR-378
SEQ ID NO: 180
CTCCTGACTCCAGGTCCTGTGT >ref|NM_100180|hsa-miR-422b MIMAT0000732 Homo sapiens miR-422b
SEQ ID NO: 181
CTGGACTTGGAGTCAGAAGGCC >ref|NM_100181|hsa-miR-379 MIMAT0000733 Homo sapiens miR-379
SEQ ID NO: 182
TGGTAGACTATGGAACGTA >ref|NM_100182|hsa-miR-380-5p MIMAT0000734 Homo sapiens miR-380-5p
SEQ ID NO: 183
TGGTTGACCATAGAACATGCGC >ref|NM_100183|hsa-miR-380-3p MIMAT0000735 Homo sapiens miR-380-3p
SEQ ID NO: 184
TATGTAATATGGTCCACATCTT >ref|NM_100184|hsa-miR-381 MIMAT0000736 Homo sapiens miR-381
SEQ ID NO: 185
TATACAAGGGCAAGCTCTCTGT >ref|NM_100185|hsa-miR-382 MIMAT0000737 Homo sapiens miR-382
SEQ ID NO: 186
GAAGTTGTTCGTGGTGGATTCG >ref|NM_100186|hsa-miR-383 MIMAT0000738 Homo sapiens miR-383
SEQ ID NO: 187
AGATCAGAAGGTGATTGTGGCT >ref|NM_100187|hsa-miR-340 MIMAT0000750 Homo sapiens miR-340
SEQ ID NO: 188
TCCGTCTCAGTTACTTTATAGCC >ref|NM_100188|hsa-miR-330 MIMAT0000751 Homo sapiens miR-330
SEQ ID NO: 189
GCAAAGCACACGGCCTGCAGAGA >ref|NM_100189|hsa-miR-328 MIMAT0000752 Homo sapiens miR-328
SEQ ID NO: 190
CTGGCCCTCTCTGCCCTTCCGT >ref|NM_100190|hsa-miR-342 MIMAT0000753 Homo sapiens miR-342
SEQ ID NO: 191
TCTCACACAGAAATCGCACCCGTC >ref|NM_100191|hsa-miR-337 MIMAT0000754 Homo sapiens miR-337
SEQ ID NO: 192
TCCAGCTCCTATATGATGCCTTT >ref|NM_100192|hsa-miR-323 MIMAT0000755 Homo sapiens miR-323
SEQ ID NO: 193
GCACATTACACGGTCGACCTCT >ref|NM_100193|hsa-miR-326 MIMAT0000756 Homo sapiens miR-326
SEQ ID NO: 194
CCTCTGGGCCCTTCCTCCAG >ref|NM_100194|hsa-miR-151 MIMAT0000757 Homo sapiens miR-151
SEQ ID NO: 195
ACTAGACTGAAGCTCCTTGAGG >ref|NM_100195|hsa-miR-135b MIMAT0000758 Homo sapiens miR-135b
SEQ ID NO: 196
TATGGCTTTTCATTCCTATGTG >ref|NM_100196|hsa-miR-148b MIMAT0000759 Homo sapiens miR-148b
SEQ ID NO: 197
TCAGTGCATCACAGAACTTTGT >ref|NM_100197|hsa-miR-331 MIMAT0000760 Homo sapiens miR-331
SEQ ID NO: 198

-continued

GCCCCTGGGCCTATCCTAGAA

>ref|NM_100198|hsa-miR-324-5p MIMAT0000761 Homo sapiens miR-324-5p
SEQ ID NO: 199
CGCATCCCCTAGGGCATTGGTGT >ref|NM_100199|hsa-miR-324-3p MIMAT0000762 Homo sapiens miR-324-3p
SEQ ID NO: 200
CCACTGCCCCAGGTGCTGCTGG >ref|NM_100200|hsa-miR-338 MIMAT0000763 Homo sapiens miR-338
SEQ ID NO: 201
TCCAGCATCAGTGATTTTGTTGA >ref|NM_100201|hsa-miR-339 MIMAT0000764 Homo sapiens miR-339
SEQ ID NO: 202
TCCCTGTCCTCCAGGAGCTCA >ref|NM_100202|hsa-miR-335 MIMAT0000765 Homo sapiens miR-335
SEQ ID NO: 203
TCAAGAGCAATAACGAAAAATGT >ref|NM_100203|hsa-miR-133b MIMAT0000770 Homo sapiens miR-133b
SEQ ID NO: 204
TTGGTCCCCTTCAACCAGCTA >ref|NM_100204|hsa-miR-325 MIMAT0000771 Homo sapiens miR-325
SEQ ID NO: 205
CCTAGTAGGTGTCCAGTAAGTGT >ref|NM_100205|hsa-miR-345 MIMAT0000772 Homo sapiens miR-345
SEQ ID NO: 206
TGCTGACTCCTAGTCCAGGGC >ref|NM_100206|hsa-miR-346 MIMAT0000773 Homo sapiens miR-346
SEQ ID NO: 207
TGTCTGCCCGCATGCCTGCCTCT >ref|NM_100207|hsa-miR-384 MIMAT0001075 Homo sapiens miR-384
SEQ ID NO: 208
ATTCCTAGAAATTGTTCATA >ref|NM_100208|hsa-miR-196b MIMAT0001080 Homo sapiens miR-196b
SEQ ID NO: 209
TAGGTAGTTTCCTGTTGTTGG >ref|NM_100209|hsa-miR-422a MIMAT0001339 Homo sapiens miR-422a
SEQ ID NO: 210
CTGGACTTAGGGTCAGAAGGCC >ref|NM_100210|hsa-miR-423 MIMAT0001340 Homo sapiens miR-423
SEQ ID NO: 211
AGCTCGGTCTGAGGCCCCTCAG >ref|NM_100211|hsa-miR-424 MIMAT0001341 Homo sapiens miR-424
SEQ ID NO: 212
CAGCAGCAATTCATGTTTTGAA >ref|NM_100212|hsa-miR-425 MIMAT0001343 Homo sapiens miR-425
SEQ ID NO: 213
ATCGGGAATGTCGTGTCCGCC >ref|NM_100213|hsa-miR-18b MIMAT0001412 Homo sapiens miR-18b
SEQ ID NO: 214
TAAGGTGCATCTAGTGCAGTTA >ref|NM_100214|hsa-miR-20b MIMAT0001413 Homo sapiens miR-20b
SEQ ID NO: 215
CAAAGTGCTCATAGTGCAGGTAG >ref|NM_100215|hsa-miR-448 MIMAT0001532 Homo sapiens miR-448
SEQ ID NO: 216
TTGCATATGTAGGATGTCCCAT >ref|NM_100216|hsa-miR-429 MIMAT0001536 Homo sapiens miR-429
SEQ ID NO: 217
TAATACTGTCTGGTAAAACCGT >ref|NM_100217|hsa-miR-449 MIMAT0001541 Homo sapiens miR-449
SEQ ID NO: 218
TGGCAGTGTATTGTTAGCTGGT -continued

```
>ref|NM_100218|hsa-miR-450 MIMAT0001545 Homo sapiens miR-450
                                                       SEQ ID NO: 219
TTTTTGCGATGTGTTCCTAATA >ref|NM_100219|hsa-miR-431 MIMAT0001625 Homo sapiens miR-431
                                                       SEQ ID NO: 220
TGTCTTGCAGGCCGTCATGCA >ref|NM_100220|hsa-miR-433 MIMAT0001627 Homo sapiens miR-433
                                                       SEQ ID NO: 221
ATCATGATGGGCTCCTCGGTGT >ref|NM_100221|hsa-miR-329 MIMAT0001629 Homo sapiens miR-329
                                                       SEQ ID NO: 222
AACACACCTGGTTAACCTCTTT >ref|NM_100222|hsa-miR-453 MIMAT0001630 Homo sapiens miR-453
                                                       SEQ ID NO: 223
GAGGTTGTCCGTGGTGAGTTCG >ref|NM_100223|hsa-miR-451 MIMAT0001631 Homo sapiens miR-451
                                                       SEQ ID NO: 224
AAACCGTTACCATTACTGAGTTT >ref|NM_100224|hsa-miR-452 MIMAT0001635 Homo sapiens miR-452
                                                       SEQ ID NO: 225
TGTTTGCAGAGGAAACTGAGAC >ref|NM_100225|hsa-miR-452* MIMAT0001636 Homo sapiens miR-452*
                                                       SEQ ID NO: 226
TCAGTCTCATCTGCAAAGAAG >ref|NM_100226|hsa-miR-409-5p MIMAT0001638 Homo sapiens miR-409-5p
                                                       SEQ ID NO: 227
AGGTTACCCGAGCAACTTTGCA >ref|NM_100227|hsa-miR-409-3p MIMAT0001639 Homo sapiens miR-409-3p
                                                       SEQ ID NO: 228
CGAATGTTGCTCGGTGAACCCCT >ref|NM_100228|hsa-miR-412 MIMAT0002170 Homo sapiens miR-412
                                                       SEQ ID NO: 229
ACTTCACCTGGTCCACTAGCCGT >ref|NM_100229|hsa-miR-410 MIMAT0002171 Homo sapiens miR-410
                                                       SEQ ID NO: 230
AATATAACACAGATGGCCTGTT >ref|NM_100230|hsa-miR-376b MIMAT0002172 Homo sapiens miR-376b
                                                       SEQ ID NO: 231
ATCATAGAGGAAAATCCATGTT >ref|NM_100231|hsa-miR-485-5p MIMAT0002175 Homo sapiens miR-485-5p
                                                       SEQ ID NO: 232
AGAGGCTGGCCGTGATGAATTC >ref|NM_100232|hsa-miR-485-3p MIMAT0002176 Homo sapiens miR-485-3p
                                                       SEQ ID NO: 233
GTCATACACGGCTCTCCTCT >ref|NM_100233|hsa-miR-488 MIMAT0002804 Homo sapiens miR-488
                                                       SEQ ID NO: 234
CCCAGATAATGGCACTCTCAA >ref|NM_100234|hsa-miR-489 MIMAT0002805 Homo sapiens miR-489
                                                       SEQ ID NO: 235
AGTGACATCACATATACGGCAGC >ref|NM_100235|hsa-miR-490 MIMAT0002806 Homo sapiens miR-490
                                                       SEQ ID NO: 236
CAACCTGGAGGACTCCATGCTG >ref|NM_100236|hsa-miR-491 MIMAT0002807 Homo sapiens miR-491
                                                       SEQ ID NO: 237
AGTGGGGAACCCTTCCATGAGGA >ref|NM_100237|hsa-miR-511 MIMAT0002808 Homo sapiens miR-511
                                                       SEQ ID NO: 238
GTGTCTTTTGCTCTGCAGTCA
```

-continued

```
>ref|NM_100238|hsa-miR-146b MIMAT0002809 Homo sapiens miR-146b
                                                      SEQ ID NO: 239
TGAGAACTGAATTCCATAGGCT >ref|NM_100239|hsa-miR-202* MIMAT0002810 Homo sapiens miR-202*
                                                      SEQ ID NO: 240
TTTCCTATGCATATACTTCTTT >ref|NM_100240|hsa-miR-202 MIMAT0002811 Homo sapiens miR-202
                                                      SEQ ID NO: 241
AGAGGTATAGGGCATGGGAAAA >ref|NM_100241|hsa-miR-492 MIMAT0002812 Homo sapiens miR-492
                                                      SEQ ID NO: 242
AGGACCTGCGGGACAAGATTCTT >ref|NM_100242|hsa-miR-493 MIMAT0002813 Homo sapiens miR-493
                                                      SEQ ID NO: 243
TTGTACATGGTAGGCTTTCATT >ref|NM_100243|hsa-miR-432 MIMAT0002814 Homo sapiens miR-432
                                                      SEQ ID NO: 244
TCTTGGAGTAGGTCATTGGGTGG >ref|NM_100244|hsa-miR-432* MIMAT0002815 Homo sapiens miR-432*
                                                      SEQ ID NO: 245
CTGGATGGCTCCTCCATGTCT >ref|NM_100245|hsa-miR-494 MIMAT0002816 Homo sapiens miR-494
                                                      SEQ ID NO: 246
TGAAACATACACGGGAAACCTCTT >ref|NM_100246|hsa-miR-495 MIMAT0002817 Homo sapiens miR-495
                                                      SEQ ID NO: 247
AAACAAACATGGTGCACTTCTTT >ref|NM_100247|hsa-miR-496 MIMAT0002818 Homo sapiens miR-496
                                                      SEQ ID NO: 248
ATTACATGGCCAATCTC >ref|NM_100248|hsa-miR-193b MIMAT0002819 Homo sapiens miR-193b
                                                      SEQ ID NO: 249
AACTGGCCCTCAAAGTCCCGCTTT >ref|NM_100249|hsa-miR-497 MIMAT0002820 Homo sapiens miR-497
                                                      SEQ ID NO: 250
CAGCAGCACACTGTGGTTTGT >ref|NM_100250|hsa-miR-181d MIMAT0002821 Homo sapiens miR-181d
                                                      SEQ ID NO: 251
AACATTCATTGTTGTCGGTGGGTT >ref|NM_100251|hsa-miR-512-5p MIMAT0002822 Homo sapiens miR-512-5p
                                                      SEQ ID NO: 252
CACTCAGCCTTGAGGGCACTTTC >ref|NM_100252|hsa-miR-512-3p MIMAT0002823 Homo sapiens miR-512-3p
                                                      SEQ ID NO: 253
AAGTGCTGTCATAGCTGAGGTC >ref|NM_100253|hsa-miR-498 MIMAT0002824 Homo sapiens miR-498
                                                      SEQ ID NO: 254
TTTCAAGCCAGGGGGCGTTTTC >ref|NM_100254|hsa-miR-520e MIMAT0002825 Homo sapiens miR-520e
                                                      SEQ ID NO: 255
AAAGTGCTTCCTTTTTGAGGG >ref|NM_100255|hsa-miR-515-5p MIMAT0002826 Homo sapiens miR-515-5p
                                                      SEQ ID NO: 256
TTCTCCAAAAGAAAGCACTTTCTG >ref|NM_100256|hsa-miR-515-3p MIMAT0002827 Homo sapiens miR-515-3p
                                                      SEQ ID NO: 257
GAGTGCCTTCTTTTGGAGCGT >ref|NM_100257|hsa-miR-519e* MIMAT0002828 Homo sapiens miR-519e*
                                                      SEQ ID NO: 258
TTCTCCAAAAGGGAGCACTTTC >ref|NM_100258|hsa-miR-519e MIMAT0002829 Homo sapiens miR-519e
```

-continued

```
                                              SEQ ID NO: 259
AAAGTGCCTCCTTTTAGAGTGT

>ref|NM_100259|hsa-miR-520f MIMAT0002830 Homo sapiens miR-520f
                                              SEQ ID NO: 260
AAGTGCTTCCTTTTAGAGGGTT >ref|NM_100260|hsa-miR-526c MIMAT0002831 Homo sapiens miR-526c
                                              SEQ ID NO: 261
CTCTAGAGGGAAGCGCTTTCTGTT >ref|NM_100261|hsa-miR-519c MIMAT0002832 Homo sapiens miR-519c
                                              SEQ ID NO: 262
AAAGTGCATCTTTTAGAGGAT >ref|NM_100262|hsa-miR-520a* MIMAT0002833 Homo sapiens miR-520a*
                                              SEQ ID NO: 263
CTCCAGAGGGAAGTACTTTCT >ref|NM_100263|hsa-miR-520a MIMAT0002834 Homo sapiens miR-520a
                                              SEQ ID NO: 264
AAAGTGCTTCCCTTTGGACTGT >ref|NM_100264|hsa-miR-526b MIMAT0002835 Homo sapiens miR-526b
                                              SEQ ID NO: 265
CTCTTGAGGGAAGCACTTTCTGTT >ref|NM_100265|hsa-miR-526b* MIMAT0002836 Homo sapiens miR-526b*
                                              SEQ ID NO: 266
AAAGTGCTTCCTTTTAGAGGC >ref|NM_100266|hsa-miR-519b MIMAT0002837 Homo sapiens miR-519b
                                              SEQ ID NO: 267
AAAGTGCATCCTTTTAGAGGTTT >ref|NM_100267|hsa-miR-525 MIMAT0002838 Homo sapiens miR-525
                                              SEQ ID NO: 268
CTCCAGAGGGATGCACTTTCT >ref|NM_100268|hsa-miR-525* MIMAT0002839 Homo sapiens miR-525*
                                              SEQ ID NO: 269
GAAGGCGCTTCCCTTTAGAGC >ref|NM_100269|hsa-miR-523 MIMAT0002840 Homo sapiens miR-523
                                              SEQ ID NO: 270
AACGCGCTTCCCTATAGAGGG >ref|NM_100270|hsa-miR-518f* MIMAT0002841 Homo sapiens miR-518f*
                                              SEQ ID NO: 271
CTCTAGAGGGAAGCACTTTCTCT >ref|NM_100271|hsa-miR-518f MIMAT0002842 Homo sapiens miR-518f
                                              SEQ ID NO: 272
AAAGCGCTTCTCTTTAGAGGA >ref|NM_100272|hsa-miR-520b MIMAT0002843 Homo sapiens miR-520b
                                              SEQ ID NO: 273
AAAGTGCTTCCTTTTAGAGGG >ref|NM_100273|hsa-miR-518b MIMAT0002844 Homo sapiens miR-518b
                                              SEQ ID NO: 274
CAAAGCGCTCCCCTTTAGAGGT >ref|NM_100274|hsa-miR-526a MIMAT0002845 Homo sapiens miR-526a
                                              SEQ ID NO: 275
CTCTAGAGGGAAGCACTTTCT >ref|NM_100275|hsa-miR-520c MIMAT0002846 Homo sapiens miR-520c
                                              SEQ ID NO: 276
AAAGTGCTTCCTTTTAGAGGGTT >ref|NM_100276|hsa-miR-518c* MIMAT0002847 Homo sapiens miR-518c*
                                              SEQ ID NO: 277
TCTCTGGAGGGAAGCACTTTCTG >ref|NM_100277|hsa-miR-518c MIMAT0002848 Homo sapiens miR-518c
                                              SEQ ID NO: 278
CAAAGCGCTTCTCTTTAGAGTG >ref|NM_100278|hsa-miR-524* MIMAT0002849 Homo sapiens miR-524*
                                              SEQ ID NO: 279
```

CTACAAAGGGAAGCACTTTCTC

>ref|NM_100279|hsa-miR-524 MIMAT0002850 Homo sapiens miR-524
SEQ ID NO: 280
GAAGGCGCTTCCCTTTGGAGT >ref|NM_100280|hsa-miR-517* MIMAT0002851 Homo sapiens miR-517*
SEQ ID NO: 281
CCTCTAGATGGAAGCACTGTCT >ref|NM_100281|hsa-miR-517a MIMAT0002852 Homo sapiens miR-517a
SEQ ID NO: 282
ATCGTGCATCCCTTTAGAGTGTT >ref|NM_100282|hsa-miR-519d MIMAT0002853 Homo sapiens miR-519d
SEQ ID NO: 283
CAAAGTGCCTCCCTTTAGAGTGT >ref|NM_100283|hsa-miR-521 MIMAT0002854 Homo sapiens miR-521
SEQ ID NO: 284
AACGCACTTCCCTTTAGAGTGT >ref|NM_100284|hsa-miR-520d* MIMAT0002855 Homo sapiens miR-520d*
SEQ ID NO: 285
TCTACAAAGGGAAGCCCTTTCTG >ref|NM_100285|hsa-miR-520d MIMAT0002856 Homo sapiens miR-520d
SEQ ID NO: 286
AAAGTGCTTCTCTTTGGTGGGTT >ref|NM_100286|hsa-miR-517b MIMAT0002857 Homo sapiens miR-517b
SEQ ID NO: 287
TCGTGCATCCCTTTAGAGTGTT >ref|NM_100287|hsa-miR-520g MIMAT0002858 Homo sapiens miR-520g
SEQ ID NO: 288
ACAAAGTGCTTCCCTTTAGAGTGT >ref|NM_100288|hsa-miR-516-5p MIMAT0002859 Homo sapiens miR-516-5p
SEQ ID NO: 289
ATCTGGAGGTAAGAAGCACTTT >ref|NM_100289|hsa-miR-516-3p MIMAT0002860 Homo sapiens miR-516-3p
SEQ ID NO: 290
TGCTTCCTTTCAGAGGGT >ref|NM_100290|hsa-miR-518e MIMAT0002861 Homo sapiens miR-518e
SEQ ID NO: 291
AAAGCGCTTCCCTTCAGAGTGT >ref|NM_100291|hsa-miR-527 MIMAT0002862 Homo sapiens miR-527
SEQ ID NO: 292
CTGCAAAGGGAAGCCCTTTCT >ref|NM_100292|hsa-miR-518a MIMAT0002863 Homo sapiens miR-518a
SEQ ID NO: 293
AAAGCGCTTCCCTTTGCTGGA >ref|NM_100293|hsa-miR-518d MIMAT0002864 Homo sapiens miR-518d
SEQ ID NO: 294
CAAAGCGCTTCCCTTTGGAGC >ref|NM_100294|hsa-miR-518a-2* MIMAT0002865 Homo sapiens miR-518a-2*
SEQ ID NO: 295
TCTGCAAAGGGAAGCCCTTT >ref|NM_100295|hsa-miR-517c MIMAT0002866 Homo sapiens miR-517c
SEQ ID NO: 296
ATCGTGCATCCTTTTAGAGTGT >ref|NM_100296|hsa-miR-520h MIMAT0002867 Homo sapiens miR-520h
SEQ ID NO: 297
ACAAAGTGCTTCCCTTTAGAGT >ref|NM_100297|hsa-miR-522 MIMAT0002868 Homo sapiens miR-522
SEQ ID NO: 298
AAAATGGTTCCCTTTAGAGTGTT >ref|NM_100298|hsa-miR-519a MIMAT0002869 Homo sapiens miR-519a
SEQ ID NO: 299
AAAGTGCATCCTTTTAGAGTGTTAC

```
>ref|NM_100299|hsa-miR-499 MIMAT0002870 Homo sapiens miR-499
                                              SEQ ID NO: 300
TTAAGACTTGCAGTGATGTTTAA >ref|NM_100300|hsa-miR-500 MIMAT0002871 Homo sapiens miR-500
                                              SEQ ID NO: 301
ATGCACCTGGGCAAGGATTCTG >ref|NM_100301|hsa-miR-501 MIMAT0002872 Homo sapiens miR-501
                                              SEQ ID NO: 302
AATCCTTTGTCCCTGGGTGAGA >ref|NM_100302|hsa-miR-502 MIMAT0002873 Homo sapiens miR-502
                                              SEQ ID NO: 303
ATCCTTGCTATCTGGGTGCTA >ref|NM_100303|hsa-miR-503 MIMAT0002874 Homo sapiens miR-503
                                              SEQ ID NO: 304
TAGCAGCGGGAACAGTTCTGCAG >ref|NM_100304|hsa-miR-504 MIMAT0002875 Homo sapiens miR-504
                                              SEQ ID NO: 305
AGACCCTGGTCTGCACTCTAT >ref|NM_100305|hsa-miR-505 MIMAT0002876 Homo sapiens miR-505
                                              SEQ ID NO: 306
GTCAACACTTGCTGGTTTCCTC >ref|NM_100306|hsa-miR-513 MIMAT0002877 Homo sapiens miR-513
                                              SEQ ID NO: 307
TTCACAGGGAGGTGTCATTTAT >ref|NM_100307|hsa-miR-506 MIMAT0002878 Homo sapiens miR-506
                                              SEQ ID NO: 308
TAAGGCACCCTTCTGAGTAGA >ref|NM_100308|hsa-miR-507 MIMAT0002879 Homo sapiens miR-507
                                              SEQ ID NO: 309
TTTTGCACCTTTTGGAGTGAA >ref|NM_100309|hsa-miR-508 MIMAT0002880 Homo sapiens miR-508
                                              SEQ ID NO: 310
TGATTGTAGCCTTTTGGAGTAGA >ref|NM_100310|hsa-miR-509 MIMAT0002881 Homo sapiens miR-509
                                              SEQ ID NO: 311
TGATTGGTACGTCTGTGGGTAGA >ref|NM_100311|hsa-miR-510 MIMAT0002882 Homo sapiens miR-510
                                              SEQ ID NO: 312
TACTCAGGAGAGTGGCAATCACA >ref|NM_100312|hsa-miR-514 MIMAT0002883 Homo sapiens miR-514
                                              SEQ ID NO: 313
ATTGACACTTCTGTGAGTAG
```

Example 5

Sample 3'UTR Input

```
>Hs_Capn6_3pUTR
                                              SEQ ID NO: 314
ATCTGCAATCCCAGAGAATCCTGACAAAGCGTGCCACCCTTTTATTTTCC
GTCAGGTGCCAGGTCTTAGTTAAGATTCACAATCTTTAGAAAGAATGAGA
TTCACAATAATTAACTCTTCCTCTCTTCTGATAAATTCCCCATACCTCCC
AATCCAAGTAGCATCTGTAGCTACATAACCTATATACCTCCAGCAGCTGG
ACATGGGGAGGCGACAGTCCTATCTAGACATCATACACATTTGCCAAGAA
AGGATCTCTGGGGCTTCCGGGGGTGAGATTCAAGTAGGACAATAACAAGA
GGCTGGACACCCTACAGATGTCTTTGATGTTTTCAGTTGTTTGATATATC
TCCCCTGTAGGGCATGTTGAGGAAGGAGGAGGGCTGATCAAGGCCAAGCT
GGTCTAGCCTGACATCCTAGCTCCTGACTGAACACTATAGACTTCCCAGC
AGCATTTCACCCAGCAGCCAGAGCCGGCTTTAAGTCCCCAACCCTTACAG
ACACCACTGCCACCACCACCAACCACGACCACCACCACCACCACCACTCA
CCACCATCATCACCTCCGGAAAGTGTAGTCCTGCCCTAACCCAAGTCACC
CCCGACAGTAAATTTTACCTTCATGTTGAGAAAGCTTCCTGGTGCTTAAT
CAAGAGCTGGAGTTCAATGAGTCCTAGACAGTGAGAGGGGCCTGAGCTTC
AGCTCAATGGAAGCCTGCTGTGTGCCACAAGACGGAAAAGTGGAAGAAGC
TGCAGTGGGAGACAAAGCCTCGGTCCCCCACCCATCCACACACACCTACA
CTCACACACGCGCACATGGGCGCGCACGAACTACCATTCAGGCAGTCAGT
```

```
GGGCAAGAGGAAAGATAAGTAAGTACCATACACACCTAAAAGATGAGAGA
ATTCATCCAGACATATTACAGCCAGTTTGGGGCCCCTGACTGCAATGTGA
AACCTCTCGCTGCTGCTAGGTTTACAAACAAGCCCATTGTCCTGTGCCTC
CTAATATCATTTGTACTGAAGACCCCATCTGGGGACTTGAGACTTTGGTC
CCAGCCCAGACTCCTCAGACTTTTCTCTCAGTTGGGATGCTTCACTCGCT
GGGGGTGTTTGTTTGCCCTCTCATTTTTCAGTACTTCTACAGAATTTTCT
CTAGAGTCAGTCATTATGAAATGTACTTCCCTCCATCTTAACCTATCAAC
TTTCTGCCCCTCCTTCAAGGCCCAGTATAAATGCCACCTCCTCCATGAAG
CCTTCCCTAATTCCACCCCAAACCCCCACCTTCAACAATATTTCAACGCT
TCTGCAATGATGAAAAGAAACATAGTTGTAGTACTTAGCCTACCTAGAC
CAGCAAGCATTCATTTTTAGCTCGCTCATTTTTTACCATGTTTTCCAGTC
TGTTTAACTTCTGCAGTGCCTTCACTACACTGCCTTACATAAACCAAATC
ACAATAAAGTTCATATTCAGTACA
```

>Hs_Dhrs8_3pUTR
SEQ ID NO: 315
```
GCACCTAGTTTTCTGAAAACTGATTTACCAGGTTTAGGTTGATGTCATCT
AATAGTGCCAGAATTTTAATGTTTGAACTTCTGTTTTTTCTAATTATCCC
CATTTCTTCAATATCATTTTTGAGGCTTTGGCAGTCTTCATTTACTACCA
CTTGTTCTTTAGCCAAAAGCTGATTACATATGATATAAACAGAGAAATAC
CTTTAGAGGTGACTTTAAGGAAAATGAAGAAAAAGAACCAAAATGACTTT
ATTAAAATAATTTCCAAGATTATTTGTGGCTCACCTGAAGGCTTTGCAAA
ATTTGTACCATAACCGTTTATTTAACATATATTTTTATTTTTGATTGCAC
TTAAATTTTGTATAATTTGTGTTTCTTTTTCTGTTCTACATAAAATCAGA
AACTTCAAGCTCTCTAAATAAAATGAAGGACTATATCTAGTGGTATTTCA
CAATGAATATCATGAACTCTCAATGGGTAGGTTTCATCCTACCCATTGCC
ACTCTGTTTCCTGAGAGATACCTCACATTCCAATGCCAAACATTTCTGCA
CAGGGAAGCTAGAGGTGGATACACGTGTTGCAAGTATAAAAGCATCACTG
GGATTTAAGGAGAATTGAGAGAATGTACCCACAAATGGCAGCAATAATAA
ATGGATCACACTT
```

>Hs_Ptpn1_3pUTR
SEQ ID NO: 316
```
CCTGACCCTCCTCCACTCCACCTCCACCCACTGTCCGCCTCTGCCCGCAG
AGCCCACGCCCGACTAGCAGGCATGCCGCGGTAGGTAAGGGCCGCCGGAC
CGCGTAGAGAGCCGGGCCCCGGACGGACGTTGGTTCTGCACTAAAACCCA
TCTTCCCCGGATGTGTGTCTCACCCCTCATCCTTTTACTTTTTGCCCCTT
CCACTTTGAGTACCAAATCCACAAGCCATTTTTTGAGGAGAGTGAAAGAG
AGTACCATGCTGGCGGCGCAGAGGGAAGGGGCCTACACCCGTCTTGGGGC
TCGCCCCACCCAGGGCTCCCTCCTGGAGCATCCCAGGCGGGCGGCACGCC
AACAGCCCCCCCTTGAATCTGCAGGGAGCAACTCTCCACTCCATATTTA
TTTAAACAATTTTTTCCCCAAAGGCATCCATAGTGCACTAGCATTTTCTT
GAACCAATAATGTATTAAAATTTTTTGATGTCAGCCTTGCATCAAGGGCT
TTATCAAAAAGTACAATAATAAATCCTCAGGTAGTACTGGGAATGGAAGG
CTTTGCCATGGGCCTGCTGCGTCAGACCAGTACTGGGAAGGAGGACGGTT
GTAAGCAGTTGTTATTTAGTGATATTGTGGGTAACGTGAGAAGATAGAAC
AATGCTATAATATATAATGAACACGTGGGTATTTAATAAGAAACATGATG
TGAGATTACTTTGTCCCGCTTATTCTCCTCCCTGTTATCTGCTAGATCTA
GTTCTCAATCACTGCTCCCCGTGTGTATTAGAATGCATGTAAGGTCTTC
TTGTGTCCTGATGAAAAATATGTGCTTGAAATGAGAAACTTTGATCTCTG
CTTACTAATGTGCCCCATGTCCAAGTCCAACCTGCCTGTGCATGACCTGA
TCATTACATGGCTGTGGTTCCTAAGCCTGTTGCTGAAGTCATTGTCGCTC
AGCAATAGGGTGCAGTTTTCCAGGAATAGGCATTTGCCTAATTCCTGGCA
TGACACTCTAGTGACTTCCTGGTGAGGCCCAGCCTGTCCTGGTACAGCAG
GGTCTTGCTGTAACTCAGACATTCCAAGGGTATGGGAAGCCATATTCACA
CCTCACGCTCTGGACATGATTTAGGGAAGCAGGGACACCCCCGCCCCCC
ACCTTTGGGATCAGCCTCCGCCATTCCAAGTCAACACTCTTCTTGAGCAG
ACCGTGATTTGGAAGAGAGGCACCTGCTGGAAACCACACTTCTTGAAACA
GCCTGGGTGACGGTCCTTTAGGCAGCCTGCCGCCGTCTCTGTCCCGGTTC
ACCTTGCCGAGAGAGGCGCGTCTGCCCCACCCTCAAACCCTGTGGGGCCT
GATGGTGCTCACGACTCTTCCTGCAAAGGGAACTGAAGACCTCCACATTA
AGTGGCTTTTAACATGAAAAACACGGCAGCTGTAGCTCCCGAGCTACTC
TCTTGCCAGCATTTTCACATTTTGCCTTTCTCGTGGTAGAAGCCAGTACA
GAGAAATTCTGTGGTGGGAACATTCGAGGTGTCACCCTGCAGAGCTATGG
TGAGGTGTGGATAAGGCTTAGGTGCCAGGCTGTAAGCATTCTGAGCTGGG
CTTGTTGTTTTAAGTCCTGTATATGTATGTAGTAGTTTGGGTGTGTATA
TATAGTAGCATTTCAAAATGGACGTACTGGTTTAACCTCCTATCCTTGGA
GAGCAGCTGGCTCTCCACCTTGTTACACATTATGTTAGAGAGGTAGCGAG
CTGCTCTGCTATATGCCTTAAGCCAATATTTACTCATCAGGTCATTATTT
TTTACAATGGCCATGGAATAAACCATTTTTAC
```

>Hs_Scarb1_3pUTR
SEQ ID NO: 317
```
GGTCCTGAGGACACCGTGAGCCAGCCAGGCCTGGCCGCTGGGCCTGACCG
GCCCCCAGCCCCTACACCCCGCTTCTCCCGGACTCTCCCAGCGGACAGC
CCCCCAGCCCCACAGCCTGAGCCTCCCAGCTGCCATGTGCCTGTTGCACA
CCTGCACACACGCCCTGGCACACATACACACATGCGTGCAGGCTTGTGCA
GACACTCAGGGATGGAGCTGCTGCTGAAGGGACTTGTAGGGAGAGGCTCG
TCAACAAGCACTGTTCTGGAACCTTCTCTCCACGTGGCCCACAGGCCTGA
CCACAGGGGCTGTGGGTCCTGCGTCCCCTTCCTCGGGTGAGCCTGGCCTG
TCCCGTTCAGCCGTTGGGCCCAGGCTTCCTCCCCTCCAAGGTGAAACACT
GCAGTCCCGGTGTGGTGGCTCCCCATGCAGGACGGGCCAGGCTGGGAGTG
CCGCCTTCCTGTGCCAAATTCAGTGGGGACTCAGTGCCCAGGCCCTGGCC
ACGAGCTTTGGCCTTGGTCTACCTGCCAGGCCAGGCAAAGCGCCTTTACA
CAGGCCTCGGAAAACAATGGAGTGAGCACAAGATGCCCTGTGCAGCTGCC
CGAGGGTCTCCGCCCACCCCGGCCGGACTTTGATCCCCCGAAGTCTTCA
CAGGCACTGCATCGGGTTGTCTGGCGCCCTTTTCCTCCAGCCTAAACTGA
```

-continued

CATCATCCTATGGACTGAGCCGGCCACTCTCTGGCCGAAGTGGCCGCAGG

CTGTGCCCCCGAGCTGCCCCCACCCCCTCACAGGGTCCCTCAGATTATAG

GTGCCCAGGCTGAGGTGAAGAGGCCTGGGGGCCCTGCCTTCCGGGCGCTC

CTGGACCCTGGGGCAAACCTGTGACCCTTTTCTACTGGAATAGAAATGAG

TTTTATCATCTTTGAAAAATAATTCACTCTTGAAGTAATAAACGTTTAAA

AAAATGG

Example 6

Sample 5' UTR Input

>Hs_Capn6_5pUTR
SEQ ID NO: 318
ATAGTTTTCAGGTTAAGAAAGCCAGAATCTTTGTTCAGCCACACTGACTG

AACAGACTTTTAGTGGGGTTACCTGGCTAACAGCAGCAGCGGCAACGGCA

GCAGCAGCAGCAGCAGCAGCAGCAGCAGCAGGGCTCCTGGGATAACT

CAGGCATAGTTCAACACT

>Hs_Dhrs8_5pUTR
SEQ ID NO: 319
CTCTCGCCCCTACTCTTTCTGGTGTTAGATCGAGCTACCCTCTAAAAGCA

GTTTAGAGTGGTAAAAAAAAAAAAAAACACACCAAACGCTCGCAGCCACA

AAAGGG

>Hs_Ptpn1_5pUTR
SEQ ID NO: 320
GTGATGCGTAGTTCCGGCTGCCGGTTGACATGAAGAAGCAGCAGCGGCTA

GGGCGGCGGTAGCTGCAGGGGTCGGGGATTGCAGCGGGCCTCGGGGCTAA

GAGCGCGACGCGGCCTAGAGCGGCAGACGGCGCAGTGGGCCGAGAAGGAG

GCGCAGCAGCCGCCCTGGCCCGTC

>Hs_Scarb1_5pUTR
SEQ ID NO: 321
GTCGCCGTCCCCGTCTCCTGCCAGGCGCGGAGCCCTGCGAGCCGCGGGTG

GGCCCCAGGCGCGCAGAC

Example 7

Sample Mismatch Input

G:T

Example 8

Sample output

```
*************************************************************
Query ID is >Hs_Capn6_5pUTR
*************************************************************
--------------------------------------------------------------
3' UTR region hits
--------------------------------------------------------------
>ref|NM_100165|hsa-miR-302d MIMAT0000718 Homo sapiens miR-
302d
Query:  1100    GCTTCACTCGCTGGGGGTGTTTG   SEQ ID NO: 322
                    ************
Mature miRNA    TGTGAGTTTGTACCTTCGTGAAT   SEQ ID NO: 323

--------------------------------------------------------------
5' UTR region hits
--------------------------------------------------------------
>ref|NM_100165|hsa-miR-302d MIMAT0000718 Homo sapiens miR-
302d
Query:  148     TAACTCAGGCATAGTTCAACACT   SEQ ID NO: 324
                        *********
Mature miRNA    TGTGAGTTTGTACCTTCGTGAAT   SEQ ID NO: 325

--------------------------------------------------------------
3' UTR region hits
--------------------------------------------------------------
>ref|NM_100307|hsa-miR-506 MIMAT0002878 Homo sapiens miR-
506
Query:  1101    TCACTCGCTGGGGGTGTTTGT     SEQ ID NO: 326
                       *********
Mature miRNA    AGATGAGTCTTCCCACGGAAT     SEQ ID NO: 327

--------------------------------------------------------------
5' UTR region hits
--------------------------------------------------------------
>ref|NM_100307|hsa-miR-506 MIMAT0002878 Homo sapiens miR-
506
Query:  30      TTTGTTCAGCCACACTGACTG     SEQ ID NO: 328
                       *********
Mature miRNA    AGATGAGTCTTCCCACGGAAT     SEQ ID NO: 329

--------------------------------------------------------------
3' UTR region hits
--------------------------------------------------------------
```

-continued

>ref|NM_100263|hsa-miR-520a MIMAT0002834 *Homo sapiens* miR-520a
Query: 1101    CTTCACTCGCTGGGGGTGTTTG     SEQ ID NO: 330
                  **********
Mature miRNA   TGTCAGGTTTCCCTTCGTGAAA     SEQ ID NO: 331

---

5' UTR region hits
---

>ref|NM_100263|hsa-miR-520a MIMAT0002834 *Homo sapiens* miR-520a
Query: 156     ATAGTTCAACACT              SEQ ID NO: 332
                  *********
Mature miRNA   TGTCAGGTTTCCCTTCGTGAAA     SEQ ID NO: 333

---

3' UTR region hits
---

>ref|NM_100292|hsa-miR-518a MIMAT0002863 *Homo sapiens* miR-518a
Query: 1101    TTCACTCGCTGGGGGTGTTTG      SEQ ID NO: 334
                  *********
Mature miRNA   AGGTCGTTTCCCTTCGCGAAA      SEQ ID NO: 335

---

5' UTR region hits
---

>ref|NM_100292|hsa-miR-518a MIMAT0002863 *Homo sapiens* miR-518a
Query: 59      TTTAGTGGGGTTACCTGGCTA      SEQ ID NO: 336
                  **********
Mature miRNA   AGGTCGTTTCCCTTCGCGAAA      SEQ ID NO: 337

***************************************************************
Query ID is >Hs_Dhrs8_5pUTR
***************************************************************

---

3' UTR region hits
---

>ref|NM_100180|hsa-miR-422b MIMAT0000732 *Homo sapiens* miR-422b
Query: 28      AAAACTGATTTACCAGGTTTAG     SEQ ID NO: 338
                  **********
Mature miRNA   CCGGAAGACTGAGGTTCAGGTC     SEQ ID NO: 339

---

5' UTR region hits
---

>ref|NM_100180|hsa-miR-422b MIMAT0000732 *Homo sapiens* miR-422b
Query: 15      CTCTTTCTGGTGTTAGATCGAG     SEQ ID NO: 340
                  *********
Mature miRNA   CCGGAAGACTGAGGTTCAGGTC     SEQ ID NO: 341

***************************************************************
Query ID is >Hs_Ptpn1_5pUTR
***************************************************************

---

3' UTR region hits
---

>ref|NM_100161|hsa-miR-302b* MIMAT0000714 *Homo sapiens* miR-302b*
Query: 1730    CTTGTTACACATTATGTTAGAGA    SEQ ID NO: 342
                  **********
Mature miRNA   TCTTTCGTGAAGGTACAATTTCA    SEQ ID NO: 343

---

5' UTR region hits
---

>ref|NM_100161|hsa-miR-302b* MIMAT0000714 *Homo sapiens* miR-302b*
Query: 146     AGGAGGCGCAGCAGCCGCCCTGG    SEQ ID NO: 344
                  *********
Mature miRNA   TCTTTCGTGAAGGTACAATTTCA    SEQ ID NO: 345

---

3' UTR region hits
---

>ref|NM_100088|hsa-let-7i MIMAT0000415 *Homo sapiens* let-7i
Query: 608     TTGTAAGCAGTTGTTATTTAG      SEQ ID NO: 346
                  **********

-continued

```
Mature miRNA  TGTCGTGTTTGATGATGGAGT    SEQ ID NO: 347

>ref|NM_100088|hsa-let-7i MIMAT0000415 Homo sapiens let-7i
Query: 1602    TGAGCTGGGCTTGTTGTTTTT    SEQ ID NO: 348
                     **********
Mature miRNA  TGTCGTGTTTGATGATGGAGT    SEQ ID NO: 349

>ref|NM_100088|hsa-let-7i MIMAT0000415 Homo sapiens let-7i
Query: 705     ACATGATGTGAGATTACTTTG    SEQ ID NO: 350
                     *********
Mature miRNA  TGTCGTGTTTGATGATGGAGT    SEQ ID NO: 351

>ref|NM_100088|hsa-let-7i MIMAT0000415 Homo sapiens let-7i
Query: 732     ATTCTCCTCCCTGTTATCTGC    SEQ ID NO: 352
                     *********
Mature miRNA  TGTCGTGTTTGATGATGGAGT    SEQ ID NO: 353

----------------------------------------------------------------
5' UTR region hits
----------------------------------------------------------------
>ref|NM_100088|hsa-let-7i MIMAT0000415 Homo sapiens let-7i
Query: 127     ACGGCGCAGTGGGCCGAGAAG    SEQ ID NO: 354
                     *********
Mature miRNA  TGTCGTGTTTGATGATGGAGT    SEQ ID NO: 355

----------------------------------------------------------------
3' UTR region hits
----------------------------------------------------------------
>ref|NM_100208|hsa-miR-196b MIMAT0001080 Homo sapiens miR-
196b
Query: 702     AACATGATGTGAGATTACTTT    SEQ ID NO: 356
                     **********
Mature miRNA  GGTTGTTGTCCTTTGATGGAT    SEQ ID NO: 357

----------------------------------------------------------------
5' UTR region hits
----------------------------------------------------------------
>ref|NM_100208|hsa-miR-196b MIMAT0001080 Homo sapiens miR-
196b
Query: 39      GCAGCAGCGGCTAGGGCGGCG    SEQ ID NO: 358
                     *********
Mature miRNA  GGTTGTTGTCCTTTGATGGAT    SEQ ID NO: 359

>ref|NM_100208|hsa-miR-196b MIMAT0001080 Homo sapiens miR-
196b
Query: 54      GCGGCGGTAGCTGCAGGGGTC    SEQ ID NO: 360
                     *********
Mature miRNA  GGTTGTTGTCCTTTGATGGAT    SEQ ID NO: 361

**************************************************************
Query ID is >Hs_Scarb1_5pUTR
**************************************************************
```

Example 9 microRNA Targets Containing Simultaneous 5'-UTR and 3'-UTR Interaction Sites Based on both hybridization energy and sequence matches, many endogenous motifs within human 5'-UTRs specific to the 3'-ends of miRNAs. Rather than suggesting possible miRNA interactions with other regions of mRNA, we report combinatory interactions between a single miRNA and both end regions of an mRNA, based on our finding that many miRNAs contain significant interaction sites with mRNA 5'-UTR and 3'-UTR motifs through their 3'- and 5'-end sequences, respectively. As a model system, we experimentally verified that hsa-miR-34a function depends on both UTR sites of AXIN2. We propose here a new miRNA target class containing simultaneous 5'- and 3'-UTR interaction sites. Since we identify such sites in genes showing large-scale protein changes upon deletion or over-expression of all four miRNAs used in Baek et al.'s study this target class can serve as an efficient screening tool for identifying real targets, especially in the case of non-conserved miRNAs or target sites (Baek, D., J. Villen, C. Shin, F. D. Camargo, S. P. Gygi, and D. P. Bartel. 2008. The impact of microRNAs on protein output. Nature).

Results

Presence of miRNA Interaction Sites in Human 5'UTR We checked for genome-wide miRNA interaction motifs in human 5'-UTR and 3'-UTR. Xie et al. have reported conserved miRNA motifs in the 3'-UTR but not in the 5'-UTR or in coding sequences (Xie, X., J. Lu, E. J. Kulbokas, T. R. Golub, V. Mootha, K. Lindblad-Toh, E. S. Lander, and M. Kellis. 2005. Systematic discovery of regulatory motifs in human promoters and 3' U). We used the same UTR motif dataset sent to us by the authors but defined new conservation classes C=0 (non-conserved but human-enriched), 1 (minimally conserved and human-enriched), and ≥10 (highly conserved). To determine seed and non-seed region effects, all mature miRNAs were downloaded from miRBase (Release 11.0) (Griffiths-Jones, S., H. K. Saini, S. van Dongen, and A. J. Enright. 2008. miRBase: tools for microRNA genomics. Nucleic Acids Res 36: D154-158.) and split into their respective 5'- and 3'-ends, making miRNA halves. Following thermodynamic searches for half miRNA-UTR motif interaction using RNAhybrid (Kruger and Rehmsmeier 2006), we treated only consecutively-matched sequences as signals. To calculate significance, total numbers of pairwise interactions between half-miRNAs and UTR motifs were compared with the numbers of interactions with shuffled UTR motifs generated 1,000 times.

Figure 6:
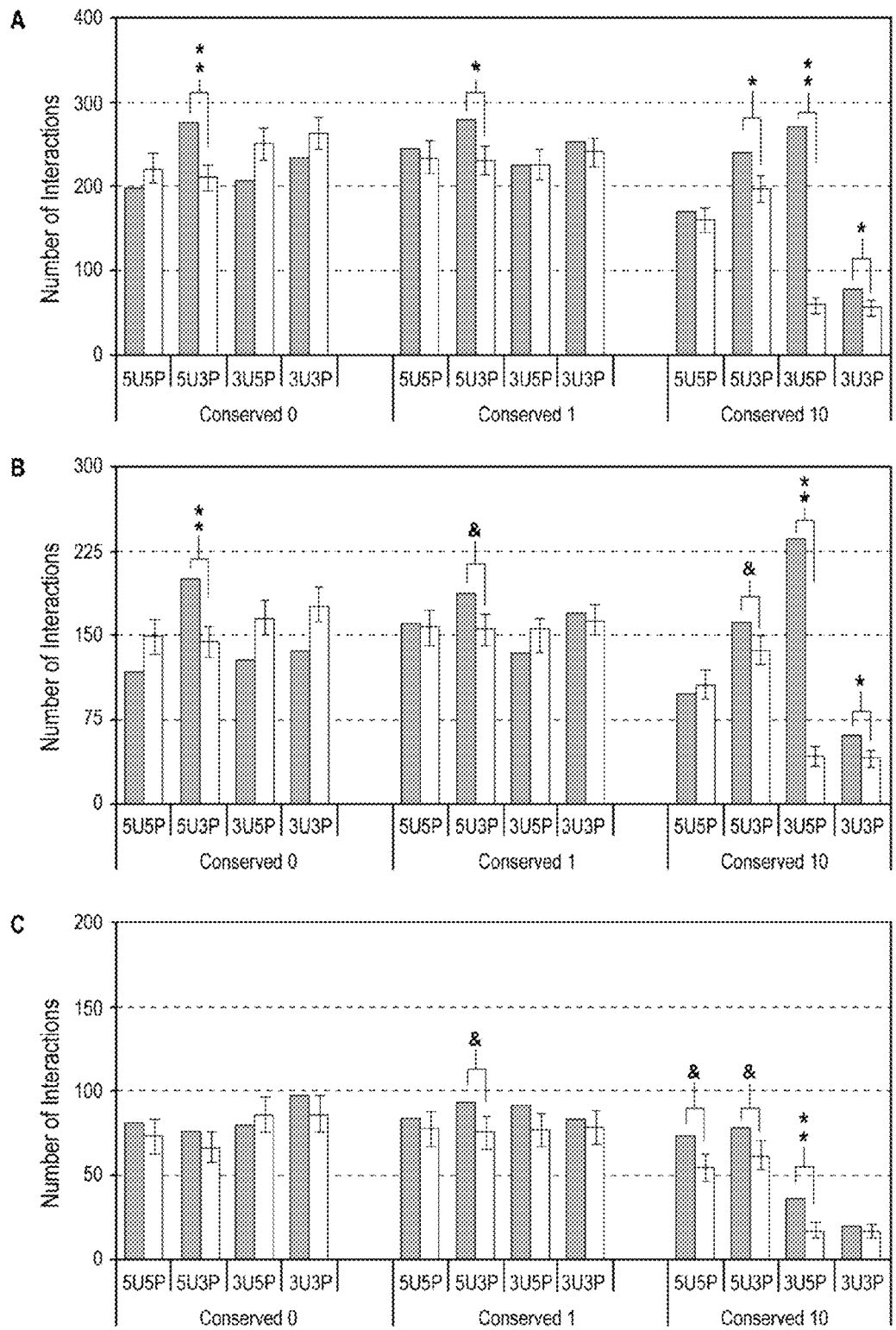
FIG. 6 shows the analysis of predicted interactions between 8-mers from different conservation classes and miRNAs. Closed bars indicate number of predicted interactions between 5'-UTR or 3'-UTR 8-mer sequences (indicated by 5U or 3U respectively) and 5'- or 3'-ends (indicated by 5P or 3P respectively) of a full set of mature miRNAs (A), of conserved miRNAs (B), and of non-conserved miRNAs (C). Open bars correspond to mean number of interactions after 1000 shuffling iterations and error bars indicate standard deviations. Double asterisk indicates p<5e-05, single asterisk p<5e-03. and ampersand p<0.05.

In these analyses, we identified 5'-UTR motifs (5U) which interact significantly with the miRNA 3'-end (3P) in all conservation categories (5U3P's in FIG. 6A), most significantly in the case of C=0.3'-UTR motifs (3U), on the other hand, show significant interactions with miRNA only in the case of highly conserved 8-mers (C≥10) consistent with previous reports (Conserved 10: 3U5P and 3U3P in FIG. 6A). Besides the most significant and well-known interaction of 3U5P, our identification of 3U3P interaction is in accordance with previous findings that the 3'-end of a miRNA may either complement a seed match or compensate for an imperfect one. Our new finding of 5U3P interaction was also observed with human-enriched 5'-UTR motifs when we followed Xie et al.'s conservation score (FIG. 6).

Viewed in terms of conserved and non-conserved miRNAs, interactions with conserved miRNAs show a trend similar to the one above, differing only in the levels of significance (FIG. 6B). Interestingly, 5U3P interactions with non-conserved miRNAs lack significance for C=0 motifs (FIG. 6C), the 5U3P signal in C=0 in FIG. 1A coming from that of conserved miRNAs. We also observed significant interactions between highly conserved 5'-UTR motifs and the 5'-end (5U5P) of non-conserved miRNAs (FIG. 6C).

In conjunction with the significant interaction between the seed region of a miRNA and the 3'-UTR, the preferential 5'-UTR interaction with the 3'-end of miRNA raises the question whether a common miRNA may target both UTRs of an mRNA by interacting with different ends of the miRNA. Based on the significance data in FIG. 6A, 37 common miRNAs identified between 5U3P (C=0 and 1: total 250 miRNAs) and 3U5P (C=10: total 116 miRNAs) cases are listed in Table 5. When these kinds of motifs exist in a single gene, will they be regulated by a single miRNA?

sites, using only minimal interaction sequences of 36-mer in the experimental constructs. As shown in FIG. 7A, the hsa-miR-34a effects on this 36-mer should mostly come from the 3'-end. Note that the full 3'-UTR inserted in the construct is 1,408 nucleotides long.

Reporter gene assay of MCF-7 cells revealed that miR-34a down-regulated luciferase expression in constructs containing either the 5'-UTR (5ULuc) or 3'-UTR (Luc3U) alone. When both Axin2 UTR sites were present (5ULuc3U), luciferase expression was further repressed by miR-34a (FIG. 7C). In order to identify endogenous miRNA effects in addition to those exogenously induced, we blocked endogenous miR-34a using inhibitor antisense RNA oligo. 5ULuc3U expression was greater than that of 5ULuc or Luc3U, suggesting that the 5'-UTR of AXIN2 together with the 3'-UTR are functional target sites for miR-34a in the cells (FIG. 7D). In addition, the fold change of 5ULuc3U1.88 is greater than with the addition of 5ULuc and Luc3U1.61. Considering the many interaction sites in the 3'-UTR, the synergetic 5'-UTR effect on endogenous miRNA function is remarkable. These data suggest that in conjunction with the 3'-UTR, the 5'-UTR of AXIN2 plays a role in miRNA-mediated repression in human cells beyond fine-tuning In order to confirm the sequence specificity of 5'-UTR effects, we created two constructs with sites mutated (5Umut1Luc3U and 5Umut2Luc3U). Separate luciferase experiments inducing hsa-miR-34a showed reduction of repression when the 5U interaction sites are mutated (FIG. 7E).

hsa-miR-34a Interacts with WNT1 in 5'-UTR Sequence-Specific Way

We were interested in other genes presenting similar sequence specificity of 5'-UTR interaction sites. An interesting interaction occurs between the 5'-UTR of WNT1 and the 3'-end of hsa-miR-34a, there being 7-mer consecutive matches without any GU wobbles and a target A-nucleotide corresponding to the end miRNA (FIG. 8A), mirroring TargetScan's t1A interaction in the 3'-UTR (Lewis, B. P., C. B. Burge, and D. P. Bartel. 2005. Conserved seed pairing, often flanked by adenosines, indicates that thousands of human

TABLE 5

Genes with 5'-UTR interaction sites (as well as conventional 3'-UTR sites) for miRNAs used in Baek et al.'s study (Baek et al. 2008).

| miRNA | Gene Symbol | Accession Number | Log2 Fold change[1] Protein | Log2 Fold change[1] mRNA | 3U target site number[1,2] | Rank[1,3] |
|---|---|---|---|---|---|---|
| hsa-miR-1[4] | CNN3 | NM_001839 | −0.923 | −0.550 | 1 | 7 |
| hsa-miR-124[4] | STOM | NM_004099 | −2.392 | −1.269 | 1 | 4 |
|  | CDCA7L | NM_018719 | −2.121 | NA | 1 | 7 |
| hsa-miR-181a[4] | GNB4 | NM_021629 | −1.537 | −0.275 | 5 | 1 |
|  | COL5A1 | NM_000093 | −0.841 | −0.318 | 1 | 8 |
|  | SLC2A1 | NM_006516 | −0.836 | 0.218 | 1 | 10 |
|  | CDYL | NM_170751 | −0.828 | −0.339 | 1 | 11 |
| mmu-miR-223[5] | Ctsl | NM_009984 | 2.402 | 1.181 | 1 | 1 | hsa-miR-34a Targets AXIN2 Through Both UTRs

A highly-conserved human miRNA, hsa-miR-34a, has such interaction sites in the human gene AXIN2 (FIG. 7A). Though miR-34a is not in Table 5, the 5'-end was predicted to interact with three highly-conserved (and one non-conserved) AXIN 3'-UTR sites, and the 3'-end with two overlapping 5'-UTR sites (FIG. 7A) present only in human and mouse but enriched in human 5'-UTRs. We used hsa-miR-34a and AXIN2 as a model system to verify simultaneous UTR interactions. Since interactions between miRNA and 3'-UTR are well-established, we focused on the 5'-UTR interaction genes are microRNA targets. Cell 120: 15-20). In order to establish 5'-UTR interaction site specificity, we again used only 39-mer sequences containing this interaction site but at a different interaction position from the AXIN2 case, while using entire 3'-UTR sequences. Here we changed only three sequences to disrupt the 7-mer canonical Watson-Crick base pairing (FIG. 8A).

Reporter gene assay of MCF-7 cells showed that miR-34a down-regulated constructs containing both WNT1 UTR sites (5ULuc3U) to a greater extent than those constructs containing 3'-UTR (Luc3U) alone (FIG. 8C). This additional repression was relieved when the 5U interaction sites were mutated (FIG. 8C), demonstrating that miRNA interaction occurs in a sequence-specific manner. We observed similar miR-34a functional dependency on the 5'-UTR sequences in the other gene (unpublished data).

lin-4-Like Artificial miRNA Interacts with Lin-28-Like 5'-UTR Sites in a Sequence-Specific Way To establish that our finding of sequence-specific 5'-UTR interaction in addition to 3'-UTR interaction was not limited to a single miRNA or cell line, we chose the C. elegans lin-4 and lin-28 pair for human cell line validation experiments. The 3'-UTR of lin-28 contains a single canonical target site conserved in the lin-28 homologs of human, mouse and chimpanzee whereas the single 5'-UTR site predicted to bind with the 3'-end of the miRNA is lacking in all of the homologs. Considering the lower physiological temperature of C. elegans and lack of homologs in human, we prepared artificial 5U3P (5'-UTR and the 3'-end miRNA) pairing sequences containing 8-mer consecutive matches without GU wobbles, while keeping 3U5P interaction the same as in the lin-4 and lin-28 case (5ULuc3U in FIG. 9A). The construct having the 5'-UTR sequences of lin-28 was used as the 5'-UTR mutant site (5UmutLuc3U) corresponding to lin-4-like artificial miRNA (lin-4-like) to verify 5'-UTR interaction-site specificity. Note that the length of the inserted sequences and interaction site position are different from the miR-34a experiments to establish the sequence specificity.

Figure 9:
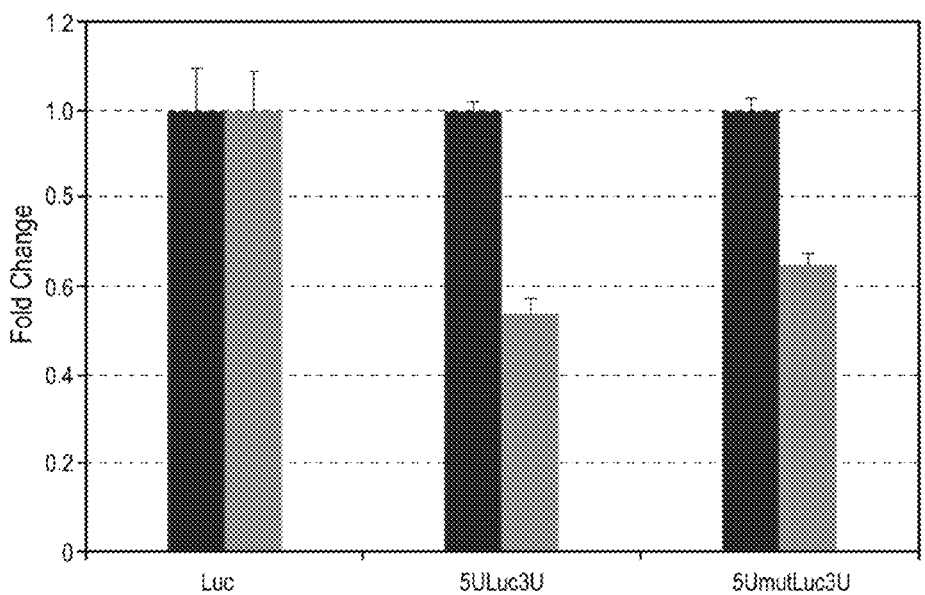
FIG. 9 shows the effect of 5'-UTR interaction site with lin-4-like on reporter expression levels. (A) Predicted interactions between lin-4-like and lin-28-like UTR sequences. The functional strand of the lin-4-like contains an intact cel-lin-4 seed region (bold) while the 3'-end is modified. There is an extended seed match between the 5'-end of lin-4-like and the wild-type lin-28 3'-UTR binding site. The 3'-end of lin-4-like is complementary to the artificial lin-28-like 5'-UTR binding site created by introducing a few GC base-pairs (bold italics) to form a perfect match. The wild-type lin-28 5'-UTR presents an imperfect match. Structure and energy calculations were carried out using RNAhybrid. The sequences are SEQ ID NO: 454, SEQ ID NO: 455, SEQ ID NO: 456, SEQ ID NO: 457, SEQ ID NO: 458, ID NO: 459, ID NO: 460, and SEQ ID NO: 461 from top to bottom. (B) Schematic showing vector constructs containing firefly luciferase reporter gene used in transfection experiments. lin-28-like 5'-UTR segment containing 8-mer perfectly matched and mutated sites is indicated as 5ULuc3U and 5UmutLuc3U, respectively. (C) Fold changes of Renilla-normalized firefly luciferase expression levels upon co-transfection with lin-4-like (no shading) with respect to non-specific hsa-miR-16 (dark shading). Error bars represent standard deviation recorded from 8 pooled replicates.

Reporter gene assay of HEK293 cells showed that luciferase expression reduction due to lin-4-like was diminished when the 5'-UTR interaction site was mutated (Wilcoxon rank-sum test p<0.005 for 5ULuc3U and 5UmutLuc3U in FIG. 9C). It is clear that mismatches in the 5'-UTR corresponding to the 3'-end of lin-4-like disrupt interaction.

Translationally Repressed Genes Contain Both UTR Sites

To what extent is this finding generalizable in endogenous miRNAs? A recent study measured thousands of protein levels in response to miRNA changes (Baek et al. 2008). One of the experiments involved removing endogenous Mirn223, while the rest induced additional miRNAs, finding hundreds of proteins negatively correlated to each of the four miRNAs used, many of the proteins having conventional 3'-UTR sites. We wondered if 5'-UTR interaction sites exist for the 3'-end of miRNAs in genes showing large protein fold-changes and having the 3'-UTR sites identified in Baek et al.'s study (Baek et al. 2008). For each miRNA, we checked the 10 genes whose protein levels were most changed and found both UTR sites present in at least one case for all miRNAs. These miRNAs and targets are in Table 5, including CDYL, which ranks 11th among hsa-miR-181a targets in terms of fold change. Not only do all targets in Table 5 have highly significant fold changes; all protein fold changes greatly exceed mRNA fold changes, showing significant translation repression. Note that mmu-miR-223 targeting both UTRs of Ctsl and hsa-miR-181a targeting GNB4 are cases of maximal protein fold change, while GNB4 mRNA change is only modest. We thus propose a new miRNA target class containing simultaneous interactions of 5U3P and 3U5P.

miBridge Targets

This new miRNA target class can greatly diminishes the number of predicted targets. While the number of conserved miRNA targets predicted for conserved 3'-UTR sites can reasonably be checked, there has been no practical way to study non-conserved miRNA targets due to the thousands of target predictions. Encouraged by the large protein-fold change genes containing potential interaction sites in both their UTRs, we provide here potential targets containing both UTR sites, such as simultaneous interactions between 5'-UTR and the 3'-end together with 3'-UTR and the 5'-end of a miRNA (miBridge). While 3'-UTR interaction sites have been extensively studied, rules for 5'-UTR interaction need to be newly established. As a first attempt, we basically follow current 3'-UTR interaction rules except for the position restriction. Following initial interaction searches between halves of miRNAs and corresponding UTRs using RNAhybrid, we considered sequence matches. We set a −13 kcal/mol energy cut-off in the RNAhybrid parameter when there are consecutive sequence matches without GU wobbles, the same condition for 3'-UTR interaction (based on the interaction energy between the 5'-end of miR-1 and 3'-UTRs). We additionally constrained 3'-UTR interaction to match position 2-7 from the 5'-end. Note that the calculation includes no conservation information. Predictions of miRNAs targeting genes with both 5'-UTR and 3'-UTR sites are available at http://sitemaker.umich.edu/miBridge (Supplementary Data Set).

The highly reduced target search space of miBridge now allows us to identify a human-specific miRNA target. SEC24D is one of our genes of interest due to its transport function. TargetScan (Lewis et al. 2005) predicts 102 miRNA families as regulating SEC24D (a combination of conserved and non-conserved family info files downloaded from http://www.targetscan.org/cgi-bin/targetscan/data_download.cgi?db=vert 42), while miBridge predicts 2 miRNA, miR-524-5p and miR-605, common to TargetScan. Since TargetScan treats miR-520d-5p and miR-524-5p as one family having the same targets, we investigate miR-605 for ease of comparison. The numbers of predicted targets of miR-605, a miRNA currently identified only in primate, are 4,952 by TargetScan (from their non-conserved family info file). Based on TargetScan's prediction, miR-605 is highly unlikely to turn up as regulating SEC24D. However, we could easily select miR-605 and SEC24D as a miRNA functional pair based on miBridge target prediction. RNAhybrid calculated the interaction energy between the 3'-end of miR-605 and the 5'-UTR of SEC24D as −16.1 kcal/mol. The 5'-end of miR-605 interacts with the 3'-UTR at −16.7 kcal/mol with 9-mer matches without GU (FIG. 10A). Endogenous SEC24D levels in HeLa cells were measured using miR-605 induction or by blocking endogenous miR-605 in comparison with control miRNAs. Induction of miR-605 reduced SEC24D mRNA and protein levels, while anti-miR-605 increased SEC2D mRNA and protein levels, confirming miR-605's effect on endogenous SEC24D (FIG. 10). Therefore, initial candidate miR-605 turns out to be a true regulating miRNA.

Discussion

Translation repression has been reported to occur when a 3'-UTR target site for endogenous let-7a in HeLa cells is moved to the 5'-UTR (Lytle, J. R., T. A. Yario, and J. A. Steitz. 2007. Target mRNAs are repressed as efficiently by microRNA-binding sites in the 5' UTR as in the 3' UTR. Proc Natl Acad Sci USA 104: 9667-9672.). We now show there exist many endogenous target sites in 5'-UTR for endogenous miRNAs, so that these 5'-UTR sites can contribute to miRNA function. The data in FIG. 6A is intriguing in that 1) significant miRNA interactions in the 5'-UTR occur only with the 3'-end of miRNA (5U3P), and 2) such 5U3P significance seems to arise in highly-conserved 8-mers and spread into less-conserved but highly-human-present motifs (C=0 and 1). Non-conserved sites have been explored under the assumption that each species or genome might employ them to attribute specificity in some manner (Farh et al. 2005). Considering that the 3'-end of miRNA family members (intraspecies) and those of some miRNAs across species differ, the 3'-end of miRNAs may contribute to gene- or species-specific target site recognition of the 5'-UTR. Dividing miRNAs into conserved and non-conserved ones, it seems that human-specific 5U motifs interact with pre-existing miRNAs (FIG. 6B) and that human-specific miRNAs interact with pre-existing 5U motifs (FIG. 6C). The significant 5U5P presence in the highly conserved UTR motifs and non-conserved miRNAs (FIG. 6C) may reflect an emergent feature of human-specific miRNAs, wherein miRNA and 5'-UTR are actively evolving in response to each other.

We used 36-mer sequences for the AXIN2 5'-UTR construct, which interacts mostly with the 3'-end of miR-34a. In contrast to 3'-UTR sites, which are well-dispersed across 1,408 nucleotides, making additive miRNA effects possible, the two 5'-UTR sites overlap, leaving no opportunity for additive effects. We expect to see four times higher 3'-UTR effects than with 5'-UTR, assuming the 5'-end represses translation in the 3'-UTR just as the 3'-end does in the 5'-UTR. Therefore, the contribution of AXIN2 5'-UTR sites in protein repression by hsa-miR-34a induction is no less than that of each site in the 3'-UTR (FIG. 7C). Of some interest are the endogenous miRNA effects on both UTRs in this pair (FIG. 7D). Not only is the inserted 5'-UTR site effect similar to that of the whole 3'-UTR (about 40 times longer than the inserted 5'-UTR sequences), but the presence of both UTRs has a synergetic effect on miRNA function. Exogenous hsa-miR-34a effects on top of endogenous hsa-miR-34a function may lead to saturation of repression capacity with 5ULuc3U in FIG. 7C, while repression of Luc3U is more easily achieved with exogenous miR-34a. Previous studies with exogenous miRNAs may have found significant effects where exogenous miRNAs compete minimally with endogenous miRNAs.

The endogenous miRNA effect on targets with both 5'-UTR and 3'-UTR is highlighted in Table 5. The largest fold change protein Ctsl due to mmu-miR-223 deletion is identified as having both UTR sites for mmu-miR-223. Most salient in Table 5 is the low translational efficiency when both UTR interaction sites are present. In order to fully understand miRNA function, therefore, we advise the insertion of both 5' and 3'-UTR sequences in miRNA functional experiments, which has rarely been done before. Previous miRNA functional experiments using 3'-UTR alone usually achieved about 40-60% protein reduction (Lim, L. P., N. C. Lau, P. Garrett-Engele, A. Grimson, J. M. Schelter, J. Castle, D. P. Bartel, P. S. Linsley, and J. M. Johnson. 2005. Microarray analysis shows that some microRNAs downregulate large numbers of target mRNAs. Nature 433: 769-773). We may see more protein reduction with 5'-UTR inclusion where interaction sites exist, as seen in FIGS. 7 and 8.

Considering the large number of potential targets with conventional 3'-UTR sites, prioritizing searches using miBridge targets can expedite real target identification, as shown in the case of miR-605 and SEC24D, where miBridge yielded 2 miRNAs rather than TargetScan's 102. We believe miBridge targets thus provide an avenue for exploring non-conserved miRNAs. Moreover, this new class of miRNAs and targets may fall into the class of translation blockers prior to the 40S ribosome reaching the translation start region, preventing 60S association (Wang, B., A. Yanez, and C. D. Novina. 2008. MicroRNA-repressed mRNAs contain 40S but not 60S components. Proc Natl Acad Sci USA 105: 5343-5348), one possible miRNA mechanism of translation repression. These 5'-UTR-interacting miRNAs associated with proteins will provide large steric hindrance against ribosome scanning A recent study reported that miRNA function was abolished when the interaction site context was changed from within the 3'-UTR to within the extended coding region through stop codon change, while siRNA function was retained (Gu, S., L. Jin, F. Zhang, P. Sarnow, and M. A. Kay. 2009. Biological basis for restriction of microRNA targets to the 3' untranslated region in mammalian mRNAs. Nat Struct Mol Biol 16: 144-150). Middle-bulged miRNA interaction may require 80S ribosome-free 3'-UTR for interaction, while the 3'-end of miRNA interaction may be strong and/or bulky enough to compete with a smaller subunit 40S ribosome. It is also possible that the 3'-ends of miRNAs interact with 5'-UTR-associated proteins other than Argonaute proteins.

In this report, all interaction was calculated with miRNA halves. On the other hand, Smalheiser and Torvik previously provided computational evidence for the existence of long interactions (>10 nt) that do not arise preferentially from the 5'-end of miRNAs and are not biased towards the 3'-UTRs of putative targets (Smalheiser and Torvik 2004). Longer seed interaction deserves to be revisited. Finally, in order to establish interaction site specificity, we did not use full length 5'-UTR. Studies with full 5'-UTR sequences may reveal further miRNA functions within this new target class.

Methods

Pre-Processing of microRNA Data.

Mature human miRNA sequences were downloaded from miRBase, version 11.0. These were separated into two categories, conserved and non-conserved. We define a conserved miRNA as one that has a similarly-named counterpart in at least one other species regardless of the percentage identity. For example, miR-34a exists in humans as well as mouse and many others whereas miR-1178, a non-conserved miRNA by our definition, exists only in humans. Following this, miR-NAs were split into their respective 5' and 3'-end halves.

Bioinformatic Analysis.

Xie et al kindly provided us with data on conservation of all possible 8-mer sequences from aligned 5'-UTRs and 3'-UTRs among human, mouse, rat and dog. Each 8-mer was listed along with the number of occurrences conserved in all four species (C), the number of occurrences in the human sequence (N), and the conservation rate (R) given by the ratio C/N, where $0 \leq R \leq 1$. We created five motif conservation categories: 1) C=0, non-conserved 8-mers ordered on decreasing N, 2) C=1, 8-mers with exactly one conserved occurrence, ordered on decreasing N, 3) C≥10, 8-mers with at least 10 conserved occurrences ordered on decreasing C and decreasing R, 4) positive MCS, and 5) negative MCS described below. Briefly, the motif conservation score (MCS, from Xie et al.) is reported as a Z-score calculated using binomial probability, $MCS=(C-Np0)/[Np0(1-p0)]1/2$, where C is the number of conserved instances, N the number of occurrences in human and p0 the estimated rate of conservation. We calculated p0 as the average conservation rate of all 65,536 8-mers. The top 540 highest scoring 5'-UTR and 3'-UTR 8-mers from each category above were then used for further analysis. RNAhybrid (Kruger, J. and M. Rehmsmeier. 2006. RNAhybrid: microRNA target prediction easy, fast and flexible. Nucleic Acids Res 34: W451-454) was used to search for potential interactions between the UTR motifs and each miRNA. Doench and Sharp having demonstrated the correlation between binding energy and fold repression (Doench, J. G. and P. A. Sharp. 2004. Specificity of microRNA target selection in translational repression. Genes Dev 18: 504-511), we set an energy threshold of −14 kcal/mol based on the RNAhybrid binding energy prediction for the CXCR4 siRNA seed region and the corresponding target site used in Doench and Sharp's paper. The results were then filtered for consecutive 8-mer matches with GU wobbles between the 8-mers and miRNA ends.

Statistical Analysis.

Shuffled 8-mers derived from the corresponding conservation category were used as controls to assess the significance of the number of interactions between motifs and miRNAs. The control datasets were generated 1000 times and the number of interactions calculated as an average over these iterations. We assumed the distribution of number of interactions to be normal and calculated p-value using the Z-test.

Reporter Gene Constructs and Assay for miR-34a Experiments.

The luciferase coding sequences were PCR-amplified and inserted between HindIII and BamHI sites of pcDNA3.1-Hyg (+), a mammalian expression vector (Invitrogen) to generate luciferase expression constructs. To make 3'-UTR constructs, the 3'-UTR of AXIN2 (NM_004655; +1~+1059) and WNT1 (NM_005430; +1~+1056) were amplified from genomic DNA of MCF-7 cells and cloned into the BamHI and NotI sites. The synthetic oligonucleotide containing 5'-UTR sequences targeted by miR-34a of AXIN2 (SEQ ID NO: 362) (5'-GCC CGG GGG AGT CGG CTG GAG CCG GCT GCG CTT TGA, corresponding to +44~+79 among 314 nt of the 5'-UTR) and that of WNT1 (SEQ ID NO: 363) (5'-CGG GCA ACA ACC AAA GTC GCC GCA ACT GCA GCA CAG AGC-3', positions +141~+179 among 209 nt of the 5'-UTR) were inserted into NheI and HindIII sites upstream of luciferase vectors. The two AXIN2 5'-UTR mutants are (SEQ ID NO: 364) (5'-GCC CGG GGG ACT AGA GTG GGU CGG GCT GCG CTT TGA-3') and (SEQ ID NO: 365) (5'-GCC CGG GGG AGG GAT AGT GGU CGG GCT GCG CTT TGA-3') and WNT1 5'-UTR mutant is (SEQ ID NO: 367) (5'-CGG GCA ACT AGG AAA GTC GCC GCA ACT GCA GCA CAG AGC-3'). For the miR-34a induction experiments, each reporter construct (5 ng) was co-transfected with 20 μmol of negative control RNA oligo (Ambion, AM17110) or miR-34a precursor RNA oligo (Ambion, product ID PM11030) using Lipofectamine 2000 (Invitrogen) for 48 hrs. In experiments inhibiting endogenous hsa-miR-34a, 5 ng of each construct was co-transfected with 40 μmol of anti-miR-34a inhibitor (Ambion, product ID AM11030) or anti-miR negative control (Ambion, product ID AM17010). Fold change by miR-34a or miR-34a inhibitor was measured by a dual-luciferase assay kit (Promega), and the firefly luciferase activity normalized relative to a simultaneously transfected 1 ng of SV40-driven Renilla luciferase expression plasmid. Experiments were performed in two sets of triplicates simultaneously, one for reporter gene assay and one for qPCR analysis.

Reporter Gene Constructs for Lin-28-Like.

The synthetic oligonucleotides for lin-28-like UTR sequences were purchased from Integrated DNA Technologies, Inc. The sequences used in reporter gene constructs to mimic 5'-UTR and 3'-UTR sequences were (SEQ ID NO: 367) (5'-GTG GTA TTG TTG TTC TGT AAG CCA CAT AGG TTG TAT TCT CTA GTT AAC ACA TAG T-3') and (SEQ ID NO: 368) (5'-CAC CTA CCT CCT CAA ATT GCA CTC TCA GGG ATT CTT TTT TTT TCA AAA TAG AAC T-3'), respectively. The corresponding mutated 5'-UTR sequences were (SEQ ID NO: 369) (5'-GTG GTA TTG TTG TTC TGT ATA TTT GAT AGG TTG TAT TCT CTA GTT AAC ACA TAG T-3'), which contains the 5'-UTR sequences of lin-28. The expression reporter vector, pMIR-REPORT™, was purchased from Ambion, Inc. (Cat. # AM5795). 5'-UTR sequences were cloned into the BamHI restriction site upstream of the luciferase coding sequence and the 3'-UTR sequences were cloned into the multiple cloning site using HindIII and SpeI. UTR sequences and their orientation in the constructs were confirmed by DNA sequencing (University of Michigan DNA sequencing core).

Lin-4-Like Sequences.

Strands that make up the lin-4-like duplex were purchased from Integrated DNA Technologies, Inc. The in-house designed sequences of the functional strand and opposing strand of lin-4-like were (SEQ ID NO: 370) (5'-UCC CUG AGA CCU GUG GCU UGA-3') and (SEQ ID NO: 371) (5'-AAG CCA CAG GUC UCA GAA GUU-3'), respectively. The single stranded molecules were later annealed using the manufacturer's protocol.

Cell Culture and Transfection for Lin-28-Like Assay.

HEK293 cells were grown to 80% confluence in Dulbecco Modified Eagle Medium (DMEM) with 10% Fetal Bovine Serum. Cells were then trypsinized and plated in 12-well plates with about 250,000-300,000 cells per well. 500 ng of each firefly reporter construct and 50 ng of internal control Renilla reporter pRL-tk (Promega, Cat. # E2241) were co-transfected with either 37 μmol of control miRNA (hsa-miR-16; Ambion, Inc., product ID PM10339) or 170 μmol of lin-4-like using Lipofectamine 2000 (Invitrogen). Owing to mismatches in the duplex we used, we increased the siRNA concentration to compensate for any inefficiency in annealing. Transfections were performed in quadruplicate two independent times. Cells were lysed 24 hours post-transfection and assayed for luciferase expression using the Dual-Luciferase Reporter Assay System (Promega, Cat. # E1910) and GloMax® 96 Microplate Luminometer w/Dual injectors (Promega, Cat. # E6521) according to the manufacturer's protocol. Here, experiments were repeated two independent times in quadruplicate each time. Renilla-normalized luciferase values were normalized using values from a non-specific miR-16 transfection. To determine if there was significant difference between 5ULuc3U and 5UmutLuc3U, we used the Wilcoxon rank-sum test to calculate p-values from the normalized luciferase values for each pair of constructs chosen.

5U3P Site Analysis Using Baek et al's Proteomics Data

After downloading Supplementary Tables 2, 3, 4, 5 of Baek et al.'s study, we totalled all 3'-UTR interaction sites for each transcript. We chose transcripts having at least one 3U target site, sorted them based on their degree of protein fold change, and selected the 10 transcripts with the most protein fold change. The accession numbers of the 10 transcripts related to each miRNA are as follows: hsa-miR-1: NM_019594, NM_001043352, NM_003769, NM_017444, NM_001111, NM_001083112, NM_001839, NM_012120, NM_172173, NM_001655; hsa-miR-124: NM_001084, NM_006289, NM_206855, NM_004099, NM_133452, NM_015493, NM_018719, NM_021961, NM_138473, NM_001753; hsa-miR-181a: NM_021629, NM_001037165, NM_006931, NM_002024, NM_014988, NM_004282, NM_015057, NM_000093, NM_002129, NM_006516, NM_170751; mmu-miR-223: NM_009984, NM_022880, NM_030253, NM_029564, NM_029364, NM_008633, NM_145452, G270135013, NM_001033606, NM_011486. We searched the 5'-UTR of each transcript for interaction with the 3'-end of its corresponding miRNA using RNAhybrid and then consecutive sequence matches. Here we set the RNAhybrid energy cutoff at −13 kcal/mol and consecutive sequence matches at 7-mer or greater, in accordance with the characteristics of 3'-UTR interaction sites.

miBridge Targets

All mature miRNAs were downloaded from miRBase (Release 11.0) (Griffiths-Jones, S., H. K. Saini, S. van Dongen, and A. J. Enright. 2008. miRBase: tools for microRNA genomics. Nucleic Acids Res 36: D154-158) and split into their respective 5'- and 3'-ends, making miRNA halves. All mRNA coordinate data and genome sequences of all human chromosomes were downloaded from the UCSC genome browser (Karolchik, D., R. M. Kuhn, R. Baertsch, G. P. Barber, H. Clawson, M. Diekhans, B. Giardine, R. A. Harte, A. S. Hinrichs, F. Hsu, K. M. Kober, W. Miller, J. S. Pedersen, A. Pohl, B. J. Raney, B. Rhead, K. R. Rosenbloom, K. E. Smith, M. Stanke, A. Thakkapallayil, H. Trumbower, T. Wang, A. S. Zweig, D. Haussler, and W. J. Kent. 2008. The UCSC Genome Browser Database: 2008 update. Nucleic Acids Res 36: D773-779). An in-house program extracted 5'-UTR and 3'-UTR sequences from chromosome sequences using RefSeq coordinate data (thus only RefSeq data are included in the database). We first searched the 5'-end of each miRNA for entire 3'-UTRs using RNAhybrid parameters of $-e -13 -f 2,7$ and the 3'-end of miRNA for entire 5'-UTRs using parameter of $-e -13$. RNAhybrid outputs were filtered for consecutive 7-mer without GU matches. Only those miRNAs and targets commonly identified in both searches were retained as miBridge targets.

Hsa-miR-605 Transfection for SEC24D Assay

For transient transfection, HeLa cells were seeded at 60% confluency, and transfections carried out using Pre-miR miRNA Precursor Starter Kit (Ambion, AM1540). HeLa cells were transfected with negative control-1 Precursor, Pre-mir-605, or anti-mir-605 miRNAs in 12-well plates using siPORT™ NeoFX™ according to the manufacturer's protocol.

Western Blot Analysis

Cells were harvested three days post-transfection for western-blot analysis. Protein samples were extracted from cells using PRO-PREP™ protein extraction solution (Intron Biotechnology, 17081), and protein concentration was measured by BCA protein assay kit (Pierce, 23227). 40 µg of proteins were separated by SDS-PAGE and then transferred to nitrocellulose membranes (MILLIPORE, HAHY00010). The membranes were blocked for 1 h in blocking buffer (1×-Tris-bufered saline, 5% nonfat dry milk, and 0.1% Tween 20), which was replaced by anti-SEC24D monoclonal antibody (Abnova, H00009871-M04) in blocking buffer, overnight at 4° C. Primary antibody was detected using horseradish peroxidase-linked goat antimouse antibody (Amersham Biosciences, NA931V) and visualized with the SUPEX ECL reaction kit (Neurotics, MNPS-200401). The blots were re-blotted with HRP-conjugated-☐-actin (ACTB) antibodies (Santa Cruz, sc-47778) without stripping. The bands were scanned with hp scanjet 3570c (Hewlett-Packard) and quantified using NIH image software.

Quantitation of SEC24D mRNA with Real-Time PCR

Cells were harvested two days post-transfection, and the total RNA was extracted with the mirVana miRNA isolation kit (Ambion, AM1560) according to the manufacturer's instructions. To validate SEC24D mRNA expression, qRT-PCRs were performed using Taqman Gene Expression Master Mix (Ambion, 4369016) and Taqman probe assays for SEC24D (Assays-on-Demand, Hs00207926_m; Applied Biosystems) and GAPDH (Assays-on-Demand, Hs99999905_m; Applied Biosystems) following the manufacturer's instructions. All the primers and probes are cDNA-specific. We quantified transcripts of GAPDH as the endogenous RNA control, normalizing each sample on the basis of its GAPDH content. Each sample was tested in triplicate for each gene. Real-time PCR was carried out according to the manufacturer's instructions (Applied Biosystems 7500).

Example 10

Unified Translation Repression Mechanism for MicroRNAs and Upstream AUGs

Using sequence data from whole-genome cDNA alignments we identified 1418 uAUG sequences on the 5'-UTR that specifically interact with 3'-ends of conserved miRNAs. We observed these in addition to a significant number of seed-matches with uAUG sequences. We computationally identified miRNAs predicted to target six genes through their uAUGs, which were previously found to suppress translation. We extended this meta-analysis by confirming expression of these miRNAs in the cell-lines used in the studies. Similarly, seven members of the KLF family of genes containing uAUG were computationally identified to interact with several miRNAs. Using KLF9 as an example we show that miRNAs expressed only in HeLa cells and not N2A cells can bind the uAUGs responsible for inhibition of protein translation. Our results showed that tissue- or cell-line specific repression of protein translation by uAUGs can be explained by the presence or absence of miRNAs that target these uAUG sequences. We propose a model whereby miRNAs binding the uAUGs hinders the progression of ribosome scanning the mRNA before it reaches the open reading frame (ORF).

While both miRNAs and uAUGs are known to down-regulate protein expression, we show that they may be functionally related by identifying potential interactions through a sequence-specific binding mechanism. Using prior experimental evidence that shows uAUG effects on translation repression together with miRNA expression data specific to cell lines, we show that cell-specific down-regulation of protein expression, while maintaining mRNA levels, may be due to the simultaneous presence of miRNA and target uAUG sequences in one cell type and not others. These findings can shed light on tissue-specific translation repression by miRNAs through uAUGs.

Results uAUGs are Potential miRNA Target Sites

Figure 11:
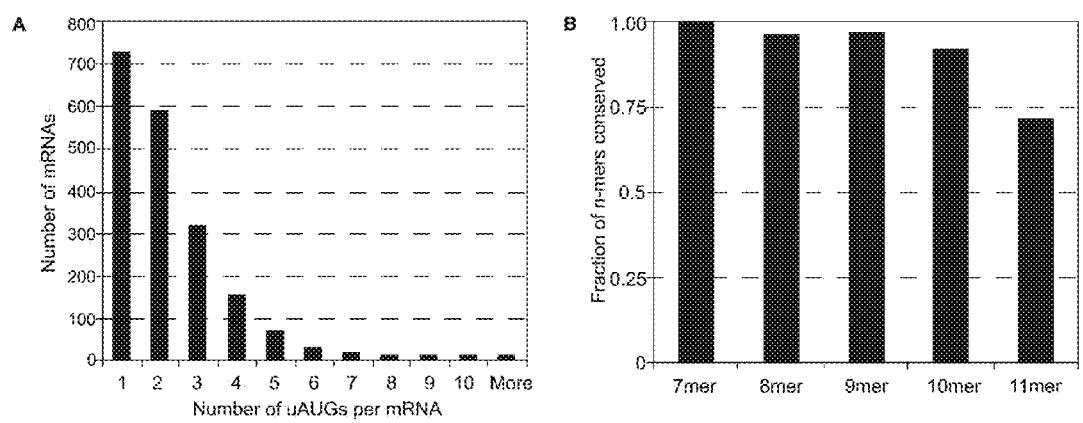
FIG. 11 provides a number of uAUGs in 5'-UTRs and their conservation. (A) Distribution of uAUGs in human 5'-UTR sequences (B) Fraction of uAUG-containing n-mer sequences conserved in human and mouse 5'-UTRs.

An earlier study of excess conservation of uAUGs used a total of 1955 pairwise alignments of human and mouse 5'-UTR sequences (Churbanov A, Rogozin I B, Babenko V N, Ali H, Koonin E V: Evolutionary conservation suggests a regulatory function of AUG triplets in 5'-UTRs of eukaryotic genes. Nucleic Acids Res 2005, 33(17):5512-5520). The authors generated the alignments after careful pre-processing steps to remove any coding sequences that may have been mis-annotated as leader sequences. We used this well-curated alignment data to compile sequences containing uAUGs from human 5'-UTRs (see Methods), generating a total of 4009 uAUG 11-mers. The number of uAUGs per 5'-UTR ranges from one to 20, with 68% of the 1955 human 5'-UTRs containing at most two (FIG. 11A). In order to investigate conservation patterns of these n-mers we separated them into 2935 conserved and 1074 non-conserved sequences. The uAUG sequences appear to be highly conserved between both human and mouse UTRs, with all 7-mers having 100% identities and roughly 70% of 11-mers being conserved (FIG. 11B).

Mature human miRNA sequences (miRBase, version 11.0) (Griffiths-Jones S, Saini H K, van Dongen S, Enright A J: miRBase: tools for microRNA genomics. Nucleic Acids Res 2008, 36(Database issue):D154-158) were downloaded and categorized as conserved (471 sequences) or non-conserved (206 sequences) miRNAs (see Methods). To reveal preferential interaction with any portion of the miRNA we split each sequence into its 5'- and 3'-ends, the former containing the seed region. We then looked for sequence matches between miRNA ends and the uAUG-containing sequences generated. This was done in two steps: 1) a thermodynamics-based search using RNAhybrid (Rehmsmeier M, Steffen P, Hochsmann M, Giegerich R: Fast and effective prediction of microRNA/target duplexes. Rna 2004, 10(10):1507-1517) with a ΔG cutoff≤−14 kcal mol$^{-1}$ followed by 2) a filter step to look for 7 or more consecutive matches with zero or one GU wobbles. To control for spurious hits, the number of interacting pairs was compared to the number obtained after shuffling the mature miRNAs sequences and repeating the search procedure.

Figure 12:
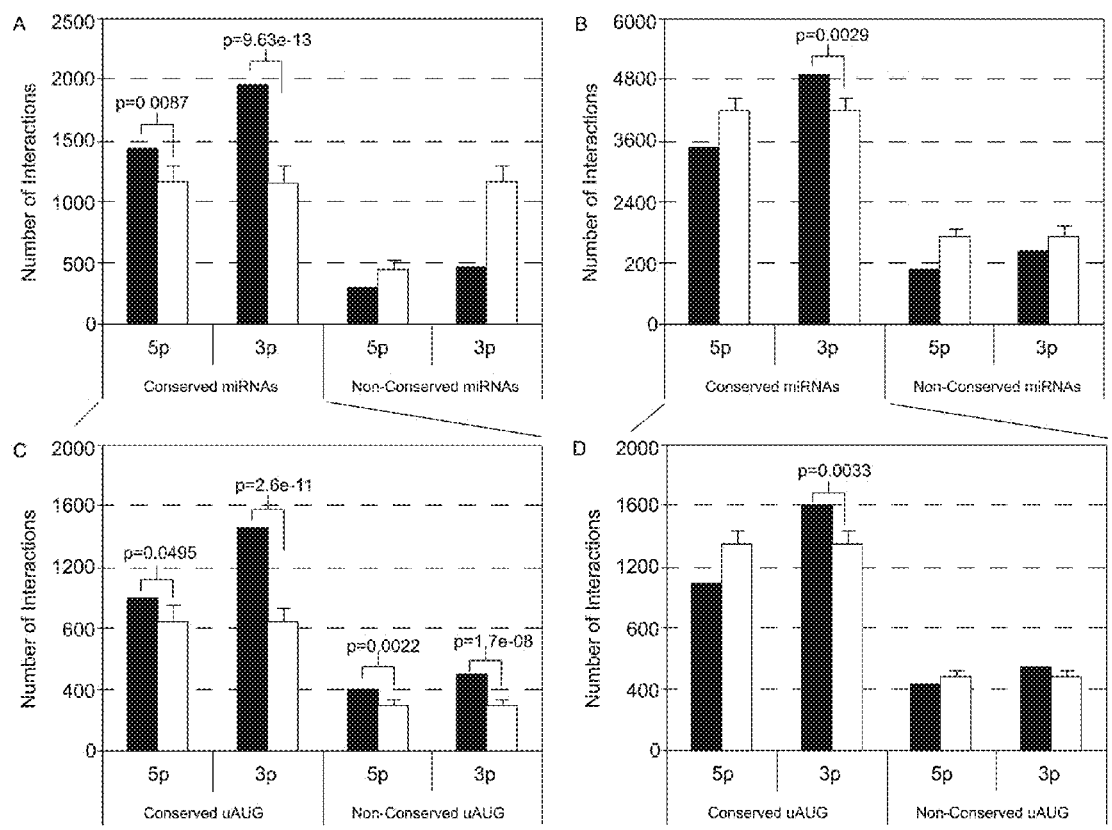
FIG. 12 provides results for the interaction of miRNAs with uAUG sequences. Each predicted interaction is characterized by a 7-mer consecutive match between the indicated half of mature miRNA (5p and 3p for the 5'- and 3'-end respectively) and uAUG sequence with $\Delta G_{37} \leq -14$ kcal mol$^{-1}$. Closed bars represent actual counts and open bars represent average number of counts over 1000 repetitions of miRNA shuffling. Error bars represent the standard deviations. Significant outcomes are indicated with the corresponding p-values (A, B) Number of interactions between uAUG sequences (4009 in total) and conserved and non-conserved miRNAs (471 and 206 in total respectively) without GU wobbles (A) and with at most one GU wobble (B). (C, D) Number of interactions between conserved miRNAs and uAUG sequences (2935 conserved and 1074 non-conserved) without GU wobbles (C) and with at most one GU wobble (D).

We observed many predicted interactions between uAUG sequences and the two miRNA ends, characterized by a dependency on conservation of miRNAs. Only conserved miRNAs showed a significant number of interactions while non-conserved miRNAs were no better than their shuffled cohorts (FIGS. 12A and 12B). There were a number of 7-mer Watson-Crick complementary matches between the 5'-ends of conserved miRNAs and uAUG sequences (FIG. 12A). Interestingly, there seemed to be a greater number of such interactions at the 3'-ends (FIG. 12A), which suggests a preference for pairing between uAUGs and 3'-ends. These interactions arose from 46 conserved miRNAs and 263 unique uAUG motifs of length 7 or more (Table 6). A previous study also reported observations wherein 5'-UTR and coding regions participate in binding the 3'-end of the highly conserved miRNA, let-7 (Forman J J, Legesse-Miller A, Coller H A: A search for conserved sequences in coding regions reveals that the let-7 microRNA targets Dicer within its coding sequence. Proc Natl Acad Sci USA 2008, 105(39):14879-1488). Further, when we included at most one GU wobble the only significant result that persisted was the interaction with the 3'-ends of conserved miRNAs (FIG. 12B). We conducted a genome-wide motif study of 5'-UTRs and 3'-UTRs and observed a similar propensity for interaction between 5'-UTRs and 3'-ends of miRNAs, few of which were validated (unpublished data). The preference for interaction with 3'-ends, suggests the role of non-seed region matches in the 5'-UTR, while seed-region matches prevail in the 3'-UTR. This may explain the fact that there are very few known endogenous targets on the 5'-UTR that exhibit seed-matches (Xie X, Lu J, Kulbokas E J, Golub T R, Mootha V, Lindblad-Toh K, Lander E S, Kellis M: Systematic discovery of regulatory motifs in human promoters and 3' UTRs by comparison of several mammals. Nature 2005, 434(7031):338-345.). We conducted a brief GO-term investigation into the nature of genes containing the uAUGs listed in Table 6. Out of a total 1071 genes that contained these uAUGs we were able to retrieve annotations for 678 genes. The majority of these 678 were found to be involved in transcription factor activity.

TABLE 1

MicroRNAs predicted to interact with uAUG-containing motifs

| miRNA* | uAUG-containing motifs§ |
|---|---|
| hsa-let-7d | AACUAUG, ACUAUGCAA, CUAUGCAAC |
| hsa-miR-130a/b | AUGCCCU |
| hsa-miR-132 | GACCAUGGCU (SEQ ID NO: 372) |
| hsa-miR-146a | ACCCAUGG, CCCAUGGAA |
| hsa-miR-146b-5p | GCCUAUGG, CCUAUGGAA |
| hsa-miR-194 | CCACAUGGA, ACAUGGAG |
| hsa-miR-199a-3p | ACCAAUGUG |
| hsa-miR-202 | UCCCAUGC, CCCAUGCC |
| hsa-miR-219-2-3p | ACAGAUGU, CAGAUGUCC, AGAUGUCCA |
| hsa-miR-297 | GCACAUGC |
| hsa-miR-299-5p | AUGUAUGUGGG (SEQ ID NO: 373) |
| hsa-miR-31 | GCUAUGCCA, CUAUGCCAG |
| hsa-miR-324-5p | ACCAAUGCC, CAAUGCCC |
| hsa-miR-33a/b | GCAAUGCA, CAAUGCAA, AUGCAAC |
| hsa-miR-34b | AUGGCAG |
| hsa-miR-363 | ACAGAUGGA, AGAUGGAU, CAGAUGGAU, GAUGGAU |
| hsa-miR-376b | AACAUGGAUU |
| hsa-miR-380 | AAGAUGUGG, AGAUGUGGA, GAUGUGGA |
| hsa-miR-431 | GCAUGACG, CAUGACGG |
| hsa-miR-432 | CCCAAUGA, CCAAUGAC |
| hsa-miR-448 | AUGGGAC |
| hsa-miR-450b-3p | AUGGAUGCA, GGAUGCAA |
| hsa-miR-455-3p | GUAUAUGC, AUAUGCC |
| hsa-miR-455-5p | CGAUGUAG , GAUGUAGU |
| hsa-miR-487a | CUGGAUGUC |
| hsa-miR-487b | GUGGAUGA , UGGAUGAC |
| hsa-miR-490-3p | CAGCAUGGAG, (SEQ ID NO: 374) AGCAUGGAGU (SEQ ID NO: 375) |
| hsa-miR-491-5p | CCUCAUGGAAG (SEQ ID NO: 376) |
| hsa-miR-513b | AUAAAUGACA, (SEQ ID NO: 377) AUGACAC |
| hsa-miR-556-3p | AAAGAUGAGC, (SEQ ID NO : 378) AGAUGAGCU |
| hsa-miR-562 | GCAAAUGGU |
| hsa-miR-580 | CCUAAUGA, AUGAUUC |
| hsa-miR-583 | UAAUGGGA, AAUGGGAC |
| hsa-miR-598 | GACGAUGAC, AC GAUGACA |
| hsa-miR-609 | AGAGAUGAG, GAGAUGAGA |
| hsa-miR-654-3p | GGUGAUGGU |
| hsa-miR-654-5p | GCACAUG, ACAUGUUCU |

TABLE 1-continued

MicroRNAs predicted to interact
with uAUG-containing motifs

| miRNA* | uAUG-containing motifs§ |
|---|---|
| hsa-miR-767-3p | AACCAUGGG |
| hsa-miR-802 | AAGGAUGAAU (SEQ ID NO : 379) |
| hsa-miR-887 | CGGGAUGG |
| hsa-miR-889 | AAUGGUUG |
| hsa-miR-890 | ACUGAUGC, CUGAUGCC |
| hsa-miR-942 | CACAUGGCC, ACAUGGCCA |
| hsa-miR-944 | UCCGAUG |

*The 46 miRNAs represent conserved miRNAs
§Only the portion of uAUG11-mer that interacts with the 3'-end of miRNAs without a
GU wobble is presented. If a miRNA matches a uAUG sequence and its subsequence(s),
only the longest form is presented.

Considering that nearly 75% of the 11-mers were found to be conserved between human and mouse 5'-UTRs (2935 out of 4009) we investigated if the interactions with conserved miRNAs were a function of uAUG sequence conservation. Results showed no dependence on uAUG conservation when not allowing GU wobbles (FIG. 12C). However, when allowing at most one GU wobble only conserved uAUGs exhibited significant interactions with 3'-ends of miRNAs (FIG. 12D).

The above results indicate that uAUGs may participate in highly sequence-specific Watson-Crick base-pairing with miRNAs, particularly towards the 3'-ends. The fact that inclusion of a GU wobble still resulted in a significant number of interactions between the 3'-ends and uAUGs suggests functionality.

Expressed miRNAs May Bind Endogenous uAUG Sites

The analyses that follow are based on experiments with genes that contain uAUGs in their 5'-UTRs, drawing upon sequence data and results from previous experiments that attribute translational repression to the uAUGs. We also used miRNA expression evidence from several sources—these references are consolidated in the form of meta-data (Table 7). We extracted 11-mer sequences containing uAUGs for these genes and looked for interactions with conserved miRNAs using the search strategy outlined above. Based on the observations in FIGS. 12A and 12B, we allowed one GU wobble for interactions with the 3'-end and none with the 5'-end. Many of the genes contain multiple uAUGs/uORFs that have different inhibitory effects on translation. We assigned discrete values to these uAUGs that reflect their repressive capabilities on the expression of a downstream reporter. These were obtained by comparing the effect of the uAUG either to a control construct or to a construct where the uAUG under consideration is mutated. The values range from 1× to 6×, where 1× indicates that the uAUG is least repressive or does not show any effect. Sequences that limit the expression of reporter to half or one-third the control or mutant case are assigned a value of 2× or 3× respectively, and so on.

TABLE 7

Genes used in analysis along with references

| Gene | Evidence showing translational control by uAUG | miRNA expression evidence used for analysis |
|---|---|---|
| KLF9/BTEB1 | Imataka H, Nakayama K, Yasumoto K, Mizuno A, Fujii-Kuriyama Y, Hayami M: Cell-specific translational control of transcription factor BTEB expression. The role of an upstream AUG in the 5'-untranslated region. J Biol Chem 1994, 269(32): 20668-20673. | Landgraf P, Rusu M, Sheridan R, Sewer A, Iovino N, Aravin A, Pfeffer S, Rice A, Kamphorst A O, Landthaler M et al: A mammalian microRNA expression atlas based on small RNA library sequencing. Cell 2007, 129(7): 1401-1414; Chen J, Lozach J, Garcia E W, Barnes B, Luo S, Mikoulitch I, Zhou L, Schroth G, Fan J B: Highly sensitive and specific microRNA expression profiling using BeadArray technology. Nucleic Acids Res 2008, 36(14): e87; Hohjoh H, Fukushima T: Marked change in microRNA expression during neuronal differentiation of human teratocarcinoma NTera2D1 and mouse embryonal carcinoma P19 cells. Biochem Biophys Res Commun 2007, 362(2): 360-367. |
| KLF13/RFLAT-1 | Nikolcheva T, Pyronnet S, Chou S Y, Sonenberg N, Song A, Clayberger C, Krensky A M: A translational rheostat for RFLAT-1 regulates RANTES expression in T lymphocytes. J Clin Invest 2002, 110(1): 119-126. | Landgraf P, Rusu M, Sheridan R, Sewer A, Iovino N, Aravin A, Pfeffer S, Rice A, Kamphorst A O, Landthaler M et al: A mammalian microRNA expression atlas based on small RNA library sequencing. Cell 2007, 129(7): 1401-1414; Chen J, Lozach J, Garcia E W, Barnes B, Luo S, Mikoulitch I, Zhou L, Schroth G, Fan J B: Highly sensitive and specific microRNA expression profiling using BeadArray technology. Nucleic Acids Res 2008, |

TABLE 7-continued

Genes used in analysis along with references

| Gene | Evidence showing translational control by uAUG | miRNA expression evidence used for analysis |
|---|---|---|
| | | 36(14): e87; Lawrie C H, Saunders N J, Soneji S, Palazzo S, Dunlop H M, Cooper C D, Brown P J, Troussard X, Mossafa H, Enver T et al: MicroRNA expression in lymphocyte development and malignancy. Leukemia 2008, 22(7): 1440-1446; Takada S, Berezikov E, Yamashita Y, Lagos-Quintana M, Kloosterman W P, Enomoto M, Hatanaka H, Fujiwara S, Watanabe H, Soda M et al: Mouse microRNA profiles determined with a new and sensitive cloning method. Nucleic Acids Res 2006, 34(17): e115. |
| MOR | Song K Y, Hwang C K, Kim C S, Choi H S, Law P Y, Wei L N, Loh H H: Translational repression of mouse mu opioid receptor expression via leaky scanning. Nucleic Acids Res 2007, 35(5): 1501-1513. | Landgraf P, Rusu M, Sheridan R, Sewer A, Iovino N, Aravin A, Pfeffer S, Rice A, Kamphorst A O, Landthaler M et al: A mammalian microRNA expression atlas based on small RNA library sequencing. Cell 2007, 129(7): 1401-1414; Chen J, Lozach J, Garcia E W, Barnes B, Luo S, Mikoulitch I, Zhou L, Schroth G, Fan J B: Highly sensitive and specific microRNA expression profiling using BeadArray technology. Nucleic Acids Res 2008, 36(14): e87. |
| CHOP | Jousse C, Bruhat A, Carraro V, Urano F, Ferrara M, Ron D, Fafournoux P: Inhibition of CHOP translation by a peptide encoded by an open reading frame localized in the chop 5'UTR. Nucleic Acids Res 2001, 29(21): 4341-4351. | Landgraf P, Rusu M, Sheridan R, Sewer A, Iovino N, Aravin A, Pfeffer S, Rice A, Kamphorst A O, Landthaler M et al: A mammalian microRNA expression atlas based on small RNA library sequencing. Cell 2007, 129(7): 1401-1414; Chen J, Lozach J, Garcia E W, Barnes B, Luo S, Mikoulitch I, Zhou L, Schroth G, Fan J B: Highly sensitive and specific microRNA expression profiling using BeadArray technology. Nucleic Acids Res 2008, 36(14): e87. |
| MDM2 | Jin X, Turcott E, Englehardt S, Mize G J, Morris D R: The two upstream open reading frames of oncogene mdm2 have different translational regulatory properties. J Biol Chem 2003, 278(28): 25716-25721. | Landgraf P, Rusu M, Sheridan R, Sewer A, Iovino N, Aravin A, Pfeffer S, Rice A, Kamphorst A O, Landthaler M et al: A mammalian microRNA expression atlas based on small RNA library sequencing. Cell 2007, 129(7): 1401-1414; Chen J, Lozach J, Garcia E W, Barnes B, Luo S, Mikoulitch I, Zhou L, Schroth G, Fan J B: Highly sensitive and specific microRNA expression profiling using BeadArray technology. Nucleic Acids Res 2008, 36(14): e87. |
| ADH5/FDH | Kwon H S, Lee D K, Lee J J, Edenberg H J, Ahn Y H, Hur M W: Posttranscriptional regulation of human ADH5/FDH and Myf6 gene expression by upstream AUG codons. Arch Biochem Biophys 2001, 386(2): 163-171. | Landgraf P, Rusu M, Sheridan R, Sewer A, Iovino N, Aravin A, Pfeffer S, Rice A, Kamphorst A O, Landthaler M et al: A mammalian microRNA expression atlas based on small RNA library sequencing. Cell 2007, 129(7): 1401-1414; Chen J, Lozach J, Garcia E W, Barnes B, Luo S, Mikoulitch I, Zhou L, Schroth G, Fan J B: Highly sensitive and specific microRNA expression profiling |

TABLE 7-continued

Genes used in analysis along with references

| Gene | Evidence showing translational control by uAUG | miRNA expression evidence used for analysis |
|---|---|---|
| | | using BeadArray technology. Nucleic Acids Res 2008, 36(14): e87. |

* Evidence for expression of miRNAs in mouse N2A cells was acquired through personal communication with authors of (Hohjoh H, Fukushima T: Marked change in microRNA expression during neuronal differentiation of human teratocarcinoma NTera2D1 and mouse embryonal carcinoma P19 cells. Biochem Biophys Res Commun 2007, 362(2): 360-367).

We not only observed complementary matches with conserved miRNA sequences but also confirmed the presence of many of the predicted miRNAs in cell-lines where repression was observed (Table 8). There also appears to be an association between repressive strength of uAUGs and miRNA target predictions. Two uAUGs that have little or no effect on repression, indicated by '1×' in Table 8, lack miRNA interaction sites. Conversely, uAUGs with strong repressive potential (2×-6×) are complementary to expressed miRNAs except in the case of the first uAUG in the ADH5/FDH gene where expressions of the predicted miRNAs have not been detected. Note that miRNAs can act in a combinatorial manner on uAUGs to produce a net repressive effect. These observations suggest that some of the uAUG sequences are miRNA-specific and functional target sites.

TABLE 8

Genes containing uAUGs predicted to interact with expressed miRNAs

| Gene | uAUG† | Cell line used in experiments | miRNAs predicted to interact§ | miRNA expression in cell-lines tested‡ |
|---|---|---|---|---|
| MOR | 1 gcccAUGctcc SEQ ID NO: 380 (1×) | HEK293 | hsa-miR-146a (3′) hsa-miR-202a (3′) | No |
| | 2 ggggAUGcuaa SEQ ID NO: 381 (2×) | | hsa-miR-324-5p(5′) hsa-miR-517b-(5′) | Yes Yes |
| | 3 aaggAUGcgcc SEQ ID NO: 382 (3×) | | hsa-miR-323-5p (3′) hsa-miR-324-5p (5′) hsa-miR-450b-3p (3′) | No Yes No |
| CHOP | 1 uaucAUGuuaa SEQ ID NO: 383 (1×) | HeLa | None | |
| | 2 aaagAUGagcg SEQ ID NO: 384 (6×) | | hsa-miR-574-39 (5′) hsa-miR-556-39 (3′) | Yes No |
| | 3 gcagAUGugcu SEQ ID NO: 385 (2×) | | hsa-miR-219-2-3p (3′) | No* |
| MDM2 | 1 aaagAUGgagc SEQ ID NO: 386 (3×) | HeLa | hsa-miR-363 (3′) | Yes |
| | 2 uggaAUGaucc SEQ ID NO: 387 (1×) | | None | |
| ADH5/FDH | 1 gcccAUGccuc SEQ ID NO: 388 (4×) | HeLa | hsa-miR-146a (3′) hsa-miR-202 (3′) | No No |
| | 2 ccggAUGucag SEQ ID NO: 389 (4×) | | hsa-miR-219-1-3p (3′) hsa-miR-219-2-3p (3′) hsa-miR-487a (3′) hsa-miR-489 (5′) | No* No* No No |
| KLF13 | 1 SEQ ID NO: 390 cacaUAGcgcg# | Jurkat | hsa-miR-323-5p (3′) hsa-miR-103 (5′) hsa-miR-107 (5′) hsa-miR-33a (5′) hsa-miR-586 (5′) | No Yes Yes Yes No |
| | 2 SEQ ID NO: 391 ccccAUGcgcu | | hsa-miR-202 (3′) | No |

TABLE 8-continued

Genes containing uAUGs predicted to interact with expressed miRNAs

| Gene | uAUG[†] | Cell line miRNAs used in experiments | miRNAs predicted to interact[§] | miRNA expression in cell-lines tested[‡] |
|---|---|---|---|---|
| | 3 SEQ ID NO: 392 gcggAUGcgcg | | hsa-miR-450b-3p (3') hsa-miR-324-5p (5') | No Yes |

[†]uAUGs shown in caps.
[#]uAUG not present in the GenBank entry but used in reporter constructs [25].
[§]Numbers in parentheses indicate the miRNA end predicted to interact. miRNAs in italics indicate matches with one GU wobble.
[‡]Reference for evidence of expression.
*Expression of mature miR-219, which corresponds to the 5 p arm of the precursor, was detected by Chen et al., but that of 3 p was not assayed for on the microarray [40].

KLF Genes are Probable 5'-UTR miRNA Targets

Kruppel-like factors (KLFs) are transcriptional regulators that contain a characteristic zinc-finger domain and are known to play a role in differentiation and other cellular events (Bieker J J: Kruppel-like factors: three fingers in many pies. J Biol Chem 2001, 276(37):34355-34358; Black A R, Black J D, Azizkhan-Clifford J: Sp1 and kruppel-like factor family of transcription factors in cell growth regulation and cancer. J Cell Physiol 2001, 188(2):143-160). There are as many as 15 members in this family, seven of them containing at least one uAUG. Using the criteria set above we identified 7-mer matches between uAUG-containing sequences and miRNAs in all seven of these genes (Table 9). Two of these, KLF9 and KLF13, also called BTEB1 and RFLAT-1 respectively, are known to be translationally regulated by uAUGs in their 5'-UTRs. The uAUGs in these two genes have been implicated in cell-specific control of protein expression though their respective transcripts are present in many other tissues, suggesting a post-transcriptional mechanism of gene regulation.

TABLE 9 uAUGs from members of the KLF family predicted to interact with conserved miRNAs

| KLF Gene[§] | uAUG[†] | miRNAs predicted to interact[‡] |
|---|---|---|
| KLF6 (NM_001300) | 1 uugcAUGaaac SEQ ID NO: 393 | hsa-miR-93 (3') |
| KLF7 (NM_003709) | 1 cuggAUGccuc SEQ ID NO: 394 | hsa-miR-450b-3p (3') hsa-miR-487a (3') |
| | 2 cuggAUGucug SEQ ID NO: 395 | hsa-miR-450b-3p (3') hsa-miR-487a (3') |
| KLF8 (NM_007250) | 1 cucuAUGauuc SEQ ID NO: 396 | hsa-miR-376a (5') hsa-miR-376b (5') hsa-miR-376c (5') |
| | 2 cuuuAUGuuca SEQ ID NO: 397 | None |
| | 3 gaggAUGggug SEQ ID NO: 398 | hsa-miR-331-3p (3') hsa-miR-363 (3') hsa-miR-802 (3') hsa-miR-99b (5') |
| | 4 uuggAUGcuug SEQ ID NO: 399 | hsa-miR-450b-3p (3') |
| | 5 cgcuAUGucag SEQ ID NO: 400 | hsa-miR-31 (3') |
| | 6 cagaAUGgggc SEQ ID NO: 401 | hsa-miR-448 (3') hsa-miR-583 (3') hsa-miR-136 (5') |
| | 7 gaguAUGagcc SEQ ID NO: 402 | hsa-miR-767-3p (5') |
| | 8 cggcAUGaguu SEQ ID NO: 403 | hsa-miR-574-3p (5') |
| KLF10 (NM_001032282, isoform a) | 1 gauuAUGcaau SEQ ID NO: 404 | hsa-let-7d (3') hsa-miR-153 (5') |
| | 2 agcaAUGgcuc SEQ ID NO: 405 | hsa-miR-160 (5') |
| | 3 caucAUGcauu SEQ ID NO: 406 | None |
| | 4 aagaAUGuuuu SEQ ID NO: 407 | None |
| | 5 uuuaAUGgaaa SEQ ID NO: 408 | None |
| KLF12 (NM_007249) | 1 aucaAUGugac SEQ ID NO: 409 | hsa-miR-199a-3p (3') hsa-miR-23a (5') hsa-miR-23b (5') |
| | 2 acaaAUGgaug SEQ ID NO: 410 | hsa-miR-136 (5') |
| | 3 auggAUGaaug SEQ ID NO: 411 | hsa-miR-450b-3p (3') hsa-miR-487b (3') hsa-miR-802 (3') |
| | 4 augaAUGaaua SEQ ID NO: 412 | None |

[§]KLF13 and KLF9 are presented along with miRNA expression data in Table 8 and 10, respectively.
[†]uAUGs are shown in caps.
[‡]Numbers in parentheses indicate the miRNA end predicted to interact. miRNAs in italics indicate matches with one GU wobble.

Specifically, protein expression of KLF9, whose 5'-UTR contains 10 uAUGs, is limited to brain tissue though its mRNA is expressed ubiquitously (Imataka H, Nakayama K, Yasumoto K, Mizuno A, Fujii-Kuriyama Y, Hayami M: Cell-specific translational control of transcription factor BTEB expression. The role of an upstream AUG in the 5'-untranslated region. J Biol Chem 1994, 269(32):20668-20673). The 5'-UTR, particularly the portion containing uAUGs 6 and 7, suppressed reporter gene translation in HeLa cells but not in mouse neuroblastoma (N2A) cells (Imataka et al). This observation was even more intriguing because peptides from the two uORFs starting from uAUG6 and uAUG7 have not been detected (Imataka et al). Similarly, though KLF13 mRNA is expressed in multiple tissues, protein expression was only detected in adult spleen and lung tissues (Song A, Nikolcheva T, Krensky A M: Transcriptional regulation of RANTES expression in T lymphocytes. Immunol Rev 2000, 177:236-245). While KLF13 mRNA levels are constant throughout T-cell activation, KLF13 protein is only expressed later on in the activation process (Nikolcheva T, Pyronnet S, Chou S Y, Sonenberg N, Song A, Clayberger C, Krensky A M: A translational rheostat for RFLAT-1 regulates RANTES expression in T lymphocytes. J Clin Invest 2002, 110(1):119-126). The presence of several uAUGs in its 5'-UTR down-regulated translation of the reporter gene in Jurkat T-cells and, to a lesser degree, in HEK293 cells (Nikolcheva et al.).

We decided to focus our analysis on KLF9 uAUGs since the effects of wild-type and mutant constructs used to elucidate the roles of uAUGs were demonstrated in both cell-lines relevant to tissue specificity. We extracted uAUG 11-mers from the KLF9 5'-UTR sequence used in the experimental study (Imataka et al.) and searched for interactions with both ends of conserved miRNAs. Since the 5'-UTR study for KLF9 was also done in the mouse neuroblastoma (N2A) cell line, we used both mouse and human miRNAs in the analysis. All uAUGs except uAUG5 and uAUG8 interacted with at least one miRNA (Table 10). The ninth uAUG was predicted to interact with as many as five miRNAs. Most of these predicted miRNAs are expressed in HeLa cells but not in N2A cells, including those that match uAUG6 and uAUG7. Only mmu-miR-16 and mmu-miR-543 were detected in N2A cells.

TABLE 5

KLF9 uAUGs predicted to interact with miRNAs in HeLa cells

| | uAUG[S] | miRNAs predicted to interact[†] | miRNA expressed in cell-lines tested?[‡] | |
|---|---|---|---|---|
| | | | HeLa | N2A |
| 1 | cauaAUGgggu SEQ ID NO: 413 | hsa-miR-583 (3') hsa-miR-490-3p (3') mmu-miR-490 (3') | Yes[40] — — | — — — |
| 2 | aaagAUGuguc SEQ ID NO: 414 | miR-380 (3') hsa-miR-576-5p (3') | Yes[40] Yes[40] | — — |
| 3 | gccaAUGccag SEQ ID NO: 415 | miR-16 (3') hsa-miR-31 (3') miR-324-5p (3') | Yes[39],[40] Yes[39],[40] Yes[39],[40] | Yes[39],[41] — — |
| 4 | aaagAUGuguc SEQ ID NO: 416 | miR-380 (3') hsa-miR-576-5p (3') | Yes[40] Yes[40] | — — |
| 5 | uuaaAUGucag SEQ ID NO: 417 | None | — | — |
| 6 | cgugAUGggau SEQ ID NO: 418 | miR-448 (3') hsa-miR-583 (3') hsa-miR-609 (3') miR-654-3p (3') hsa-miR-605 (5') mmu-miR-325 (3') | — Yes[40] Yes[40] — — — | — — — — — — |
| m6 | cgugAAGggau SEQ ID NO: 419 | hsa-miR-491-3p (3') miR-188-5p (5') hsa-miR-211 (3') hsa-miR-520h (3') | — Yes[40] — — | — — — — |
| 7 | gagaAUGccgg SEQ ID NO: 420 | hsa-miR-31 (3') | Yes[39],[40] | — |
| m7 | gagaAAGccgg SEQ ID NO: 421 | None | — | — |
| 8 | gugaAUGuccu SEQ ID NO: 422 | None | — | — |
| 9 | guggAUGcugc SEQ ID NO: 423 | hsa-miR-450b-3p (3') hsa-miR-487b (3') miR-103 (5') miR-107 (5') miR-338-3p (5') mmu-miR-376b (3') mmu-miR-450a-3p (3') | — — Yes[40] Yes[40] Yes[39],[40] — — | — — Yes[41] — — Yes[41] — |
| 10 | aaagAUGaggg SEQ ID NO: 424 | hsa-miR-556-3p (3'), hsa-miR-609 (3') | — Yes[40] | — — |

[S]uAUG shown in caps, mutated sequences prefixed with letter 'm', and mutated positions shown in bold.
[†]Three letter species codes (hsa/mmu) are indicated only when one sequence interacts and omitted if both interact. Numbers in parentheses indicate the miRNA end predicted to interact. miRNAs in italics indicate matches with one GU wobble.
[‡]Reference for evidence of expression.

Regulatory roles of each uAUG/uORF may be studied by mutating one or more of the uAUGs to mitigate repression. In the case of KLF9, mutation of uAUG6 or 7 or both relieved translation repression (Imataka et al.). However, uAUG6 inhibits translation to a greater extent compared to uAUG7, the translation efficiency of the uAUG6 mutant construct being 5 times that of the wild-type construct compared to a two-fold increase for the uAUG7 mutant, based on Imataka et al.'s FIG. 7 (Imataka et al.). Interestingly, five human miRNAs are predicted to interact with uAUG6, of which two are expressed in the HeLa cell lines and none in N2A cells (Table 5 and Additional file 2). Only one expressed miRNA, hsa-miR-31, is predicted to bind uAUG7.1f these two uAUGs are indeed miRNA interaction sites, their mutation should presumably eliminate interactions with the miRNAs predicted in Table 5. To test this assumption we repeated analysis using mutated uAUG sequences that had been shown to relieve translational repression. When mutated, uAUGs implicated in mediation of translation repression in KLF9 showed fewer predicted interactions with miRNAs (Table 5, sequences m6 and m7) compared to wild-type sequences. Moreover, there was little evidence for expression of miRNAs matching mutated uAUG sequences.

Discussion

Though uAUGs are known to act in post-transcriptional control of gene expression there is no clear account of the mechanism involved when differences in activity of uAUGs exist across cell or tissue types. While studying uAUGs and miRNAs independent of one another, researchers observed that uAUGs affect gene expression by reducing protein levels while maintaining mRNA levels, just as with miRNA-mediated gene regulation.

Target sites for miRNAs have conventionally been thought to reside on conserved regions of the 3'-UTR and are predicted to bind the seed-region of a miRNA (Lewis B P, Burge C B, Bartel D P: Conserved seed pairing, often flanked by adenosines, indicates that thousands of human genes are microRNA targets. Cell 2005, 120(1):15-20). We used a combination of thermodynamic and sequence-based searches and found many uAUG sites on the 5'-UTR that are predicted to interact with conserved miRNAs. Though both ends of these miRNAs exhibited a significant number of interactions, we found a propensity for 3'-end interaction with uAUGs. These observations are in sharp contrast to results which show a lack of appreciable seed-matches on 5'-UTRs (Xie X, Lu J, Kulbokas E J, Golub T R, Mootha V, Lindblad-Toh K, Lander E S, Kellis M: Systematic discovery of regulatory motifs in human promoters and 3' UTRs by comparison of several mammals. Nature 2005, 434(7031):338-345). Forman et al. have also shown in silico that a well-conserved miRNA, let-7, is predicted to base-pair with the 5'-UTRs through the remainder of the miRNA apart from the seed portion (Forman J J, Legesse-Miller A, Coller H A: A search for conserved sequences in coding regions reveals that the let-7 microRNA targets Dicer within its coding sequence. Proc Natl Acad Sci USA 2008, 105(39):14879-14884). Recently, we computationally identified hundreds of human miRNAs that match 5'-UTRs through their 3'-ends through a genome-wide motif study and experimentally validated that repression occurs through such an interaction (unpublished data, manuscript under review). The signal-to-noise ratio observed in the interaction between uAUG motifs and miRNAs surpassed those in the genome-wide motif study, thereby suggesting the importance of this interaction. Based on these evidences, we hypothesized that the overlap in miRNA and uAUG function may arise from underlying sequence-specific interactions.

Examining many genes where uAUGs have regulatory properties, we demonstrated the connection between uAUG-mediated repression and their likelihood as binding sites for conserved miRNAs. miRNA expression data support this link by confirming the presence of miRNAs in cell-lines where reporter translation is affected by uAUGs. Further, we predict that many uAUGs in the KLF family of genes are miRNA-binding sites. Two uAUGs in the well-studied KLF9 are proven down-regulators of protein expression with regulation observed only in HeLa cells. Many miRNAs likely to interact with these two sequences were found to be expressed in the HeLa and not in N2A cells where regulation was not observed.

As mentioned in a previous study and also demonstrated by the GO-term analysis in our results, many genes that contain uAUGs are transcription factors (Churbanov A, Rogozin I B, Babenko V N, Ali H, Koonin E V: Evolutionary conservation suggests a regulatory function of AUG triplets in 5'-UTRs of eukaryotic genes. Nucleic Acids Res 2005, 33(17):5512-5520). Two reports show that several miRNAs and transcription factors in C. elegans and mammals are involved in feedback circuits (Kim J, Inoue K, Ishii J, Vanti W B, Voronov S V, Murchison E, Hannon G, Abeliovich A: A MicroRNA feedback circuit in midbrain dopamine neurons. Science 2007, 317(5842):1220-1224; Martinez N J, Ow M C, Barrasa M I, Hammell M, Sequerra R, Doucette-Stamm L, Roth F P, Ambros V R, Walhout A J: A C. elegans genome-scale microRNA network contains composite feedback motifs with high flux capacity. Genes Dev 2008, 22(18):2535-2549). Expanding these analyses to include transcription factors containing uAUGs in the 5'-UTRs might reveal more such miRNA-transcription factor regulatory networks.

Several other evidences point to the possible interaction between miRNAs and uAUGs on the 5'-UTRs. Orom et al. showed that miR-10a binds sequences downstream of a 5'-oligopyrimidine tract (5'-TOP) on RPSI6, a gene encoding a ribosomal protein, to regulate its translation (Orom U A, Nielsen F C, Lund A H: MicroRNA-10a binds the 5'UTR of ribosomal protein mRNAs and enhances their translation. Mol Cell 2008, 30(4):460-471). This exact binding site on the 5'-UTR was thought to be responsible for conferring cell-specific translational regulation (Avni D, Biberman Y, Meyuhas O: The 5' terminal oligopyrimidine tract confers translational control on TOP mRNAs in a cell type- and sequence context-dependent manner. Nucleic Acids Res 1997, 25(5): 995-1001). Taken together with these findings, our results suggest that miRNAs can also interact with uAUG sequences and confer tissue specificity. This would constitute a unifying mechanism of translation repression for miRNAs and uAUGs. We specifically propose that the interaction of miRNAs with uAUGs may impede the progress of the scanning 40S ribosome subunit. Interestingly, primer extension (toeprint) analysis reveals the presence of a 40S ribosomal subunit alone at the start codon on miRNA-repressed mRNAs (Wang B, Yanez A, Novina C D: MicroRNA-repressed mRNAs contain 40S but not 60S components. Proc Natl Acad Sci USA 2008, 105(14):5343-5348). The same technique also reveals stalling of ribosomes in the vicinity of uAUGs (Kwon H S, Lee D K, Lee J J, Edenberg H J, Ahn Y H, Hur M W: Posttranscriptional regulation of human ADH5/FDH and Myf6 gene expression by upstream AUG codons. Arch Biochem Biophys 2001, 386(2):163-171; Song K Y, Hwang C K, Kim C S, Choi H S, Law P Y, Wei L N, Loh H H: Translational repression of mouse mu opioid receptor expression via leaky scanning Nucleic Acids Res 2007, 35(5):1501-1513; Gaba A, Wang Z, Krishnamoorthy T, Hinnebusch A G, Sachs M S: Physical evidence for distinct mechanisms of translational control by upstream open reading frames. Embo J 2001, 20(22):6453-6463. Furthermore, Ago2, a member of the Argonaute family of proteins and a component of the functional micro-ribonucleoprotein (miRNP) complex, was found to co-sediment with 40S-containing complexes (Wang B, Yanez A, Novina C D: MicroRNA-repressed mRNAs contain 40S but not 60S components. Proc Natl Acad Sci USA 2008, 105(14):5343-5348; Peters L, Meister G: Argonaute proteins: mediators of RNA silencing. Mol Cell 2007, 26(5): 611-623; Tolia N H, Joshua-Tor L: Slicer and the argonautes. Nat Chem Biol 2007, 3(1):36-43). These facts indicate that miRNAs associated with miRNPs may recognize uAUG sequences as target sites and prevent translation.

CONCLUSIONS

In this example we present observations that suggest a miRNA role in translational control by uAUG cis-elements on the 5'-UTR. Specifically, we identified many interactions between uAUG sequences and conserved miRNAs to suggest a sequence-specific binding mechanism between these post-transcriptional regulatory factors. We also presented evidence to show that miRNAs possibly bind to uAUGs that inhibit translation of downstream reporters in cells where the miR-NAs are expressed, thus explaining differential control. This expands the range of probable miRNA targets to include many endogenous sites on the 5'-UTR.

Our current knowledge has limited us to think of miRNAs and uAUGs as distinct regulatory mechanisms. While distinct functions of miRNAs or uAUGs remain in other contexts, this example unifies them as a single translational repression phenomenon where uAUGs act as miRNA target sites and translation is hindered.

Methods uAUG Sequences

Pairwise alignments between 5'-UTRs of mammalian human and mouse cDNAs were downloaded from the ftp site listed in Churbanov et al. (Iacono M, Mignone F, Pesole G: uAUG and uORFs in human and rodent 5'untranslated mRNAs. Gene 2005, 349:97-105). From each alignment we extracted uAUG 1'-mer sequences from the human 5'-UTR beginning at position −4 and ending at position +7, with the 'A' being designated as +1 (e.g. NNNNAUGNNNN, where N is any nucleotide). Sequences of length 7 to 10 nt (e.g. AUGNNNN, NNNNAUGN, etc.) were considered when the uAUG appears towards the beginning or end of an alignment. Only uAUG sequences sharing 100% identity with the mouse homolog were categorized as conserved while others were considered as non-conserved uAUGs. Experimentally characterized uAUG sequences in Table 3 were obtained from the references listed in Table 2. For the KLF family of genes in Table 4, uAUG sequences were extracted from the 5'-UTR portions of the full RefSeq mRNA.

MicroRNA Sequences

For the motif analysis, mature miRNA sequences were downloaded from miRBase (version 11.0) (Griffiths-Jones S, Saini HK, van Dongen S, Enright AJ: miRBase: tools for microRNA genomics. Nucleic Acids Res 2008, 36(Database issue):D154-158). miRNAs present in at least one other species (e.g. hsa-let-7d and mmu-let-7d), irrespective of conservation at the nucleotide level, were categorized as conserved miRNAs (471 in total) and others as non-conserved miRNAs (206 in total). miRNAs were then split into their 5'- and 3'-halves to check for any preferential interaction with one end or the other.

Sequence Complementarity Search

A two-step strategy was employed in looking for matches between uAUG 11-mers and miRNA sequences. First, the thermodynamic search program RNAhybrid was used with −e option ($\Delta G$) set to $\leq -14$ kcal mol$^{-1}$. Next, hits with at least seven consecutive nucleotide matches were selected. (Rehmsmeier M, Steffen P, Hochsmann M, Giegerich R: Fast and effective prediction of microRNA/target duplexes. Rna 2004, 10(10):1507-1517).

Shuffling Procedure and Significance Testing miRNAs were shuffled in order to keep the nucleotide composition of the sequences intact. The search strategy above was repeated over 1000 shuffling iterations and the average number of interactions was calculated. The resulting distribution of number of interactions was assumed to be normal and significance calculated using a Z-test.

GO-Term Analysis

We used the Cytoscape plugin for BiNGO to determine the molecular functions in *H. sapiens* that are over-represented in the set of genes that contain uAUGs from Table 1. (Maere S, Heymans K, Kuiper M: BiNGO: a Cytoscape plugin to assess overrepresentation of gene ontology categories in biological networks. Bioinformatics 2005, 21(16):3448-3449). We filtered out automatic annotations (evidence code: IEA) before beginning the analysis and used the default settings for all other options provided by the software package.

miRNA Expression

For miRNAs from Landgraf et al.'s study, we used their web visualization tool to assess the presence or absence of miRNAs in a given cell-line. (Landgraf P, Rusu M, Sheridan R, Sewer A, Iovino N, Aravin A, Pfeffer S, Rice A, Kamphorst A O, Landthaler M et al: A mammalian microRNA expression atlas based on small RNA library sequencing. Cell 2007, 129(7):1401-1414). For data from Chen et al.'s study, we used a p-value cutoff of 0.01 to report the miRNA as expressed. (Chen J, Lozach J, Garcia E W, Barnes B, Luo S, Mikoulitch I, Zhou L, Schroth G, Fan J B: Highly sensitive and specific microRNA expression profiling using BeadArray technology. Nucleic Acids Res 2008, 36(14):e87). We obtained expression evidence for miRNAs of interest in N2A cells from Hohjoh et al.'s study through personal communication. Expression data from Lawrie et al.'s and Takada et al.'s studies were obtained directly from the manuscripts and supplementary information. (Hohjoh H, Fukushima T: Marked change in microRNA expression during neuronal differentiation of human teratocarcinoma NTera2D1 and mouse embryonal carcinoma P19 cells. Biochem Biophys Res Commun 2007, 362(2):360-367; Lawrie C H, Saunders N J, Soneji S, Palazzo S, Dunlop H M, Cooper C D, Brown P J, Troussard X, Mossafa H, Enver T et al: MicroRNA expression in lymphocyte development and malignancy. Leukemia 2008, 22(7):1440-1446; Takada S, Berezikov E, Yamashita Y, Lagos-Quintana M, Kloosterman W P, Enomoto M, Hatanaka H, Fujiwara S, Watanabe H, Soda M et al: Mouse microRNA profiles determined with a new and sensitive cloning method. Nucleic Acids Res 2006, 34(17):e1 15.)

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method comprising:
   a) executing by a computer a step of receiving into computer memory data identifying an mRNA nucleotide sequence representing a gene or portions thereof, the nucleotide sequence has an upstream region that is upstream of translation start site, a downstream region that is downstream of translation stop site, and an open reading frame;
   b) executing by the computer a step of receiving into computer memory data identifying a second set of microRNA (miRNA) nucleotide sequences, each microRNA sequence of the second set having a 5' miRNA section and a 3' miRNA section;
   c) executing by the computer a step of evaluating the downstream region for sub-regions that are capable of stably hybridizing to at least of a portion of the 5' miRNA section;
   d) executing by the computer a step of evaluating the upstream region for sub-regions that are capable of stably hybridizing to at least of a portion of the 3' miRNA section; and
   e) executing by the computer a step of identifying candidates for microRNA-mRNA complexes as combinations of stably hybridizing sub-regions of the downstream region to portions of the 5' miRNA section and stably hybridizing sub-regions of the upstream region to portions of the 3' miRNA section.

2. The method of claim 1 further comprising introducing the miRNA into a cell expressing the mRNA to verify regulation of the mRNA by the miRNA.

3. The method of claim 1 further comprising introducing a nucleic acid sequence that blocks miRNA into a cell expressing the mRNA to verify regulation of the mRNA by the miRNA.

4. The method of claim 1 wherein stable hybridization is determine by a degree of complementariness of the 3' miRNA section to a sub-region of the upstream region and of the 5' miRNA section to a sub-region of the downstream region.

5. The method of claim 1 wherein perfectly complementary sub-regions are most stable.

6. The method of claim 1 wherein complementary sub-regions include at most 2 mismatches.

7. The method of claim 1 wherein stable hybridization is determined by thermodynamic criteria.

8. The method of claim 7 wherein a change $\Delta G$ in Gibbs free energy for an interaction of a portion of the 5' miRNA section with sub-regions of the downstream region is evaluated with interactions having $\Delta G$ less than about $-10$ kcal/mol.

9. The method of claim 7 wherein a change $\Delta G$ in Gibbs free energy for an interaction of a portion of the 3' miRNA section with sub-regions of the upstream region is evaluated with interactions having $\Delta G$ less than about $-13$ kcal/mol.

10. The method of claim 1 wherein the mRNA has an AUG motif that intereacts with one or more portions of 3' miRNA section.

11. A non-transitory computer readable medium having instructions encoding thereon, the instructions executable by a computer processor to perform steps of:
    a) receiving into computer memory data identifying an mRNA nucleotide sequence representing a gene or portions thereof, the nucleotide sequence has an upstream region that is upstream of translation start site, a downstream region that is downstream of translation stop site, and an open reading frame;

b) receiving into computer memory data identifying a second set of microRNA (miRNA) nucleotide sequences, each microRNA sequence of the second set having a 5' miRNA section and a 3' miRNA section;

c) evaluating the downstream region for sub-regions that are capable of stably hybridizing to at least of a portion of the 5' miRNA section;

d) evaluating the upstream region for sub-regions that are capable of stably hybridizing to at least of a portion of the 3' miRNA section; and e) identifying candidates for microRNA-mRNA complexes as combinations of stably hybridizing sub-regions of the downstream region to portions of the 5' miRNA section and stably hybridizing sub-regions of the upstream region to portions of the 3' miRNA section.

* * * * *